(12) United States Patent
Youdim et al.

(10) Patent No.: US 6,316,504 B1
(45) Date of Patent: Nov. 13, 2001

(54) USE OF R-ENANTIOMER OF N-PROPARGYL-1-AMINOINDAN, SALTS, AND COMPOSITIONS THEREOF

(75) Inventors: Moussa B. H. Youdim; John P. M. Finberg, both of Tivon; Ruth Levy, Tel Aviv; Jeffrey Sterling; David Lerner, both of Jerusalem; Haim Yellin, Ramat-Gan; Alex Veinberg, Rehovot, all of (IL)

(73) Assignees: Technion Research and Development Foundation, Ltd., Technion; Teva Pharmaceuticals Industries, Ltd., Jerusalem, both of (IL)

(*) Notice: Subject to any disclaimer, the term of this patent is extended or adjusted under 35 U.S.C. 154(b) by 0 days.

(21) Appl. No.: 08/952,705
(22) PCT Filed: May 22, 1996
(86) PCT No.: PCT/US96/07465
  § 371 Date: Nov. 16, 1998
  § 102(e) Date: Nov. 16, 1998
(87) PCT Pub. No.: WO96/37199
  PCT Pub. Date: Nov. 28, 1996

(51) Int. Cl.[7] .................................................. A61K 31/135
(52) U.S. Cl. ........................... 514/657; 564/308; 514/647
(58) Field of Search .................................. 514/647, 657; 564/308

(56) References Cited

U.S. PATENT DOCUMENTS

| 3,201,470 | 8/1965 | Huebner. |
|---|---|---|
| 3,253,037 | 5/1966 | Huebner. |
| 3,513,244 | 5/1970 | Gittos et al.. |
| 4,826,875 | 5/1989 | Chiesi. |
| 5,196,583 | 3/1993 | Yamada et al.. |
| 5,387,612 | 2/1995 | Youdim et al.. |
| 5,453,446 | 9/1995 | Youdim et al.. |
| 5,457,133 | 10/1995 | Youdim et al.. |
| 5,519,061 | 5/1996 | Youdim et al.. |
| 5,532,415 | 7/1996 | Youdim et al.. |
| 5,744,500 | * 4/1998 | Youdim et al. ...................... 514/647 |

FOREIGN PATENT DOCUMENTS

| 0436492 | 10/1991 | (EP). |
|---|---|---|
| WO9511016 | 4/1995 | (WO). |

OTHER PUBLICATIONS

Finberg and Youdim, "Modification of Blood Pressure and Nictitating Membrane Response to Sympathetic Amines by Selective Monamine Oxidase Inhibitors" *British J. Pharmac.* (1985) vol. 85(2): 541–546.

Heikkila et al., Prevention of MPTP–Induced Neurotoxicity by AGN–1133 and AGN–1135, Selective Inhibitors of Monoamine Oxidase–B, *European Journal of Pharmacology*, 116, (1985) 313–317 (Exhibit 9.

Kabins and Gershon, Potential Applications for Monoamine B Inhibitors, *Dementia*, (1990) vol. 1: 323–348.

The Merck Index (Tenth ed. 1983) pp. 149, 248–249.

The Parkinson Study Group, Effect of Deprenyl on the Progression fo Disability in Early Parkinson's Disease, *New England J. Of Med.* (1989) vol. 321(20):1346–1371.

The Parkinson Study Group, Effect of Tocopherol and Deprenyl on the Progression of Disability in Early Parkinson's Disease, *New England J. Of Medicine* (1993) vol. 328(3): 176–183.

Riederer and Youdim, Monoamine Oxidase Activity and Monoamine Metabolism in Brains of Parkinson's Patients Treated with 1–Deprenyl, *J. Neurochem.* (1986) vol. 46(5); 1359–1365.

Tekes et al., Effect of Mao Inhibitors on the Uptake and Metabolism of : Dopamine in Human and Rat Brains, *Pol. J. Pharmacol. Pharm.* (1988) vol. 40 654–658.

Youdim et al., Handbook of Experimental Pharmacology vol. 90/I (1988) Chapter 3, Trendelenburg and Weiner, eds.

* cited by examiner

*Primary Examiner*—Samuel Barts
(74) *Attorney, Agent, or Firm*—John P. White; Cooper & Dunham LLP

(57) ABSTRACT

The subject invention provides R(+)-N-propargyl-1-aminoindan and pharmaceutically acceptable salts thereof, as well as pharmaceutical compositions containing the same. The subject invention also provides methods of treating a subject afflicted with Parkinson's disease, a memory disorder, dementia, depression, hyperactive syndrome, an affective illness, a neurodegenerative disease, a neurotoxic injury, stroke, brain ischemia, a head trauma injury, a spinal trauma injury, neurotrauma, schizophrenia, an attention deficit disorder, multiple sclerosis, or withdrawal symptoms, using R(+)-N-propargyl-1-aminoindan or the pharmaceutically acceptable salt of the subject invention. The subject invention further provides a method of preventing nerve damage in a subject.

12 Claims, 22 Drawing Sheets

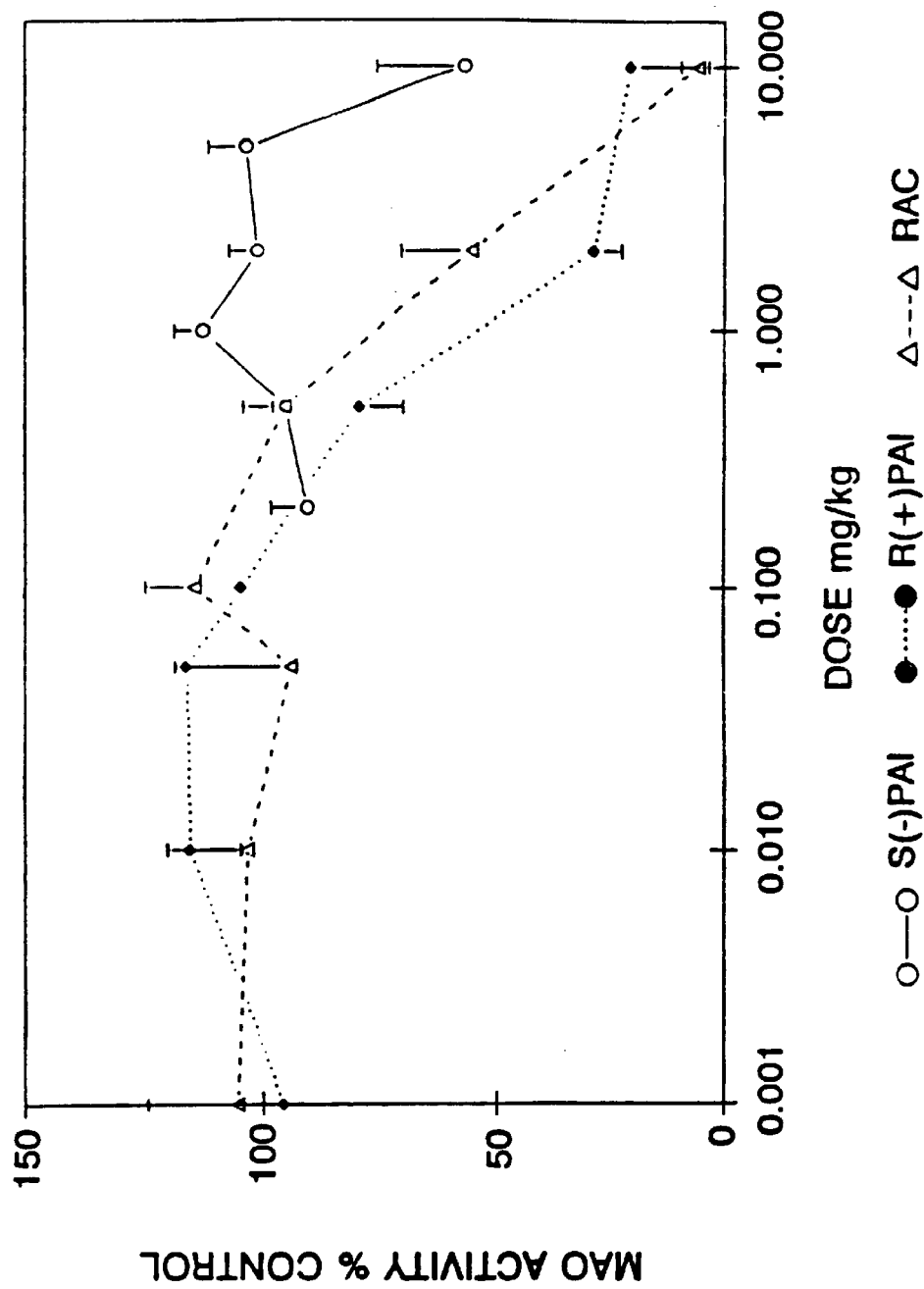

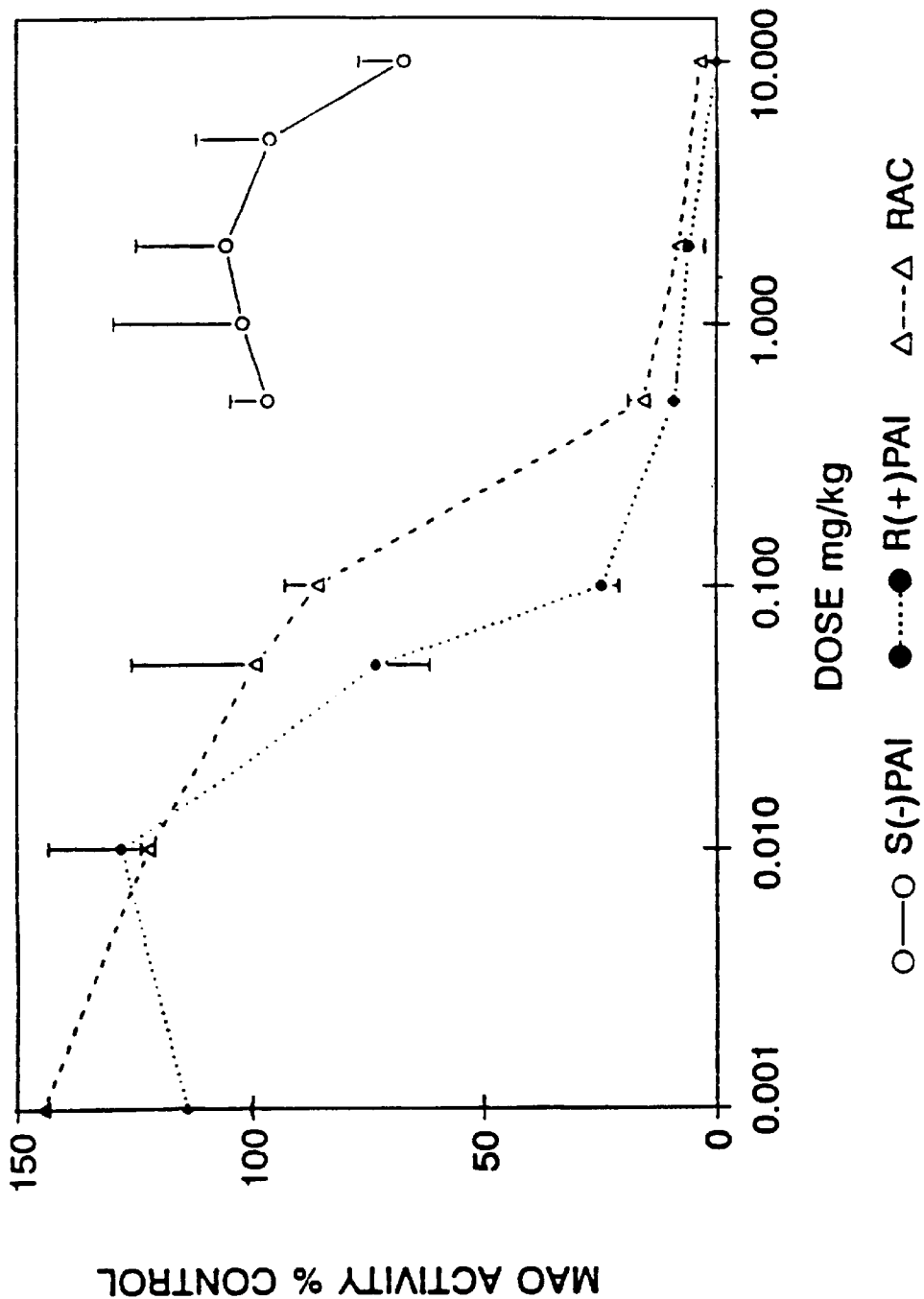

CHRONIC IN VIVO MAO-B INHIBITION IN LIVER

MAO-B ACTIVITY IN RAT BRAIN AT DIFFERENT TIMES FOLLOWING I.P. INJECTION OF R(+)PAI (1mg/kg)

USE OF R-ENANTIOMER OF N-PROPARGYL-1-AMINOINDAN, SALTS, AND COMPOSITIONS THEREOF

This application is a national stage application of PCT International Application No. PCT/US96/07465, filed May 22, 1996, on behalf of Teva Pharmaceutical Industries, Ltd. and Technion Research and Development Foundation Ltd., claiming priority of and continuation of U.S. Ser. No. 08/446,439, filed May 22, 1995, now U.S. Pat. No. 5,744,500, issued Apr. 28, 1998, which was a continuation-in-part of U.S. Ser. No. 08/139,517, filed Oct. 18, 1993, now abandoned.

Throughout this application, various references are referred to. Disclosures of these publications in their entireties are hereby incorporated by reference into this application to more fully describe the state of the art to which this invention pertains.

BACKGROUND OF THE INVENTION

I.

The subject invention is in the field of selective irreversible inhibitors of the enzyme monoamine oxidase (hereinafter MAO) and provides the R(+) enantiomer of N-propargyl-1-aminoindan (also referred to herein as PAI) which is a selective irreversible inhibitor of the B-form of monoamine oxidase enzyme (hereinafter MAO-B). The subject invention also provides pharmaceutical compositions containing R(+)PAI which are particularly useful for the treatment of Parkinson's disease, a memory disorder, dementia, depression, hyperactive syndrome, an affective illness, a neurodegenerative disease, a neurotoxic injury, stroke, brain ischemia, a head trauma injury, a spinal trauma injury, neurotrauma, schizophrenia, an attention deficit disorder, multiple sclerosis, and withdrawal symptoms.

II.

Parkinson's disease is widely considered to be the result of degradation of the pre-synaptic dopaminergic neurons in the brain, with a subsequent decrease in the amount of the neurotransmitter dopamine being released. Inadequate dopamine release, therefore, leads to the onset of disturbances of voluntary muscle control, which disturbances are symptomatic of Parkinson's disease.

Various methods of treating Parkinson's disease have been established and are currently in widespread use, including, for example, the administration of L-DOPA together with a decarboxylase inhibitor such as L-carbidopa or benserazide. The decarboxylase inhibitor protects the L-DOPA molecule from peripheral decarboxylation and thus ensures L-DOPA uptake by the remaining dopaminergic neurons in the striatum of the brain. Here, the L-DOPA is converted into dopamine resulting in increased levels of dopamine in these neurons. In response to physiological impulses, these neurons are therefore capable of releasing larger amounts of dopamine at levels which approximate the normal required levels. L-DOPA treatment thus alleviates the symptoms of the disease and contributes to the well-being of the patient.

However, L-DOPA treatment has its drawbacks, the main one being that its effectiveness is optimal only during the first few years of treatment. After this period, the clinical response diminishes and is accompanied by adverse side effects which include dyskinesia, fluctuation in efficacy throughout the day ("on-off effect") and psychiatric symptoms such as confusional states, paranoia, and hallucinations. This decrease in the effect of L-DOPA treatment is attributed to a number of factors, including the natural progression of the disease, alteration in dopamine receptors as a consequence of increased dopamine production or increased levels of dopamine metabolites, and pharmacokinetic problems of L-DOPA absorption (reviewed by Youdim, et al., Progress in Medicinal Chemistry, 21, 138–167 (1984)).

In order to overcome the drawbacks ot L-DOPA treatment, various treatments have been devised in which L-DOPA is combined with MAO inhibitors with the aim of reducing the metabolic breakdown of newly formed dopamine (see for example, Chiese, P., U.S. Pat. No. 4,826,875, issued May 2, 1989).

MAO exists in two forms known as MAO-A and MAO-B which are selective for different substrates and inhibitors. For example, MAO-B more efficiently metabolizes substrates such as 2-phenylethylamine, and is selectively and irreversibly inhibited by (−)-deprenyl as described below.

It should be noted, however, that treatments combining L-DOPA with an inhibitor of both MAO-A and MAO-B are undesirable, as they lead to adverse side effects related to an increased level of catecholamines throughout the neuraxis. Furthermore, complete inhibition of MAO is also undesirable as it potentiates the action of sympathomimetic amines such as tyramine, leading to the so-called "cheese effect" (reviewed by Youdim et al., Handbook of Experimental Pharmacology, ed. by Trendelenburg and Weiner, Springer-Verlag, 90, ch. 3 (1988)). As MAO-B was shown to be the predominant form of MAO in the brain, selective inhibitors for this form are thus considered to be a possible tool for achieving a decrease in dopamine breakdown on the one hand, together with a minimization of the systemic effects of total MAO inhibition on the other.

Many inhibitors of MAO are chiral molecules. Although one enantiomer often shows some stereoselectivity in relative potency towards MAO-A and -B, a given enantiomeric configuration is not always more selective than its mirror image isomer in discriminating between MAO-A and MAO-B.

Table I lists the $IC_{50}$ (mmol/L) of enantiomeric pairs of propargyl amines in a rat brain preparation of MAO. These results show small differences in potency in MAO-B inhibition between the R and S enantiomers. (B. Hazelhoff, et al., Naunyn-Schmeideberg's Arch. Pharmacol., 330, 50 (1985)). Both enantiomers are selective for MAO-B. In 1967, Magyar, et al. reported that R-(−)-deprenyl is 500 times more potent than the S-(+) enantiomer in inhibiting the oxidative deamination of tyramine by rat brain homogenate. (K. Magyar, et al., Act. Physiol. Acad. Sci., Hung., 32, 377 (1967)).

In rat liver homogenate, R-deprenyl is only 15 times as potent as the S enantiomer. In other pharmacological activity assays, such as for the inhibition of tyramine uptake, deprenyl shows different stereoselectivities. The S form is in certain cases the more potent epimer. (J. Knoll and K. Magyar, Advances in Biochemical Psychopharmacology, 5, 393 (1972)).

N-Methyl-N-propargyl-1-aminotetralin (2-MPAT) is a close structural analogue of deprenyl. The absolute stereochemistry of 2-MPAT has not been assigned. However, the (+) isomer is selective for MAO-B and the (−) isomer is selective for MAO-A. The difference in potency between the 2-MPAT enantiomers is less than 5-fold. (B. Hazelhoff, et al., id.). The enantiomers of N-propargyl-1-aminotetralin (1-PAT) are also similar in activity. The lack of data in Table I showing clear structure-activity relationships between isolated (+) or (−)-2-MPAT makes it impossible to predict the absolute stereochemistry thereof.

After extensive computer modeling, Polymeropoulos recently predicted that (R)-N-methyl-N-propargyl-1-aminoindan (R-1-MPAI) would be more potent than (S) as a MAO-B inhibitor. (E. Polymeropoulos, Inhibitors of Monoamine Oxidase B, I. Szelenyi, ed., Birkhauser Verlag, p. 110 (1993)). However, experiments described show that R-1-MPAI is a slightly more potent inhibitor of MAO-B than S-1-MPAI, but is an even more potent inhibitor of MAO-A. Both the selectivity between MAO-A and -B and the relative potency of the R and S epimers are low. Thus, contrary to expectations in the art, 1-MPAI is useless as a pharmaceutical agent.

The data presented below demonstrate that high selectivity for MAO of one enantiomer versus the other cannot be predicted. The structure of the MAO active site is not well enough understood to permit the prediction of the relative potency or selectivity of any given compound or pair or enantiomers thereof.

III.

Brain stroke is the third leading cause of death in the developed countries. Survivors often suffer from neurological and motor disabilities. The majority of CNS strokes are regarded as localized tissue anemia following obstruction of arterial blood flow which causes oxygen and glucose deprivation. Occlusion of the middle cerebral artery in the rat (MCAO) is a common experimental procedure that is assumed to represent stroke in humans. It has been proposed that the neurological lesion caused by proximal occlusion of this artery in the rat corresponds to a large focal cerebral infarct in humans (Yamori et al., 1976). This correspondence has been based on similarities between cranial circulation in the two species. Other animal models of stroke have been described by Stefanovich (1983).

The histological changes described by Tamura et al. (1981) who were the first to introduce the MCAO procedure, were commonly seen in the cortex of the frontal (100%), sensimotor (75%) and auditory (75%) areas and to a lesser extent in the occipital lobe cortex (25%). In addition, damage was observed in the lateral segment of the caudate nucleus (100%), and only to a variable extent in its medial portion (38%). Concomitantly, the following disorders were reported in MCAO animals: neurological deficits (Menzies et al., 1992), cognitive disturbances (Yamamoto et al., 1988), brain edema (Young et al., 1993; Matsui et al., 1993; Saur et al., 1993), decreased cerebral blood flow (Teasdale et al., 1983), catecholamine fluctuations. (Cechetto et al., 1989). Any of these disorders might be indicative of the severity and extent of brain damage that follow MCAO in the rat. Conversely, a drug with a potential to limit or abort a given disorder may be considered as a candidate for the treatment of stroke in humans.

TABLE IA $IC_{50}$ (mmol/L) Data for Rat Brain MAO Inhibition by Propargylamines

| COMPOUND | REF | EPIMER | INHIBITION A | B | A/B | RELATIVE POTENCY +/− A | B |
|---|---|---|---|---|---|---|---|
| 2-MPAI | a. | + | 140 | 16 | 8.8 | 3 | 0.2 |
|  |  | − | 46 | 88 | 0.5 |  |  |
|  |  |  |  |  | R/S |  |  |
| DEPRENYL | a. | S | 3600 | 16 | 120 | 80 | 2.6 |
|  |  | R | 450 | 6 | 75 |  |  |

TABLE IA-continued $IC_{50}$ (mmol/L) Data for Rat Brain MAO Inhibition by Propargylamines

| COMPOUND | REF | EPIMER | INHIBITION A | B | A/B | RELATIVE POTENCY +/− A | B |
|---|---|---|---|---|---|---|---|
| 1-MPAI | b. | S | 70 | 50 | 1.4 | 23 | 5 |
|  |  | R | 3 | 10 | 0.3 |  |  |
| 1-PAT | c. | S | 3800 | 50 | 76 | 4 | 0.5 |
|  |  | R | 900 | 90 | 10 |  |  | a. B. Hazelhoff, et al., Naunyn-Schmeideberg's Arch. Pharmacol., 330, 50 (1985).
b. European Patent Application 436,492 A2, published July 10, 1991.
c. Present inventors.

One selective MAO-B inhibitor, (−)-deprenyl, has been extensively studied and used as a MAO-B inhibitor to augment L-DOPA treatment. This treatment with (−)-deprenyl is generally favorable and does not cause the "cheese effect" at doses causing nearly complete inhibition of MAO-B (Elsworth, et al., Psychopharmacology, 57, 33 (1978)). Furthermore, the addition of (−)-deprenyl to a combination of L-DOPA and a decarboxylase inhibitor administered to Parkinsons's patients leads to improvements in akinesia and overall functional capacity, as well as the elimination of "on-off" type fluctuations (reviewed by Birkmayer & Riederer in "Parkinson's Disease," Springer-Verlag, pp. 138–149 (1983)). Thus, (−)-deprenyl (a) enhances and prolongs the effect of L-DOPA, and (b) does not increase the adverse effects of L-DOPA treatment.

However, (−)-deprenyl is not without its own adverse sides effects, which include activation of pre-existing gastric ulcers and occasional hypertensive episodes. Furthermore, (−)-deprenyl is an amphetamine derivative and is metabolized to amphetamine and methamphetamines, which substances may lead to undesirable side effects such as increased heart rate (Simpson, Biochemical Pharmacology, 27, 1951 (1978); Finberg, et al., in "Monoamine Oxidase Inhibitors—The State of the Art," Youdim and Paykel, eds., Wiley, pp. 31–43 (1981)).

Other compounds have been described that are selective irreversible inhibitors of MAO-B but which are free of the undesirable effects associated with (−)-deprenyl. One such compound, namely N-propargyl-1-aminoindan.HCl (racemic PAI.HCl), was described in GB 1,003,686 and GB 1,037,014 and U.S. Pat. No. 3,513,244, issued May 19, 1970. Racemic PAI.HCl is a potent, selective, irreversible inhibitor of MAO-B, is not metabolized to amphetamines, and does not give rise to unwanted sympathomimetic effects.

In comparative animal tests, racemic PAI was shown to have considerable advantages over (−)-deprenyl. For example, racemic PAI produces no significant tachycardia, does not increase blood pressure (effects produced by doses of 5 mg/kg of (−)-deprenyl), and does not lead to contraction of nictitating membrane or to an increase in heart rate at doses of up to 5 mg/kg (effects caused by (−)-deprenyl at doses over 0.5 mg/kg). Furthermore, racemic PAI.HCl does not potentiate the cardiovascular effects of tyramine (Finberg, et al., in "Enzymes and Neurotransmitters in Mental Disease," pp. 205–219 (1980), Usdin, et al., Eds., Wiley, N.Y.; Finberg, et al. (1981), in "Monoamine Oxidase Inhibitors—The State of the Art," ibid.; Finberg and Youdim, British Journal Pharmacol., 85, 451 (1985)).

One underlying object of this invention was to separate the racemic PAI compounds and to obtain an enantiomer with MAO-B inhibition activity which would be free of any undesirable side effects associated with the other enantiomer.

Since deprenyl has a similar structure to PAI and it is known that the (−)-enantiomer of deprenyl, i.e. (−)-deprenyl, is considerably more pharmaceutically active than the (+)-enantiomer, the (−) enantiomer of PAI would be expected to be the more active MAO-B inhibitor.

However, contrary to such expectations, upon resolution of the enantiomers, it was found that the (+)-PAI enantiomer is in fact the active MAO-B inhibitor while the (−)-enantiomer shows extremely low MAO-B inhibitory activity. Furthermore, the (+)-PAI enantiomer also has a degree of selectivity for MAO-B inhibition surprisingly higher than that of the corresponding racemic form, and should thus have fewer undesirable side effects in the treatment of the indicated diseases than would the racemic mixture. These findings are based on both in vitro and in vivo experiments as discussed in greater detail infra.

It was subsequently shown that (+)-PAI has the R absolute configuration. This finding was also surprising based on the expected structural similarity of (+)-PAI analogy with deprenyl and the amphetamines.

The high degree of stereoselectivity of pharmacological activity between R(+)-PAI and the S(−) enantiomer as discussed hereinbelow is also remarkable. The compound R(+)-PAI is nearly tour orders of magnitude more active than the S(−) enantiomer in MAO-B inhibition. This ratio is significantly higher than that observed between the two deprenyl enantiomers (Knoll and Magyar, Adv. Biochem. Psychopharmacol., 5, 393 (1972); Magyar, et al., Acta Physiol. Acad. Sci. Hung., 32, 377 (1967)). Furthermore, in some physiological tests, (+)-deprenyl was reported to have activity equal to or even higher than that of the (−) enantiomer (Tekes, et al., Pol. J. Pharmacol. Pharm., 40, 653 (1988)).

MPAI is a more potent inhibitor of MAO activity, but with lower selectivity for MAO-B over A (Tipton, et al., Biochem. Pharmacol., 31, 1250 (1982)). As only a small degree of difference in the relative activities of the two resolved enantiomers was surprisingly observed with MPAI, the remarkable behavior of R(+)PAI is further emphasized (See Table 1B).

The subject invention also provides methods of using the pharmaceutically active PAI-enantiomer alone (without L-DOPA) for treatment of Parkinson's disease, a memory disorder, dementia, depression, hyperactive syndrome, an affective illness, a neurodegenerative disease, a neurotoxic injury, brain ischemia, a head trauma injury, a spinal trauma injury, schizophrenia, an attention deficit disorder, multiple sclerosis, or withdrawal symptoms (see review by Youdim, et al., in Handbook of Experimental Pharmacology, Trendelenberg and Wiener, eds., 90/I, ch. 3 (1988)).

The subject invention further provides a method of using the pharmaceutically active PAI-enantiomer alone for pretreatment of Parkinson's disease. The subject invention also provides pharmaceutical compositions comprising R(+)PAI and synergistic agents such as levodopa. The use of such agents has been studied with respect to (−)-deprenyl which was shown to be effective when administered alone to early Parkinson's patients, and may also have a synergistic effect in these patients when administered together with α-tocopherol, a vitamin E derivative (The Parkinson's Study Group, New England J. Med., 321(20), 1364–1371 (1989)).

In addition to its usefulness in treating Parkinson's disease, (−)-deprenyl has also been shown to be useful in the treatment of patients with dementia of the Alzheimer type (DAT) (Tariot, et al., Psychopharmacology, 91, 489–495 (1987)), and in the treatment of depression (Mendelewicz and Youdim, Brit. J. Psychiat. 142, 508–511 (1983)). The R(+)PAI compound of this invention, and particularly the mesylate salt thereof, has been shown to restore memory. R(+)PAI thus has potential for the treatment of memory disorders, dementia, especially of the Alzheimer's type, and hyperactive syndrome in children.

Finally, the subject invention provides highly stable salts of R(+)PAI with superior pharmaceutical properties. The mesylate salt is especially stable, shows unexpectedly greater selectivity, and shows significantly fewer side effects than do the corresponding racemic salts.

SUMMARY OF THE INVENTION

The subject invention provides R(+)-N-propargyl-1-aminoindan having the structure:

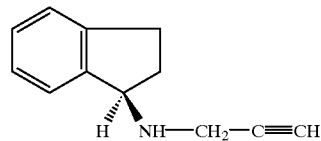

The subject invention further provides a pharmaceutically acceptable salt of R(+)-N-propargyl-1-aminoindan.

The subject invention further provides a pharmaceutical composition which comprises a therapeutically effective amount of R(+)-N-propargyl-1-aminoindan or a pharmaceutically acceptable salt thereof and a pharmaceutically acceptable carrier.

The subject invention further provides a method of treating a subject afflicted with Parkinson's disease which comprises administering to the subject an amount of R(+)-N-propargyl-1-aminoindan or the pharmaceutically acceptable salt thereof of the subject invention effective to treat Parkinson's disease in the subject.

The subject invention further provides a method of treating a subject afflicted with a memory disorder which comprises administering to the subject an amount of R(+)-N-propargyl-1-aminoindan or the pharmaceutically acceptable salt thereof of the subject invention effective to treat the memory disorder in the subject.

The subject invention further provides a method of treating a subject afflicted with dementia which comprises administering to the subject an amount of R(+)-N-propargyl-1-aminoindan or the pharmaceutically acceptable salt thereof of the subject invention effective to treat dementia in the subject. In one embodiment, the dementia is of the Alzheimer type (DAT).

The subject invention further provides a method of treating a subject afflicted with depression which comprises administering to the subject an amount of R(+)-N-propargyl-1-aminoindan or the pharmaceutically acceptable salt thereof of the subject invention effective to treat depression in the subject.

The subject invention further provides a method of treating a subject afflicted with hyperactive syndrome which comprises administering to the subject an amount of R(+)-N-propargyl-1-aminoindan or the pharmaceutically acceptable salt thereof of the subject invention effective to treat hyperactive syndrome in the subject.

The subject invention further provides a method of treating a subject afflicted with an affective illness which comprises administering to the subject an amount of R(+)-N-propargyl-1-aminoindan or the pharmaceutically acceptable salt thereof of the subject invention effective to treat the affective illness in the subject.

The subject invention further provides a method of treating a subject afflicted with a neurodegenerative disease which comprises administering to the subject an amount of R(+)-N-propargyl-1-aminoindan or the pharmaceutically acceptable salt thereof of the subject invention effective to treat the neurodegenerative disease in the subject.

The subject invention further provides a method of treating a subject afflicted with a neurotoxic injury which comprises administering to the subject an amount of R(+)-N-propargyl-1-aminoindan or the pharmaceutically acceptable salt thereof of the subject invention effective to treat the neurotoxic injury in the subject.

The subject invention further provides a method of treating a subject afflicted with brain ischemia which comprises administering to the subject an amount of R(+)-N-propargyl-1-aminoindan or the pharmaceutically acceptable salt thereof of the subject invention effective to treat brain ischemia in the subject.

The subject invention further provides a method of treating a subject afflicted with a head trauma injury which comprises administering to the subject an amount of R(+)-N-propargyl-1-aminoindan or the pharmaceutically acceptable salt thereof of the subject invention effective to treat the head trauma injury in the subject.

The subject invention further provides a method of treating a subject afflicted with a spinal trauma injury which comprises administering to the subject an amount of R(+)-N-propargyl-1-aminoindan or the pharmaceutically acceptable salt thereof of the subject invention effective to treat the spinal trauma injury in the subject.

The subject invention further provides a method of treating a subject afflicted with schizophrenia which comprises administering to the subject an amount of R(+)-N-propargyl-1-aminoindan or the pharmaceutically acceptable salt thereof of the subject invention effective to treat schizophrenia in the subject.

The subject invention further provides a method of treating a subject afflicted with an attention deficit disorder which comprises administering to the subject an amount of R(+)-N-propargyl-1-aminoindan or the pharmaceutically acceptable salt thereof of the subject invention effective to treat the attention deficit disorder in the subject.

The subject invention further provides a method of treating a subject afflicted with multiple sclerosis which comprises administering to the subject an amount of R(+)-N-propargyl-1-aminoindan or the pharmaceutically acceptable salt thereof of the subject invention effective to treat multiple sclerosis in the subject.

The subject invention further provides a method of preventing nerve damage in a subject which comprises administering to the subject an amount of R(+)-N-propargyl-1-aminoindan or the pharmaceutically acceptable salt thereof of the subject invention effective to prevent nerve damage in the subject.

The subject invention further provides a method of treating a subject suffering from symptoms of withdrawal from an addictive substance which comprises administering to the subject an amount of R(+)-N-propargyl-1-aminoindan or the pharmaceutically acceptable salt thereof of the subject invention effective to treat the symptoms of withdrawal in the subject.

The subject invention further provides a method for preparing R(+)-N-propargyl-1-aminoindan which comprises contacting, in the presence of an organic or inorganic base, R(−)-aminoindan with either propargyl bromide or propargyl chloride so as to form R(+)-N-propargyl-1-aminoindan, and isolating the R(+)-N-propargyl-1-aminoindan formed thereby.

The subject invention further provides a method for preparing racemic N-propargyl-1-aminoindan which comprises contacting, in the presence of an organic or inorganic base, racemic 1-aminoindan with propargyl bromide or propargyl chloride so as to form racemic N-propargyl-1-aminoindan, and isolating the racemic N-propargyl-1-aminoindan formed thereby.

Finally, the subject invention provides a method of preparing an R(+)-N-propargyl-1-aminoindan salt which comprises contacting racemic N-propargyl-1-aminoindan with an optically active acid so as to form two diastereomeric N-propargyl-1-aminoindan salts, and isolating R(+)-N-propargyl-1-aminoindan salt from the diastereomeric N-propargyl-1-aminoindan salts so formed.

BRIEF DESCRIPTION OF THE FIGURES

FIG. 4 is a graphic representation of the results according to Example 23 showing acute inhibition (i.p.) of MAO-A in brain.

FIG. 5 is a graphic representation of the results according to Example 23 showing acute inhibition (i.p.) of MAO-B in brain.

DETAILED DESCRIPTION OF THE INVENTION

Figure 1:
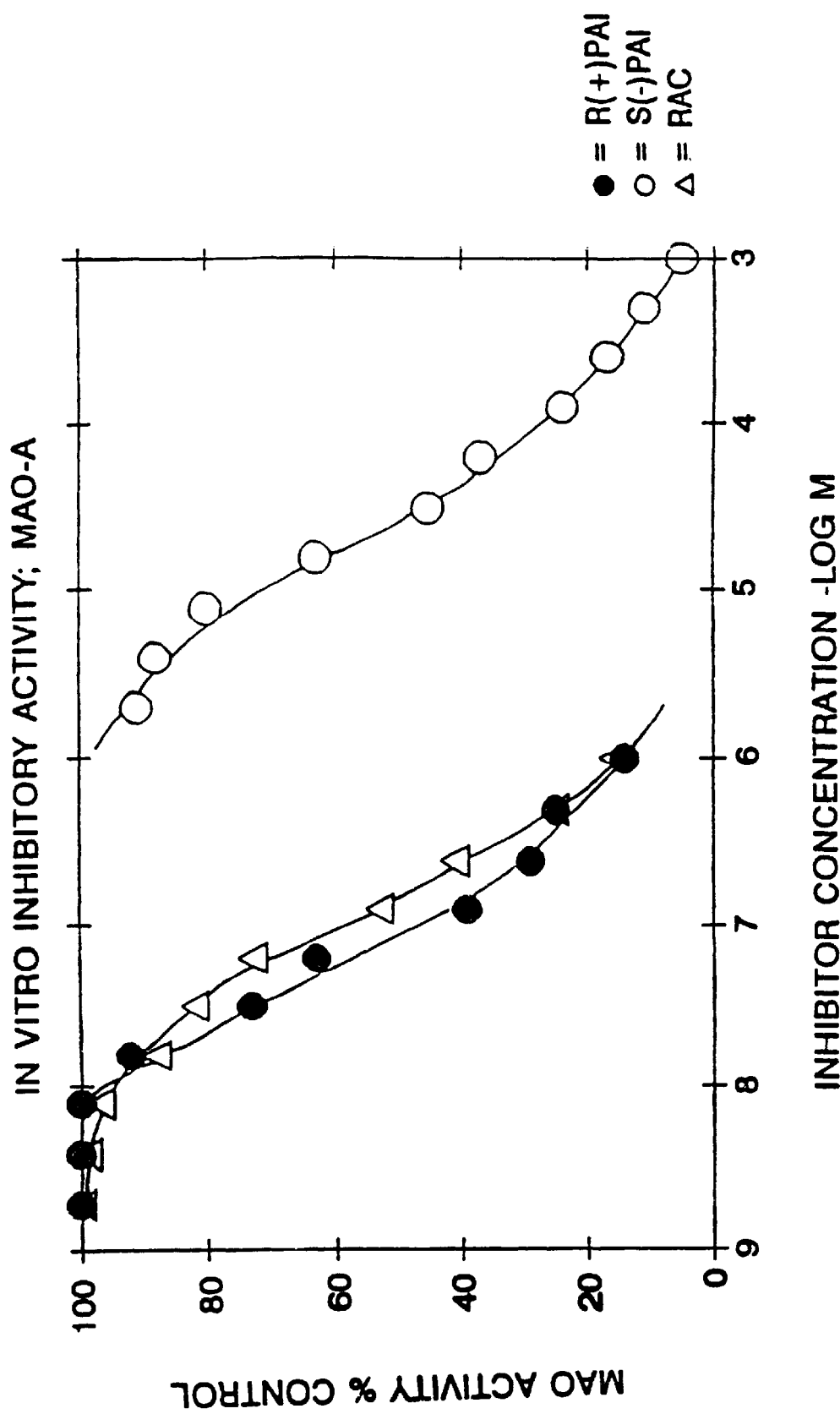
FIG. 1 is a graphic representation of the results according to Example 22 showing in vitro MAO-A inhibitory activity.

The subject invention provides R(+)-N-propargyl-1-aminoindan having the structure:

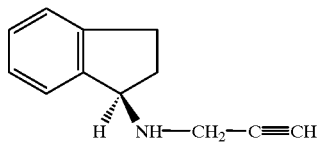

As demonstrated in the Experimental Examples hereinbelow, R(+)PAI is nearly 7,000 times more active as an inhibitor of MAO-B than is S(-)PAI. In view of known MAO-B inhibitors in the art which possess low selectivity between MAO-A and MAO-B, and which do not show predictable trends in potency as a function of R or S configuration, the selectivity of R(+)PAI is unexpected.

R(+)PAI may be obtained by optical resolution of racemic mixtures of R- and S-enantiomers of PAI. Such a resolution can be accomplished by any conventional resolution method well known to a person skilled in the art, such as those described in J. Jacques, A. Collet and S. Wilen, "Enantiomers, Racemates and Resolutions," Wiley, N.Y. (1981). For example, the resolution may be carried out by preparative chromatography on a chiral column. Another example of a suitable resolution method is the formation of diastereomeric salts with a chiral acid such as tartaric, malic, mandelic acid or N-acetyl derivatives of amino acids, such as N-acetyl leucine, followed by recrystallisation to isolate the diastereomeric salt of the desired R enantiomer.

The racemic mixture of R and S enantiomers of PAI may be prepared, for example, as described in GB 1,003,676 and GB 1,037,014. The racemic mixture of PAI can also be prepared by reacting 1-chloroindan with propargylamine. Alternatively, this racemate may be prepared by reacting propargylamine with 1-indanone to form the corresponding imine, followed by reduction of the carbon-nitrogen double bond of the imine with a suitable agent, such as sodium borohydride.

In accordance with this invention, the R enantiomer of PAI can also be prepared directly from the optically active R-enantiomer of 1-aminoindan by reaction with propargyl bromide or propargyl chloride in the presence of an organic or inorganic base, and optionally in the presence of a suitable solvent.

Suitable organic or inorganic bases for use in the above reaction include, by way of example, triethylamine, pyridine, alkali metal carbonates, and bicarbonates. If the reaction is conducted in the presence of a solvent, the solvent may be chosen from, e.g., toluene, methylene chloride, and acetonitrile. One method of preparing R(+)PAI is to react R-1-aminoindan with propargyl chloride using potassium bicarbonate as a base and acetonitrile as solvent.

The above-described reaction of 1-aminoindan generally results in a mixture of unreacted primary amine, the desired secondary amine and the tertiary amine N,N-bispropargylamino product. The desired secondary amine, i.e., N-propargyl-1-aminoindan, can be separated from this mixture by a conventional separation method including, by way of example, chromatography, distillation and selective extraction.

The R-1-aminoindan starting material can be prepared by methods known in the art which include, by way of example, the method of Lawson and Rao, Biochemistry, 19, 2133 (1980), methods in references cited therein, and the method of European Patent No. 235,590.

R-1-aminoindan can also be prepared by resolution of a racemic mixture of the R and S enantiomers, which involves, for example, the formation of diastereomeric salts with chiral acids, or any other known method such as those reported in J. Jacques, et al., ibid. Alternatively, R-1-aminoindan may be prepared by reacting 1-indanone with an optically active amine, followed by reduction of the carbon nitrogen double bond of the resulting imine by hydrogenation over a suitable catalyst, such as palladium on carbon, platinum oxide or Raney nickel. Suitable optically active amines include, for example, one of the antipodes of phenethylamine or an ester of an amino acid, such as valine or phenylalanine. The benzylic N—C bond may be cleaved subsequently by hydrogenation under non-vigorous conditions.

An additional method for preparing R-1-aminoindan is the hydrogenation of indan-1-one oxime ethers as described above, wherein the alkyl portion of the ether contains an optically pure chiral center. Alternatively, a non-chiral derivative of indan-1-one containing a carbon-nitrogen double bond, such as an imine or oxime, can be reduced with a chiral reducing agent, e.g., a complex of lithium aluminum-hydride and ephedrine.

The subject invention further provides a pharmaceutically acceptable salt of R(+)-N-propargyl-1-aminoindan.

In the practice of this invention, pharmaceutically acceptable salts include, but are not limited to, the mesylate, maleate, fumarate, tartrate, hydrochloride, hydrobromide, esylate, p-toluenesulfonate, benzoate, acetate, phosphate and sulfate salts.

In one embodiment, the salt is selected from the group consisting of the mesylate salt of R(+)-N-propargyl-1-aminoindan, the esylate salt of R(+)-N-propargyl-1-aminoindan, and the sulfate salt of R(+)-N-propargyl-1-aminoindan.

As demonstrated in the Experimental Examples hereinbelow, the mesylate salt is highly stable to thermal degradation, and shows unexpectedly superior selectivity for MAO-B over the racemic salt.

For the preparation of pharmaceutically acceptable acid addition salts of the compound of R(+)PAI, the free base can be reacted with the desired acids in the presence of a suitable solvent by conventional methods. Similarly, an acid addition salt may be converted to the free base form in a known manner.

A preferred mode of preparing the mesylate salt of (R)-PAI comprises (a) adding an aqueous solution of 15% sodium hydroxide to a solution of propargyl benzene-sulfonate (or tosylate or mesylate) in toluene; (b) stirring for 5 hours; (c) adding additional toluene and water; (d) separating and washing the organic phase with 10% sodium hydroxide, and then diluting with water; (e) adjusting the pH of the mixture to 3.2 by adding 10% aqueous sulfuric acid; (f) separating the aqueous phase and adjusting the pH to 7.3 with 10 sodium hydroxide; (g) extracting three times with toluene while maintaining constant pH; (h) concentrating combined organic layers in vacuo to give a yellow oil; (i) dissolving the oil and L-tartaric acid in isopropanol; (j) heating to reflux for 1 hour; (k) cooling to room temperature and collecting the precipitate by filtration; (l) recrystallizing the crude di-propargylaminoindan tartrate from methanol/isopropanol (1:1) to give di(R(+)-N-propargyl-1-aminoindan) tartrate; (m) dissolving the tartrate salt and methanesulfonic acid in isopropanol, and heating to reflux for 30 minutes; and (n) cooling to room temperature, and collecting the precipitated R(+)-N-propargyl-1-aminoindan.

The subject invention further provides a pharmaceutical composition which comprises a therapeutically effective amount of R(+)-N-propargyl-1-aminoindan or a pharmaceutically acceptable salt thereof and a pharmaceutically acceptable carrier. The "therapeutically effective amount" of the R(+)-N-propargyl-1-aminoindan or pharmaceutically acceptable salt thereof may be determined according to methods well known to those skilled in the art.

Possible salts useful for such compositions include hydrochloride, phosphate, maleate, fumarate, tartrate, mesylate, esylate, and sulfate salts.

These compositions may be prepared as medicaments to be administered orally, parenterally, rectally, or transdermally.

In one embodiment, the pharmaceutically acceptable carrier is a solid and the pharmaceutical composition is a tablet.

The therapeutically effective amount may be an amount from about 0.1 mg to about 100 mg. The therapeutically effective amount may also be an amount from about 1 mg to about 10 mg.

Suitable forms for oral administration include tablets, compressed or coated pills, dragees, sachets, hard or soft gelatin capsules, sublingual tablets, syrups and suspensions.

In an alternative embodiment, the pharmaceutically acceptable carrier is a liquid and the pharmaceutical composition is an injectable solution. The therapeutically effective amount may be an amount from about 0.1 mg/ml to about 100 mg/ml. The therapeutically effective amount may also be an amount from about 1 mg/ml to about 10 mg/ml. In one embodiment, the dose administered is an amount between 0.5 ml and 1.0 ml.

In a further alternative embodiment, the carrier is a gel and the pharmaceutical composition is a suppository.

For parenteral administration the invention provides ampoules or vials that include an aqueous or non-aqueous solution or emulsion. For rectal administration there are provided suppositories with hydrophilic or hydrophobic vehicles. For topical application as ointments and transdermal delivery there are provided suitable delivery systems as known in the art.

In the preferred embodiment, the pharmaceutically acceptable salt is a mesylate salt.

These compositions may be used alone to treat the above-listed disorders, or alternatively, as in the case of Parkinson's disease, for example, they may be used as an adjunct to the conventional L-DOPA treatments.

The preferred dosages of the active ingredient, i.e., R-PAI, in the above compositions are within the following ranges. For oral or suppository formulations, 0.1–100 mg per dosage unit may be taken daily, and preferably 1–10 mg per dosage unit is taken daily. For injectable formulations, 0.1–100 mg/ml per dosage unit may be taken daily, and preferably 1–10 mg/ml per dosage unit is taken daily.

In one embodiment, the pharmaceutical composition further comprises a therapeutically effective amount of Levodopa. In another embodiment, the pharmaceutical composition still further comprises an effective amount of a decarboxylase inhibitor.

The amount of decarboxylase inhibitor administered in combination with (R)-PAI or a pharmaceutically acceptable salt thereof is an amount effective to ensure L-DOPA uptake in the subject.

The decarboxylase inhibitor may be L-Carbidopa. In one embodiment, the therapeutically effective amount of R(+)-N-propargyl-1-aminoindan is about 0.1 mg to about 100 mg, the therapeutically effective amount of Levodopa is about 50 mg to about 250 mg, and the effective amount of L-Carbidopa is about 10 mg to about 25 mg.

The decarboxylase inhibitor may also be benserazide. In one embodiment, the therapeutically effective amount of R(+)-N-propargyl-1-aminoindan is about 0.1 mg to about 100 mg, the therapeutically effective amount of Levodopa is about 50 mg to about 200 mg, and the effective amount of benserazide is about 12.5 mg to about 50 mg.

The subject invention further provides a method of treating a subject afflicted with Parkinson's disease which comprises administering to the subject an amount of R(+)-N-propargyl-1-aminoindan or the pharmaceutically acceptable salt thereof of the subject invention effective to treat Parkinson's disease in the subject.

Methods of treatment of Parkinson's disease which combine the use of (R)-PAI with other drugs, such as dopamine agonists, bromocryptine, pergolide, lisuride, as well as catecholamine oxidase methyl transferase inhibitors are within the scope of the subject invention.

In the preferred embodiment, the pharmaceutically acceptable salt is a mesylate salt.

The administering may comprise orally administering, rectally administering, transdermally administering, or parenterally administering.

In one embodiment, the method of the subject invention further comprises administering to the subject a therapeutically effective amount of Levodopa. In another embodiment, the method of the subject invention still further comprises administering to the subject an effective amount of a decarboxylase inhibitor.

The decarboxylase inhibitor may be L-Carbidopa. Alternatively, the decarboxylase inhibitor may be benserazide.

The subject invention further provides a method of treating a subject afflicted with a memory disorder which comprises administering to the subject an amount of R(+)-N-propargyl-1-aminoindan or the pharmaceutically acceptable salt thereof of the subject invention effective to treat the memory disorder in the subject.

The subject invention further provides a method of treating a subject afflicted with dementia which comprises administering to the subject an amount of R(+)-N-propargyl-1-aminoindan or the pharmaceutically acceptable salt thereof of the subject invention effective to treat dementia in the subject. In one embodiment, the dementia is of the Alzheimer type (DAT).

The subject invention further provides a method of treating a subject afflicted with depression which comprises administering to the subject an amount of R(+)-N-propargyl-1-aminoindan or the pharmaceutically acceptable salt thereof of the subject invention effective to treat depression in the subject.

The subject invention further provides a method of treating a subject afflicted with hyperactive syndrome which comprises administering to the subject an amount of R(+)-N-propargyl-1-aminoindan or the pharmaceutically acceptable salt thereof of the subject invention effective to treat hyperactive syndrome in the subject.

The administering may comprise orally administering, rectally administering, or parenterally administering.

The subject invention further provides a method of treating a subject afflicted with an affective illness which comprises administering to the subject an amount of R(+)-N-propargyl-1-aminoindan or the pharmaceutically acceptable salt thereof of the subject invention effective to treat the affective illness in the subject.

The subject invention further provides a method of treating a subject afflicted with a neurodegenerative disease which comprises administering to the subject an amount of R(+)-N-propargyl-1-aminoindan or the pharmaceutically acceptable salt thereof of the subject invention effective to treat the neurodegenerative disease in the subject.

The subject invention further provides a method of treating a subject afflicted with a neurotoxic injury which comprises administering to the subject an amount of R(+)-N-propargyl-1-aminoindan or the pharmaceutically acceptable salt thereof of the subject invention effective to treat the neurotoxic injury in the subject.

The subject invention further provides a method of treating a subject afflicted with brain ischemia which comprises administering to the subject an amount of R(+)-N-propargyl-1-aminoindan or the pharmaceutically acceptable salt thereof of the subject invention effective to treat brain ischemia in the subject.

This invention provides a method of treating brain ischemia or stroke in a subject which comprises administering to the subject an amount of R(+)-N-propargyl-1-aminoindan or a pharmaceutically acceptable salt thereof effective to treat brain ischemia or stroke in the subject.

In an embodiment of the method for treatment of brain ischemia or stroke, the pharmaceutically acceptable salt of R(+)-N-propargyl-1-aminoindan is selected from the group consisting of: the mesylate salt; the ethylsulfonate salt; the sulfate salt; and the hydrochloride salt. Preferably, the pharmaceutically acceptable salt is the mesylate salt of R(+)-N-propargyl-1-aminoindan.

The effective amount can be determined using techniques known to those of skill in the art, such as titration. In an embodiment of this invention, the effective amount is from about 0.5 milligrams per kilogram body weight of the subject to about 2.5 milligrams per kilogram body weight of the subject. The R(+)-N-propargyl-1-aminoindan or pharmaceutically acceptable salt thereof is administered using techniques known to those of skill in the art. For example, it may be administered intravenously, orally, rectally, transdermally, or parenterally.

The subject is preferably a mammal, such as a dog, cat, mouse, rat, rabbit, pig, horse, goat, sheep, cow, ape or monkey. In a particular embodiment the subject is human.

In an embodiment of this invention, the effective amount is from about 0.01 mg to 50.0 mg per day. In a more specific embodiment, the effective amount is from 0.1 to 10.0 mg per day.

In one embodiment of the above-described method, the area of the brain ischemia is reduced by about thirty-five percent.

The subject invention further provides a method of treating a subject afflicted with a head trauma injury which comprises administering to the subject an amount of R(+)-N-propargyl-1-aminoindan or the pharmaceutically acceptable salt thereof of the subject invention effective to treat the head trauma injury in the subject.

The subject invention further provides a method of treating a subject afflicted with a spinal trauma injury which comprises administering to the subject an amount of R(+)-N-propargyl-1-aminoindan or the pharmaceutically acceptable salt thereof of the subject invention effective to treat the spinal trauma injury in the subject.

This invention further provides a method of treating neurotrauma in a subject which comprises administering to the subject an amount of R(+)-N-propargyl-1-aminoindan or a pharmaceutically acceptable salt thereof effective to treat neurotrauma in the subject.

In the treatment of head trauma injury, spinal trauma injury or neurotrauma, the pharmaceutically acceptable salt of R(+)-N-propargyl-1-aminoindan is selected from the group consisting of: the mesylate salt; the ethylsulfonate salt; the sulfate salt; and the hydrochloride salt. Preferably, the pharmaceutically acceptable salt is the mesylate salt of R(+)-N-propargyl-1-aminoindan.

The effective amount can be determined using techniques known to those of skill in the art, such as titration. In an embodiment of this invention, the effective amount is from about 0.5 milligrams per kilogram body weight of the subject to about 2.5 milligrams per kilogram body weight of the subject. The R(+)-N-propargyl-1-aminoindan or pharmaceutically acceptable salt thereof is administered using techniques known to those of skill in the art. For example, it may be administered intravenously, orally, rectally, transdermally, or parenterally.

The subject is preferably a mammal, such as a dog, cat, mouse, rat, rabbit, pig, horse, goat, sheep, cow, ape or monkey. In a particular embodiment the subject is human.

In an embodiment of this invention, the effective amount is from about 0.01 mg to 50.0 mg per day. In a more specific embodiment, the effective amount is from 0.1 to 10.0 mg per day.

The subject invention further provides a method of treating a subject afflicted with schizophrenia which comprises administering to the subject an amount of R(+)-N-propargyl-1-aminoindan or the pharmaceutically acceptable salt thereof of the subject invention effective to treat schizophrenia in the subject.

The subject invention further provides a method of treating a subject afflicted with an attention deficit disorder which comprises administering to the subject an amount of R(+)-N-propargyl-1-aminoindan or the pharmaceutically acceptable salt thereof of the subject invention effective to treat the attention deficit disorder in the subject.

The subject invention further provides a method of treating a subject afflicted with multiple sclerosis which comprises administering to the subject an amount of R(+)-N-propargyl-1-aminoindan or the pharmaceutically acceptable salt thereof of the subject invention effective to treat multiple sclerosis in the subject.

The subject invention further provides a method of preventing nerve damage in a subject which comprises administering to the subject an amount of R(+)-N-propargyl-1-aminoindan or the pharmaceutically acceptable salt thereof of the subject invention effective to prevent nerve damage in the subject.

In one embodiment, the nerve damage is structural nerve damage. In another embodiment, the structural nerve damage is optic nerve damage.

The subject invention further provides a method of treating a subject suffering from symptoms of withdrawal from an addictive substance which comprises administering to the subject an amount of R(+)-N-propargyl-1-aminoindan or the pharmaceutically acceptable salt thereof of the subject invention effective to treat the symptoms of withdrawal in the subject.

As used herein, the term "symptoms of withdrawal", refers to physical and/or psychological symptoms, including drug craving, depression, irritability, anergia, amotivation, appetite change, nausea, shaking and sleep irregularity.

As used herein, the term "addictive substance", includes, by way of example, (a) addictive opiates such as opium, heroin and morphine, (b) psychostimulants such as cocaine, amphetamines and methamphetamines, (c) alcohol, (d) nicotine, (e) barbiturates and (f) narcotics such as fentanyl, codeine, diphenoxylate and thebaine.

In one embodiment, the addictive substance is cocaine. In another embodiment, the addictive substance is alcohol.

The subject invention further provides a method for preparing R(+)-N-propargyl-1-aminoindan which comprises contacting, in the presence of an organic or inorganic base, R(−)-aminoindan with either propargyl bromide or propargyl chloride so as to form R(+)-N-propargyl-1-aminoindan, and isolating the R(+)-N-propargyl-1-aminoindan formed thereby.

The subject invention further provides a method for preparing racemic N-propargyl-1-aminoindan which comprises contacting, in the presence of an organic or inorganic base, racemic 1-aminoindan with propargyl bromide or propargyl chloride so as to form racemic N-propargyl-1-aminoindan, and isolating the racemic N-propargyl-1-aminoindan formed thereby.

Finally, the subject invention provides a method of preparing an R(+)-N-propargyl-1-aminoindan salt which comprises contacting racemic N-propargyl-1-aminoindan with an optically active acid so as to form two diastereomeric N-propargyl-1-aminoindan salts, and isolating R(+)-N-propargyl-1-aminoindan salt from the diastereomeric N-propargyl-1-aminoindan salts so formed.

In one embodiment, the isolating comprises isolating by fractional crystallization.

The following Experimental Details are set forth to aid in an understanding of the invention, and are not intended, and should not be construed, to limit in any way the invention set forth in the claims which follow thereafter.

EXPERIMENTAL DETAILS

Example 1

Racemic N-propargyl-1-aminoindan hydrochloride 10.0 g of racemic 1-aminoindan and 10.4 g of potassium carbonate were added to 75 ml of acetonitrile. The resulting suspension was heated to 60° C. and 4.5 g of propargyl chloride was added dropwise.

The mixture was stirred at 60° C. for 16 hours, whereafter most of the volatiles were removed by distillation in vacuo. The residue was partitioned between 10% aqueous sodium hydroxide and methylene chloride.

The organic phase was dried and the solvent removed by distillation. The residue was flash chromatographed on silica gel, eluting with 40% ethyl acetate/60% hexane. The fractions containing the title compound as a free base were combined and the eluant replaced by ether. The ethereal solution was treated with gaseous HCl the precipitate formed was isolated by suction filtration and recrystallized from isopropanol to yield 7.3 g of the title compound, m.p. 182–4° C.

Chromatographic and spectroscopic data were in accordance with U.S. Pat. No. 3,513,244, issued May 19, 1970, and an authentic sample, and were as follows: NMR $\delta(CDCl_3)$: 2.45 (2H, m), 2.60 (1H, t), 2.90 (1H, m), 3.45 (1H, m), 3.70 (2H, d), 4.95 (1H, t), 7.5 (4H, m) ppm.

Example 2

S-(−)-N-Propargyl-1-aminoindan hydrochloride

The title compound in free base form was isolated by resolving the racemic mixture of the free base of Example 1 on a Chiracel OJ (cellulose tris [p-methylbenzoate]) preparative HPLC column eluting with 10% isopropanol/90% hexane and collecting the first eluted major peak. The resulting oil was converted to the title compound (hydrochloride) by treatment of a 10% diethyl ether solution of the oil with gaseous HCl, and the resulting precipitate was collected by suction filtration. $[a]_D$ −29.2° (1%, ethanol), m.p. 182–184° C. Other chromatographic and spectroscopic properties were identical with the hydrochloride salt of Example 1.

Example 3

R-(+)-N-Propargyl-1-aminoindan hydrochloride

The title compound was prepared as in Example 2 above, except that the second eluted peak from the preparative

17

HPLC was collected: $[a]_D$+29.1° (0.8%, ethanol), m.p. 179–181° C. Other chromatographic and spectroscopic properties were identical with the hydrochloride salt of Example 1.

Example 4

R-(+)-N-Propargyl-1-aminoindan hydrochloride 12.4 g of R-(−)-1-Aminoindan and 12.9 g of potassium carbonate were added to 95 ml of acetonitrile. The resulting suspension was heated to 60° C. and 5.6 g of propargyl chloride was added dropwise. The mixture was stirred at 60° C. for 16 hours, whereafter most of the volatiles were removed by distillation in vacuo. the residue was partitioned between 10% aqueous sodium hydroxide and methylene chloride.

The organic phase was dried and the solvent removed in vacuo. The residue was flash chromatographed on silica get eluting with 40% ethyl acetate/60% hexane. Fractions containing the free base of the title compound were combined and the solvent replaced by ether. The ethereal solution was treated with gaseous HCl and the resulting precipitate was isolated by suction filtration and recrystallized from isopropanol to yield 6.8 g of the title compound, m.p. 183–185° C., $[a]_D$+30.90 (2% ethanol). Spectral properties were identical to those reported for the compound of Example 1.

Example 5

S-(−)-N-Propargyl-1-aminoindan hydrochloride

The title compound was prepared by the method of Example 4, except that S-(+)-1-aminoindan was used as starting material. The product exhibited $[a]_D$+30.90 (2% ethanol), m.p. 183–5° C. Spectral properties were identical to those reported for the compound of Example 1.

Example 6A

Di(R-(+)-N-propargyl-1-aminoindan) L-tartrate

To a solution of tartaric acid (4.4 g) in 48 ml of boiling methanol was added a solution of R-(+)-N-propargyl-1-aminoindan free base (5.0 g) in methanol (48 ml). The solution was heated to reflux and 284 ml of t-butylmethyl ether was added over 20 minutes. The mixture was heated for an additional 30 minutes, cooled, and the resulting precipitate was isolated by suction filtration to yield 6.7 g of the title compound: m.p. 175–177° C.; $[\alpha]_D$ (1.5, $H_2O$)=+34.3; Anal. calcd. for $C_{28}H_{32}O_6N_2$; C, 68.26; H, 6.56; N, 5.69. Found: C, 68.76; H, 6.57; N, 5.61.

Example 6B

R-(+)-N-propargyl-1-aminoindan mesylate a) To a solution of propargyl benzenesulfonate (78.4 g) and racemic aminoindan (63.2 g) in toluene (240 mL) at 20° C. was added dropwise an aqueous solution of 15% sodium hydroxide (108 mL). After 5 hours of stirring, additional toluene (80 mL) and water (200 mL) were added with stirring. The organic phase was separated and washed with 10% aqueous sodium hydroxide and then diluted with water. The pH of the mixture was adjusted to 3.2 by the addition of 10% aqueous sulfuric acid. The aqueous phase was separated and its pH was adjusted to 7.3 with 10% sodium hydroxide and extracted three times with toluene while maintaining constant pH. The combined organic layers were concentrated in vacuo to 40.7 g of a yellow oil.

18 b) The above crude racemic propargylaminoindan and L-tartaric acid (10 g) were dissolved in isopropanol (1 L) and heated to reflux for 1 hour. The reaction was then allowed to cool to room temperature with stirring and the precipitate collected by filtration. The crude di-propargylaminoindan tartrate was recrystallized from 1 L of 1:1 methanol/isopropanol to give di(R-(+)-N-propargyl-1-aminoindan)-L-tartrate with physical and spectral properties identical to that of the compound of Example 6A.

c) A solution of di-(R-(+)-N-propargyl-1-aminoindan) tartrate (15 g) and methanesulfonic acid (6 g) in isopropanol (150 mL) was heated to reflux for 30 minutes. The reaction was allowed to cool to room temperature and the resulting precipitate isolated by suction filtration to give the title compound (11.1 g) with m.p. 157° C. and $[\alpha]_D$=22°.

Example 7

R-(+)-N-Methyl-N-propargyl-1-aminoindan hydrochloride

The free base form of R-(+)-N-propargyl-1-aminoindan from Example 4 (1.2 grams), potassium carbonate (0.97 grams) and methyl iodide (1 gram) were added to 15 ml of acetone and the resulting suspension heated to reflux under a nitrogen atmosphere for 8 hours. Thereafter the volatiles were removed under reduced pressure and the residue partitioned between 10% aqueous sodium hydroxide (30 ml) and methylene chloride (30 ml). The organic phase was dried and the solvent removed in vacuo. The residue was flash chromatographed on silica gel eluting with 40% ethyl acetate/60% hexane. Fractions containing the title compound as a free base were combined and the solvent replaced by diethyl ether. The etheral solution was treated with gaseous HCl. The volatiles were removed in vacuo, and the residue recrystallized from isopropanol to yield 400 mg of the title compound as a white crystalline solid, m.p. 134–136° C., $[\alpha]_D$+31.40 (ethanol). NMR $\delta(CDCl_3)$: 2.55 (2H, m); 2.7 (1H, br.s); 2.8 (3H, s); 3.0 (1H, m); 3.4 (1H, m); 3.9 (2H, br.s); 5.05 (1H, m); 7.7 (4H, m) ppm.

EXAMPLE 8

S-(−)-N-Methyl-N-propargyl-1-aminoindan hydrochloride

The title compound was prepared as in Example 7 above, except that S-(−)-N-propargyl-1-aminoindan (free base) from Example 5 was used as the starting material. All of the physical and spectral properties of the title compound were identical to those in Example 7 except for the $[\alpha]_D$−34.9° C. (ethanol).

Example 9

| Tablet Composition | |
|---|---|
| N-Propargyl-1(R)-aminoindan Hydrochloride | 7.81 mg* |
| Pregelatinized starch NF | 47.0 mg |
| Lactose NF hydrous | 66.0 mg |
| Microcrystalline cellulose NF | 20.0 mg |
| Sodium starch glycolate NF | 2.99 mg |
| Talc USP | 1.5 mg |
| Magnesium stearate NF | 0.7 mg |

*Equivalent to 5.0 mg of N-propargyl aminoindan base.

Example 10

| Tablet Composition | |
|---|---|
| N-Propargyl-1(R)-aminoindan Hydrochloride | 1.56 mg* |
| Lactose hydrous | 50.0 mg |
| Pregelatinized starch | 36.0 mg |
| Microcrystalline cellulose | 14.0 mg |
| Sodium starch glycolate | 2.14 mg |
| Talc USP | 1.0 mg |
| Magnesium stearate NF | 0.5 mg |

*Equivalent to 1.0 mg of N-propargyl aminoindan base.

Example 11

| Capsule Composition | |
|---|---|
| N-Propargyl-1(R)-aminoindan Hydrochloride | 5.0 mg |
| Pregelatinized starch | 10.0 mg |
| Starch | 44.0 mg |
| Microcrystalline cellulose | 25.0 mg |
| Ethylcellulose | 1.0 mg |
| Talc | 1.5 mg |
| Purified water added as required for granulation. | |

Example 12

| Injection Composition | |
|---|---|
| N-Propargyl-1(R)-aminoindan Hydrochloride | 5.0 mg |
| Dextrose anhydrous | 44.0 mg |
| HCl added to pH 5 | |
| Purified water added as required for 1 ml | |

Example 13

| Injection Composition | |
|---|---|
| N-Propargyl-1(R)-aminoindan Hydrochloride | 1.0 mg |
| Sodium chloride | 8.9 mg |
| HCl added to pH 5 | |
| Purified water added as required for 1 ml | |

Example 14

| Injection Composition | |
|---|---|
| N-Propargyl-1(R)-aminoindan Hydrochloride | 2.0 mg |
| Sodium chloride | 8.9 mg |
| HCl added to pH 5 | |
| Purified water added as required for 1 ml | |

Example 15

| Syrup Composition | |
|---|---|
| N-Propargyl-1(R)-aminoindan Hydrochloride | 5.0 mg |
| Sucrose | 2250.0 mg |
| Saccarin sodium | 5.0 mg |
| Methylparaben | 6.0 mg |
| Propylparaben | 1.0 mg |
| Flavor | 20.0 mg |
| Glycerin USP | 500 mg |
| Alcohol 95% USP | 200 mg |
| Purified water as required to 5.0 ml | |

Example 16

| Sublingual Tablets | |
|---|---|
| N-Propargyl-1(R)-aminoindan Hydrochloride | 2.5 mg |
| Microcrystalline cellulose | 20.0 mg |
| Lactose hydrous | 5.0 mg |
| Pregelatinized starch | 3.0 mg |
| Povidone | 0.3 mg |
| Coloring agent | q.s. |
| Flavor | q.s. |
| Sweetener | q.s. |
| Talc | 0.3 mg |

Blend the excipients and the active and granulate with an ethanol solution of Providone. After drying and weighing, it is blended with the talc and compressed.

Example 17

| PAI Sublingal Tablets | |
|---|---|
| N-Propargyl-1(R)-aminoindan Hydrochloride | 5.0 mg |
| Microcrystalline cellulose | 15.0 mg |
| Pregelatinized starch | 12.0 mg |
| Ethyl cellulose | 0.3 mg |
| Talc | 0.3 mg |
| Purified water added as required for granulation. | |

Example 18

| Tablet Composition | |
|---|---|
| N-Propargyl-1(R)-aminoindan Hydrochloride | 5.0 mg |
| Levodopa | 100.0 mg |
| Carbidopa | 25.0 mg |
| Pregelatinized starch | 24.0 mg |
| Starch | 40.0 mg |
| Microcrystalline cellulose | 49.5 mg |
| Col. D & C Yellow No. 10 | 0.5 mg |
| Col. D & C Yellow No. 6 | 0.02 mg |
| Alcohol USP added as required for granulation. | |

Example 19

| Tablet Composition | |
|---|---|
| N-Propargyl-1(R)-aminoindan Mesylate | 7.81 mg* |
| Pregelatinized starch NF | 47.0 mg |
| Lactose NF hydrous | 66.0 mg |
| Microcrystalline cellulose NF | 20.0 mg |
| Sodium starch glycolate NF | 2.99 mg |
| Talc USP | 1.5 mg |
| Magnesium stearate NF | 0.7 mg |

*Equivalent to 5.0 mg of N-propargyl aminoindan base.

Example 20

| Tablet Composition | |
|---|---|
| N-Propargyl-1(R)-aminoindan Mesylate | 1.56 mg* |
| Lactose hydrous | 50.0 mg |
| Pregelatinized starch | 36.0 mg |
| Microcrystalline cellulose | 14.0 mg |
| Sodium starch glycolate | 2.14 mg |
| Talc USP | 1.0 mg |
| Magnesium stearate NF | 0.5 mg |

*Equivalent to 1.0 mg of N-propargyl aminoindan base.

Example 21

| Capsule Composition | |
|---|---|
| N-Propargyl-1(R)-aminoindan Mesylate | 5.0 mg |
| Pregelatinized starch | 10.0 mg |
| Starch | 44.0 mg |
| Microcrystalline cellulose | 25.0 mg |
| Ethylcellulose | 1.0 mg |
| Talc | 1.5 mg |
| Purified water added as required for granulation. | |

The following Examples and the accompanying Tables and Figures relate to biological experiments carried out in accordance with this invention.

Example 22
Inhibition of MAO Activity in vitro
Experimental Protocol

The MAO enzyme source was a homogenate of rat brain in 0.3M sucrose, which was centrifuged at 600 g for 15 minutes. The supernatant was diluted appropriately in 0.05M phosphate buffer, and pre-incubated with serial dilutions of compounds: R(+)-PAI, S(−)-PAI and racemic PAI for 20 minutes at 37° C. $^{14}$C-Labelled substrates (2-phenylethylamine, hereinafter PEA; 5-hydroxytryptamine, hereinafter 5-HT) were then added, and the incubation continued for a further 20 minutes (PEA), or 30–45 minutes (5-HT). Substrate concentrations used were 50 uM (PEA) and 1 mM (5-HT). In the case of PEA, enzyme concentration was chosen so that not more than 10% of the substrate was metabolized during the course of the reaction. The reaction was then stopped by addition of tranylcypromine (to a final concentration of 1 mM), and the incubate filtered over a small column of Amberlite CG-50 buffered to pH 6.3. The column was washed with 1.5 ml water, the eluates pooled and the radioactive content determined by liquid scintillation spectrometry. Since the amine substrates are totally retained on the column, radioactivity in the eluate indicates the production of neutral and acidic metabolites formed as a result of MAO activity. Activity of MAO in the sample was expressed as a percentage of control activity in the absence of inhibitors after subtraction of appropriate blank values. The activity determined using PEA as substrate is referred to as MAO-B, and that determined using 5-HT as MAO-A.

Results

Figure 2:
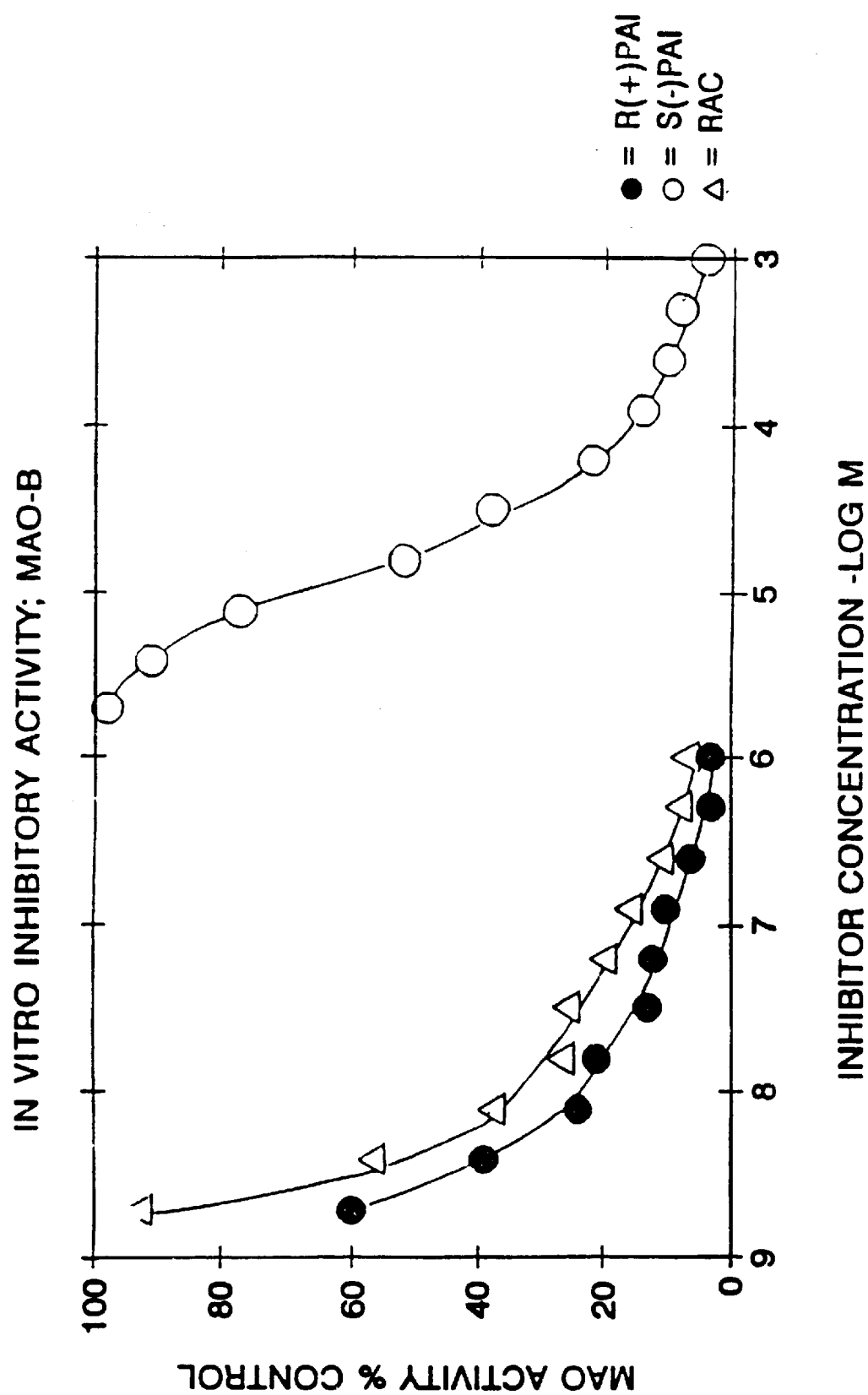
FIG. 2 is a graphic representation of the results according to Example 22 showing in vitro MAO-B inhibitory activity.

Inhibitory activity of R(+)-PAI, S(−)-PAI and racemic-PAI were examined separately in vitro, and the results of typical experimental runs are shown in FIGS. 1 and 2. The entire experiment was repeated three times. Concentrations of inhibitor producing 50% inhibition of substrate metabolism (IC-50) were calculated from the inhibition curves, and are shown in Table 1B. From this data it can be seen that:

(a) the R(+)-PAI is twice as active as the racemate for inhibition of MAO-B;

(b) the R(+)-PAI is 29 times more active for inhibition of MAO-B than MAO-A;

(c) the S(−)-PAI is only 1/6,800 as active as the R(+)PAI for inhibition of MAO-B, and shows little or no selectivity between MAO-B and MAO-A.

TABLE 1A

IC-50 (nM) VALUES FOR INHIBITION OF MAO-A AND MAO-B BY RACEMIC-PAI AND THE R(+) AND S(−) ENANTIOMERS THEREOF IN RAT BRAIN HOMOGENATE IN VITRO

| IC-50 (nM) | | | | | |
|---|---|---|---|---|---|
| MAO-A | | | MAO-B | | |
| S(−) PAI | R(+) PAI | Rac | S(−) PAI | R(+) PAI | Rac |
| 26000 | 73 | 140 | 17000 | 2.5 | 5 |

The results of the same experiments using R(+) and S(−) MPAI (N-methyl-N-propargyl-1-aminoindan) are reported in Table 1B. Each of the enantiomers of MPAI is less selective in MAO-A and MAO-B inhibition than R(+)PAI. Furthermore, R(+)-MPAI is only five times as active as S(−)-MPAI in MAO-B inhibition, in contrast to R(+)-PAI which is about 7000 times as active as S(−)-PAT in this assay.

TABLE 1B

IC-50 (nM) VALUES FOR INHIBITION OF MAO-A AND MAO-B BY THE R(+) AND S(−) ENANTIOMERS OF MPAI IN RAT BRAIN HOMOGENATE IN VITRO

| | IC-50 (nM) | | | |
|---|---|---|---|---|
| | MAO-A | | MAO-B | |
| Compound: | S(−) MPAI | R(+) MPAI | S(−) MPAI | R(+) MPAI |
| | 70 | 3 | 50 | 10 |

Figure 3A:
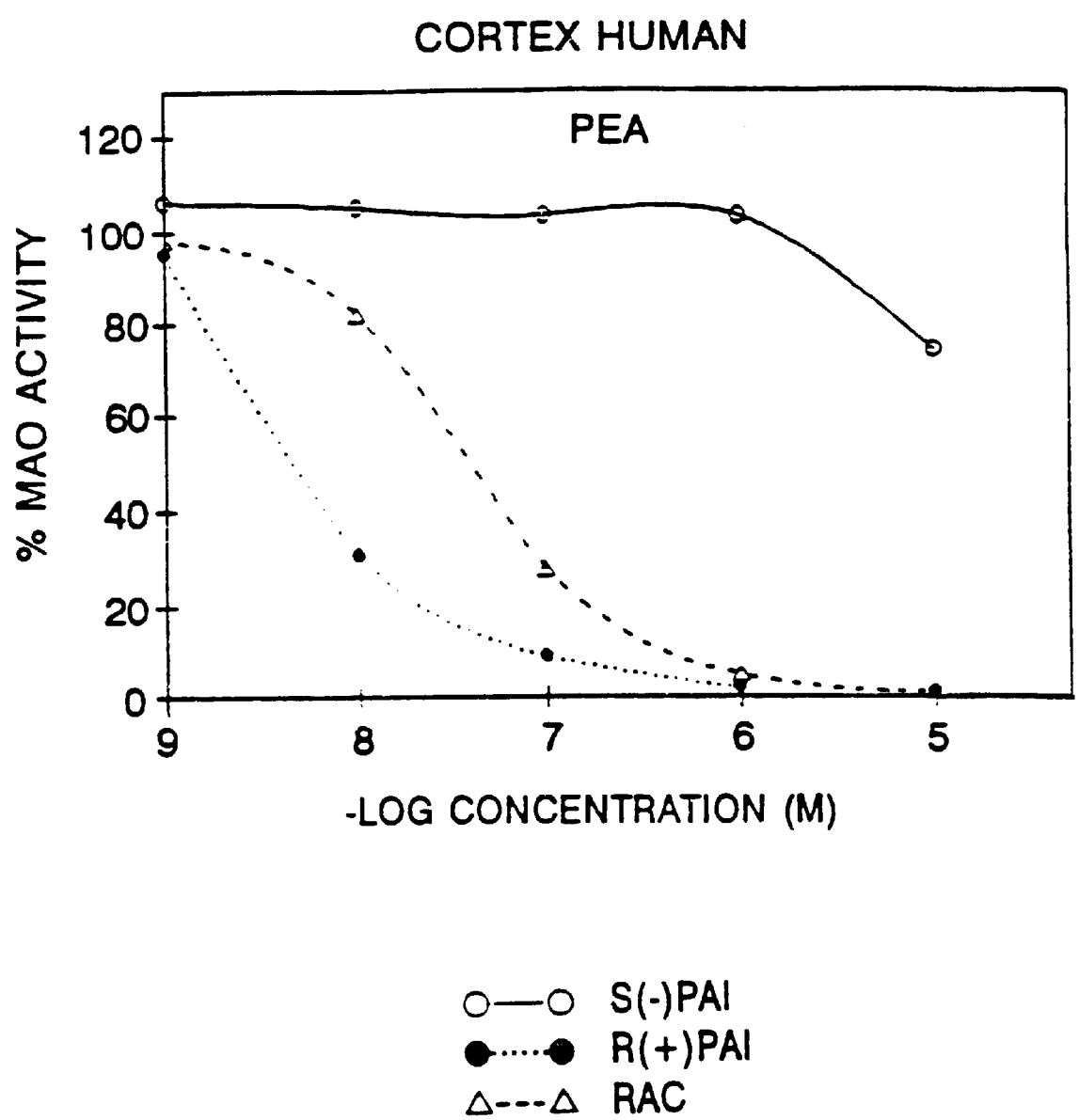
FIG. 3 is a graphic representation of the results according to Example 22 showing MAO activity in human cortical tissue.
Figure 3B:
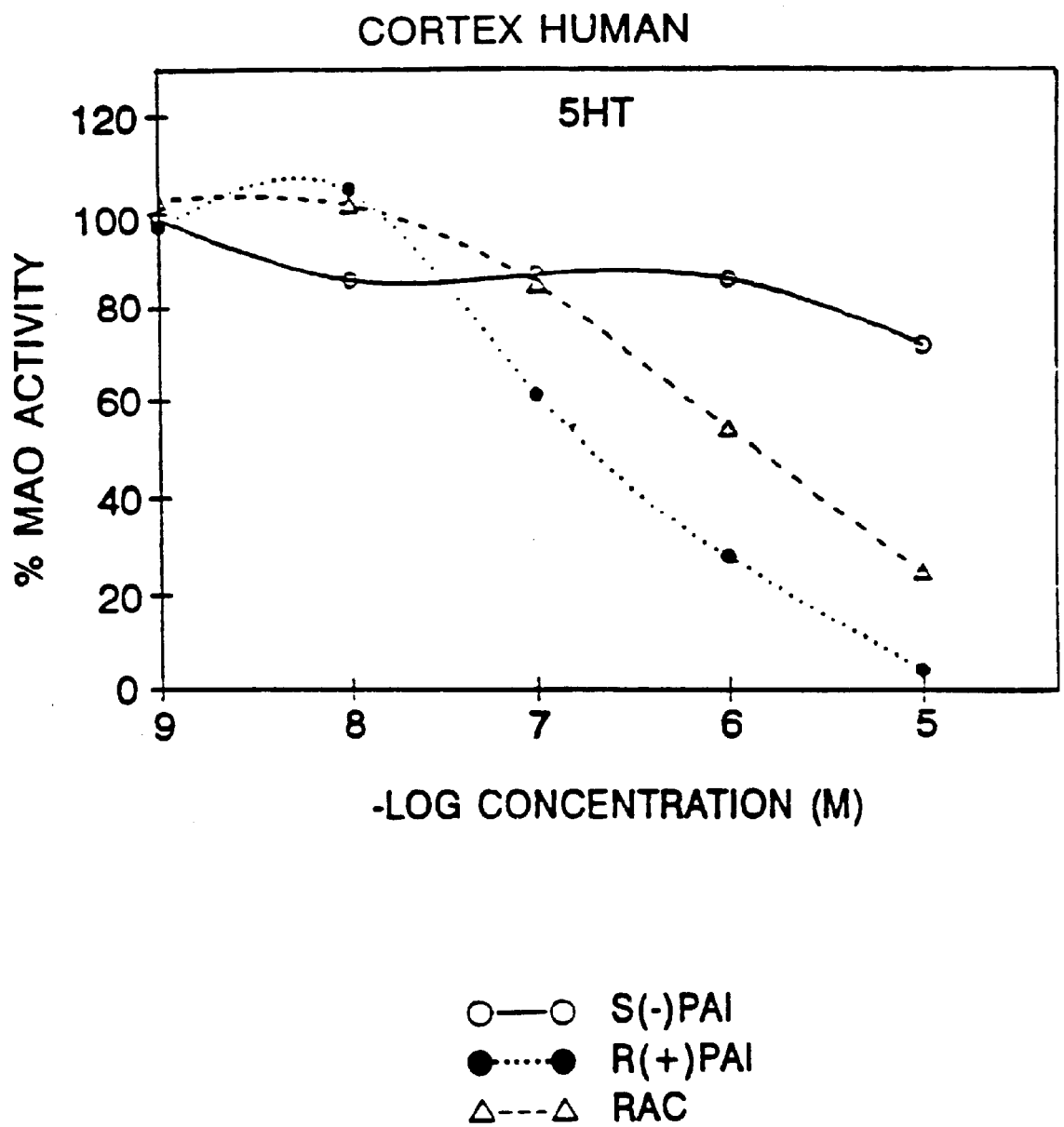
Figure 6:
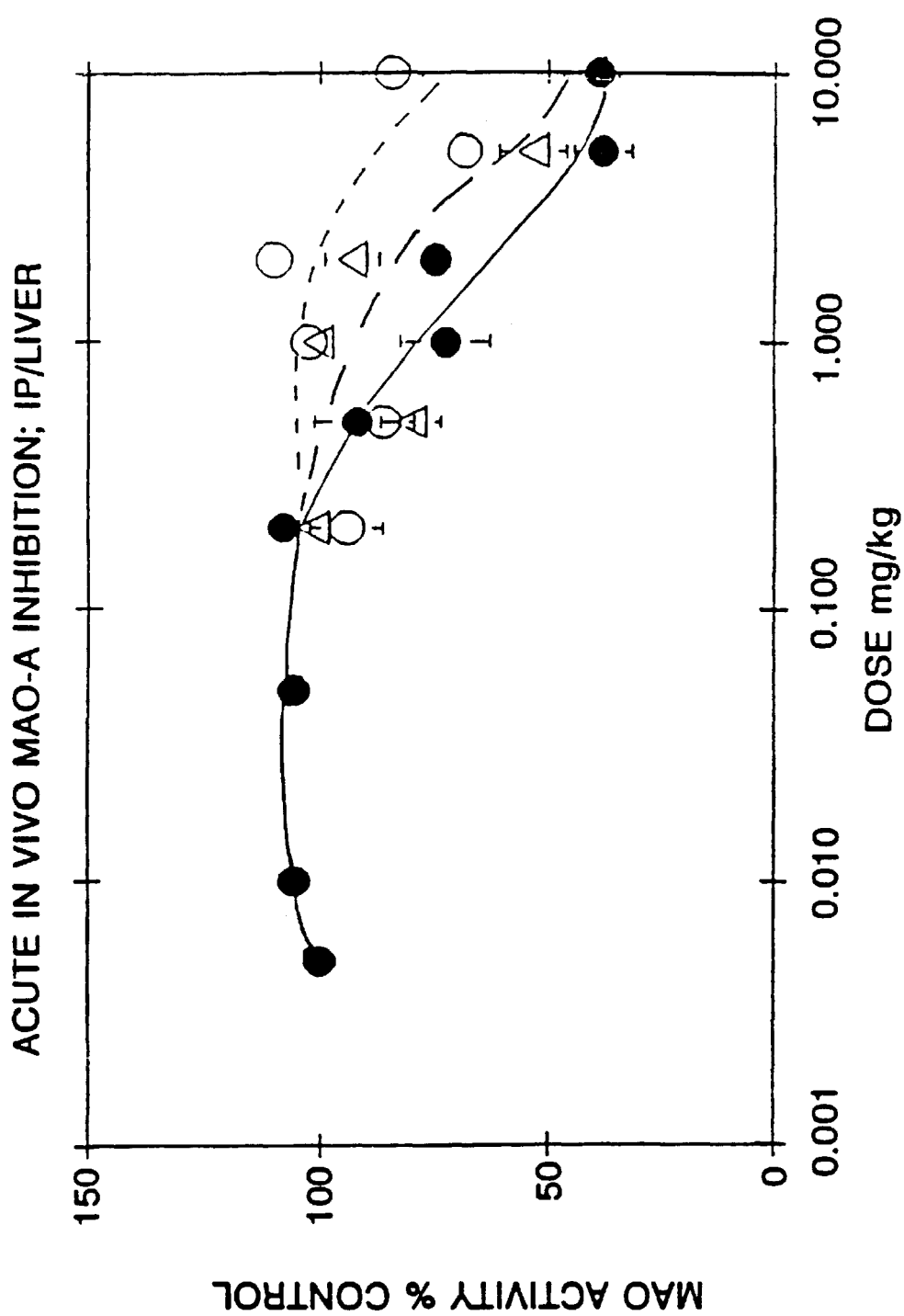
FIG. 6 is a graphic representation of the results according to Example 23 showing acute inhibition (i.p.) of MAO-A in liver.
Figure 7:
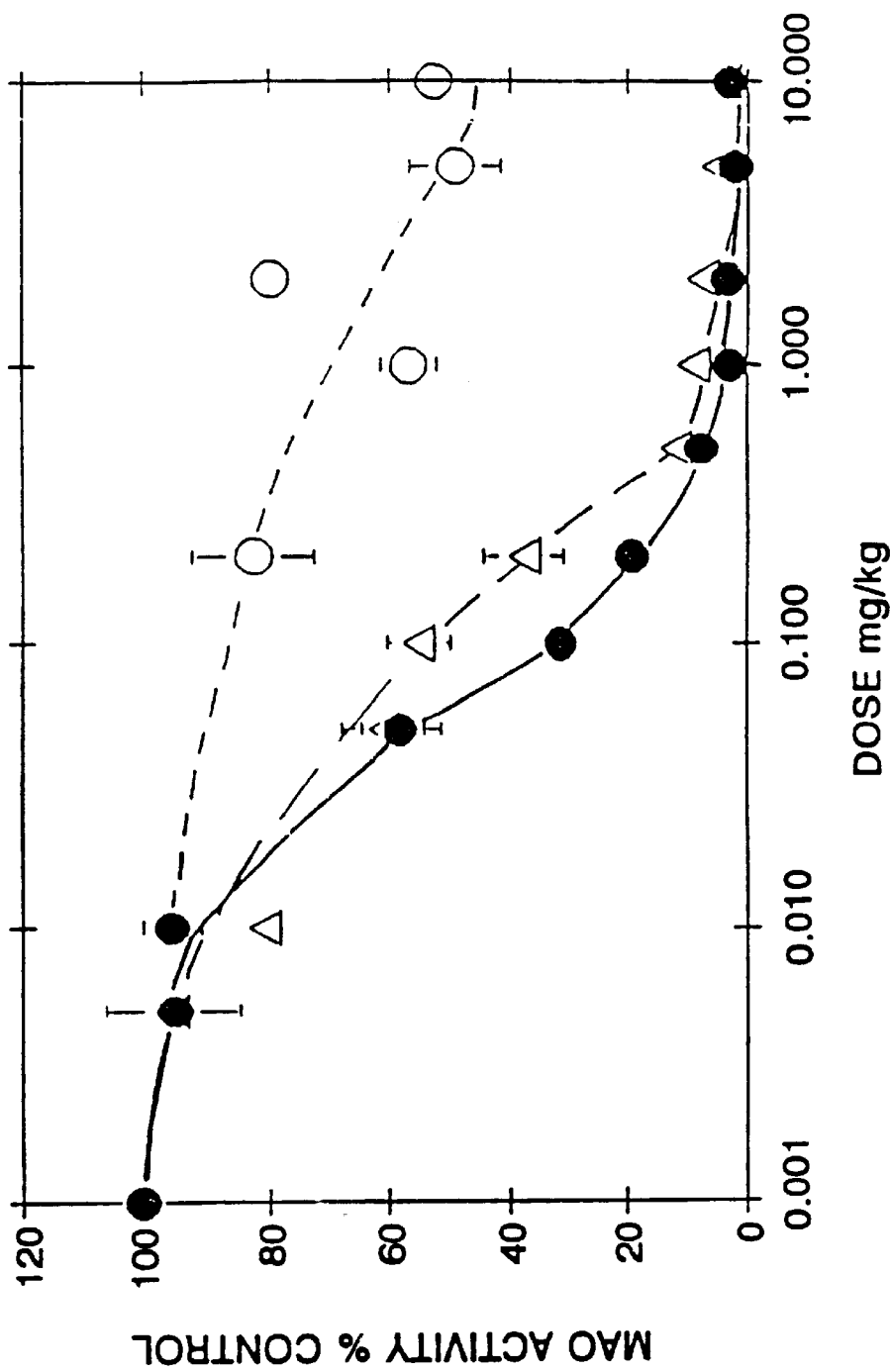
FIG. 7 is a graphic representation of the results according to Example 23 showing acute inhibition (i.p.) of MAO-B in liver.
Figure 8:
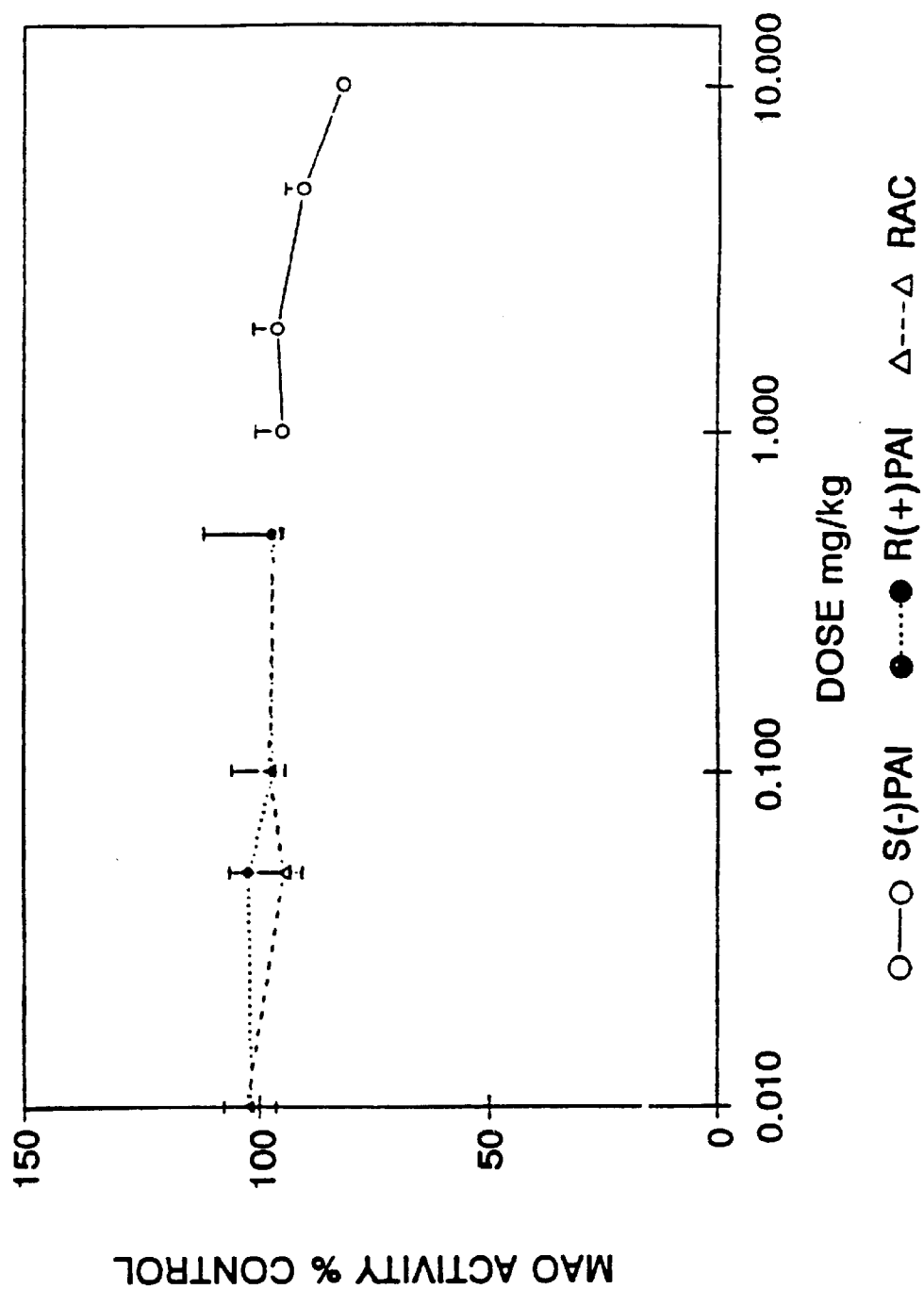
FIG. 8 is a graphic representation of the results according to Example 23 showing acute inhibition (per os) of MAO-A in brain.
Figure 9:
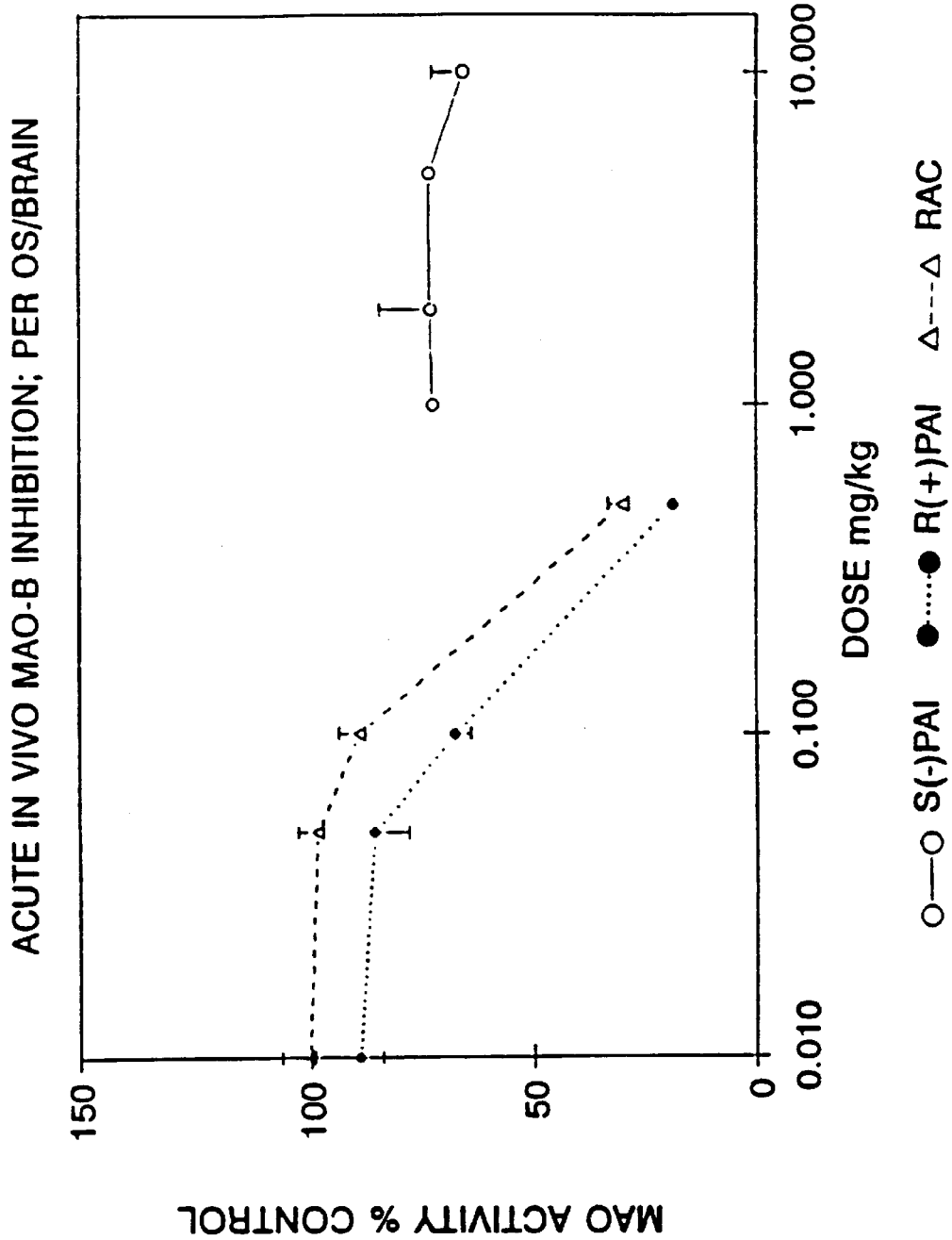
FIG. 9 is a graphic representation of the results according to Example 23 showing acute inhibition (per os) of MAO-B in brain.
Figure 10:
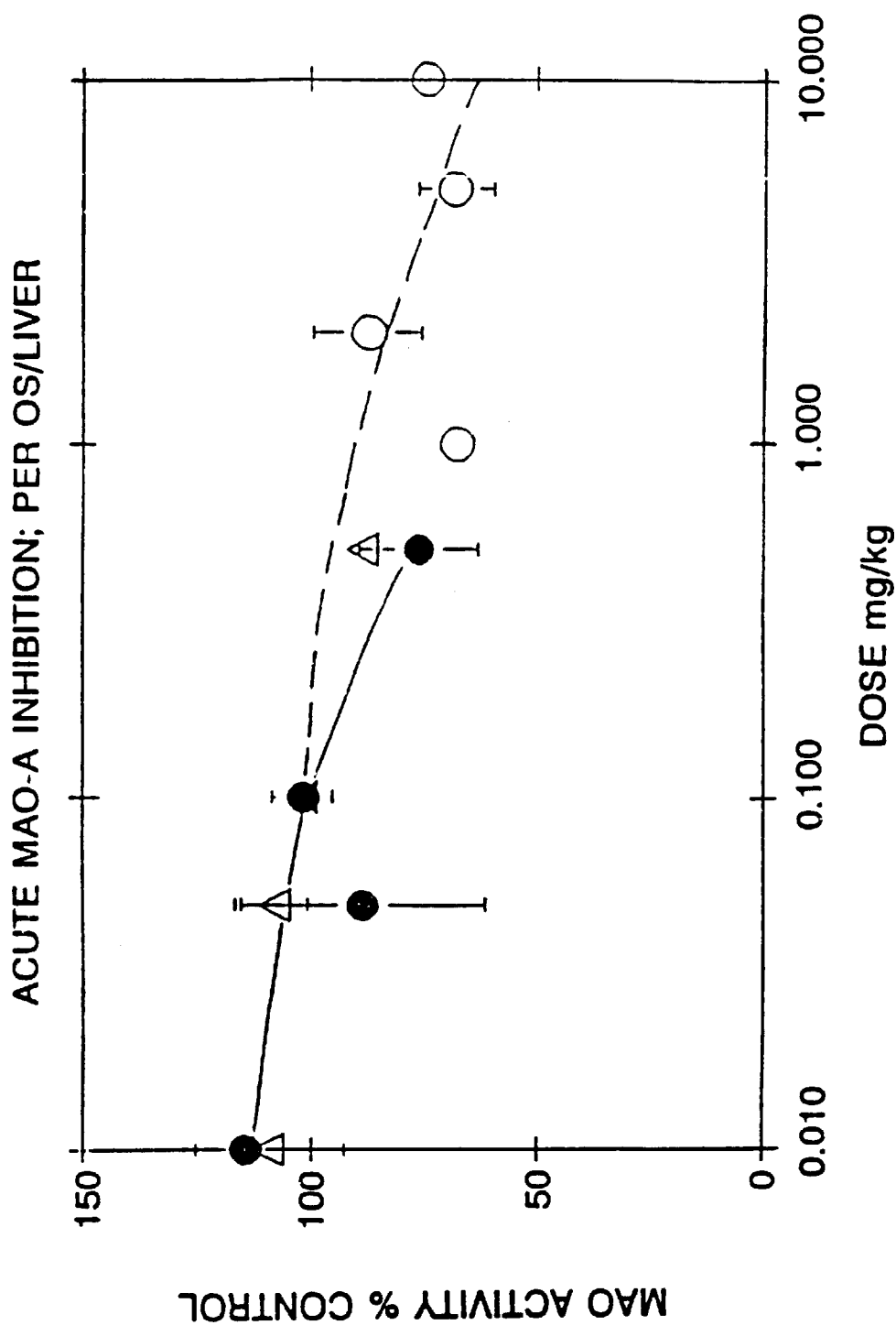
FIG. 10 is a graphic representation of the results according to Example 23 showing acute inhibition (per os) of MAO-A in liver.
Figure 11:
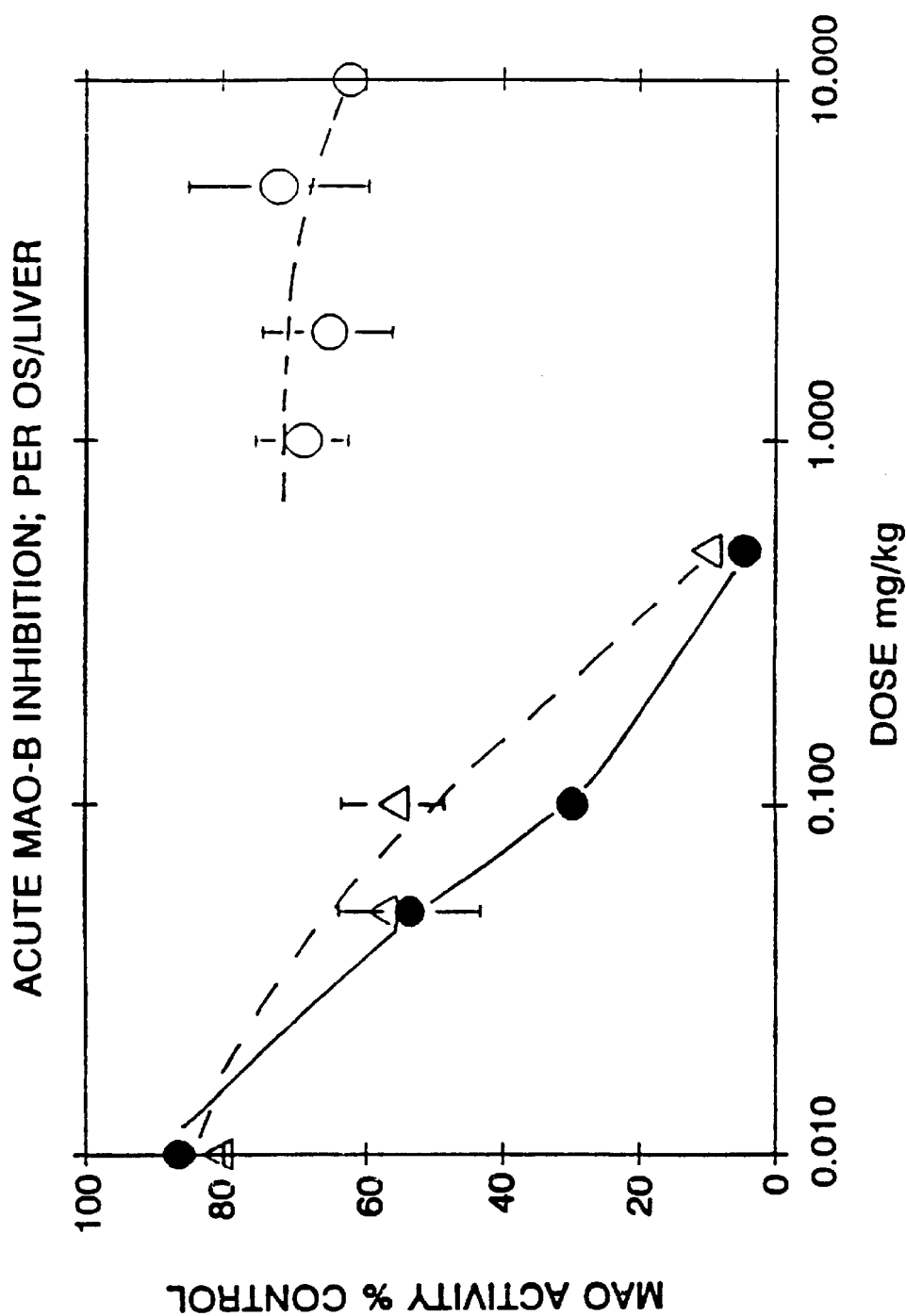
FIG. 11 is a graphic representation of the results according to Example 23 showing acute inhibition (per os) of MAO-B in liver.

Some experiments were also carried out with human cerebral cortical tissues obtained 6 hours post-mortem, and treated as described above. The results of such an experiment are shown in FIG. 3, where R(+)-PAI, S(−)-PAI, and racemic PAI are as defined herein.

Example 23
Inhibition of MAO Activity in vivo: Acute Treatment
Experimental Protocol Rats (male Sprague-Dawley-derived) weighing 250±20 g were treated with one of the enantiomers or the racemic form of PAI by intraperitoneal injection (ip) or oral gavage (po) and decapitated 1 h or 2 h later respectively. Groups of three rats were used for each dose level of inhibitor, and MAO activity determined in brain and liver using the general technique described above. The amount of protein in each incubation was determined using the Folin-Lowry method, and enzyme activity calculated as nmol of substrate metabolized per hour of incubation for each mg of protein. Activity of MAO in tissues from animals treated with inhibitors was expressed as a percentage of the enzyme activity in a group of control animals administered vehicle (water for oral administration, 0.9% saline for ip injection) and killed as above.

Results

None of the dose levels used with the inhibitor drugs produced any obvious behavioral alteration. The results are depicted in FIGS. 4 to 11. Following i.p. administration, compound R(+)PAI produced 90% inhibition of brain MAO-B activity at a dose of 0.5 mg/kg. The same dose produced only 20% inhibition of MAO-A activity. By oral administration, the same dose of R(+)PAI produced 80% inhibition of MAO-B with no detectable inhibition of MAO-A. Essentially similar results were seen for inhibition of hepatic MAO, as for brain MAO. The doses producing 50% inhibition of MAO-A and MAO-B (IC-50) were calculated from the inhibition curves, and are shown in Table 2. These data show: (a) that MAO inhibitory activity of R(+)PAI is maintained in vivo in the rat; (b) that selectivity for inhibition of MAO-B, as opposed to MAO-A, by R(+)PAI is maintained in vivo; (c) that the much greater activity of the (+)-enantiomer as opposed to the (−)-enantiomer, is maintained in vivo; (d) that the compounds are effectively absorbed after oral administration; and (e) that the compounds effectively pass the blood-brain barrier, and effectively inhibit brain MAO. The fact that R(+)-PAI was about twice as active as the racemic compound for inhibition of MAO-B is a reflection of the extremely low activity of S(−)-PAI for inhibition of MAO-B.

TABLE 2

IC-50 VALUES (mg/kg) FOR INHIBITION OF MAO-A AND MAO-B BY R(+)-PAI, S(−)-PAI OR RACEMIC-PAI, IN THE RAT FOLLOWING INTRAPERITONEAL (I.P.) INJECTION OR ORAL ADMINISTRATION (P.O.)

| Com- | MAO-A | | | MAO-B | | |
|---|---|---|---|---|---|---|
| pound: | S(−) PAI | R(+) PAI | Rac | S(−) PAI | R(+) PAI | Rac |
| I.P. BRAIN | >10 | 1.2 | 2.5 | >10 | 0.07 | 0.22 |
| I.P. LIVER | >10 | 5 | 5 | >10 | 0.06 | 0.11 |
| P.O. BRAIN | >10 | >5 | >5 | >10 | 0.17 | 0.29 |
| P.O. LIVER | >10 | >5 | >5 | >10 | 0.05 | 0.09 |

(Rac = Racemic PAI)

Example 24

Inhibition of MAO Activity in vivo: Chronic Treatment

Experimental Protocol

Rats (specifications as in Example 23, 4 animals for each dose level) were treated with R(+)PAI or the racemic mixture at three dose levels (0.05, 0.1 and 0.5 mg/kg) by oral administration, one dose daily for 21 days, and decapitated 2 hours after the last dose. The activities of MAO types A and B were determined in brain and liver as described in Example 23.

Results

Figure 12:
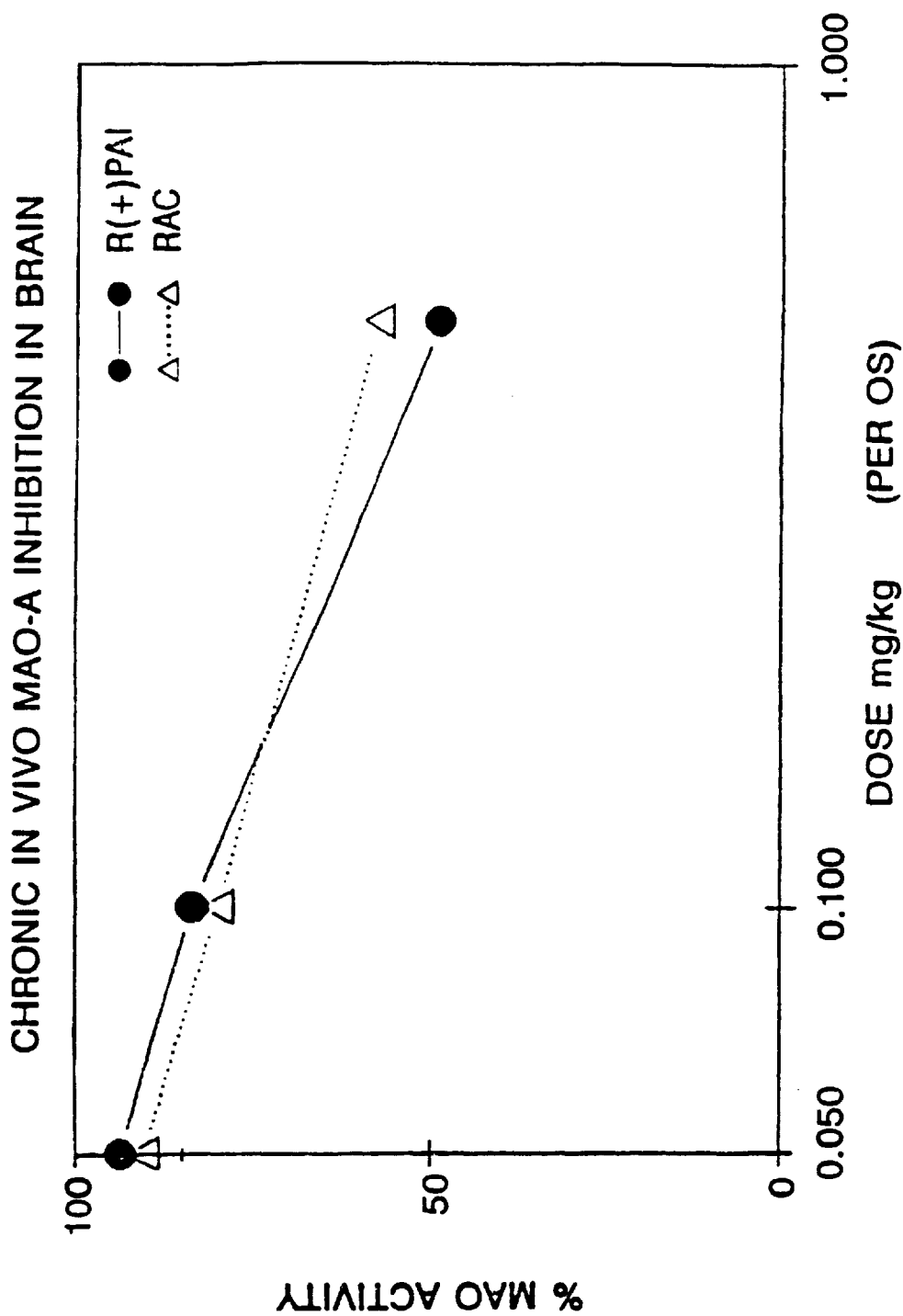
FIG. 12 is a graphic representation of the results according to Example 24 showing chronic inhibition of MAO-A in brain.
Figure 13:
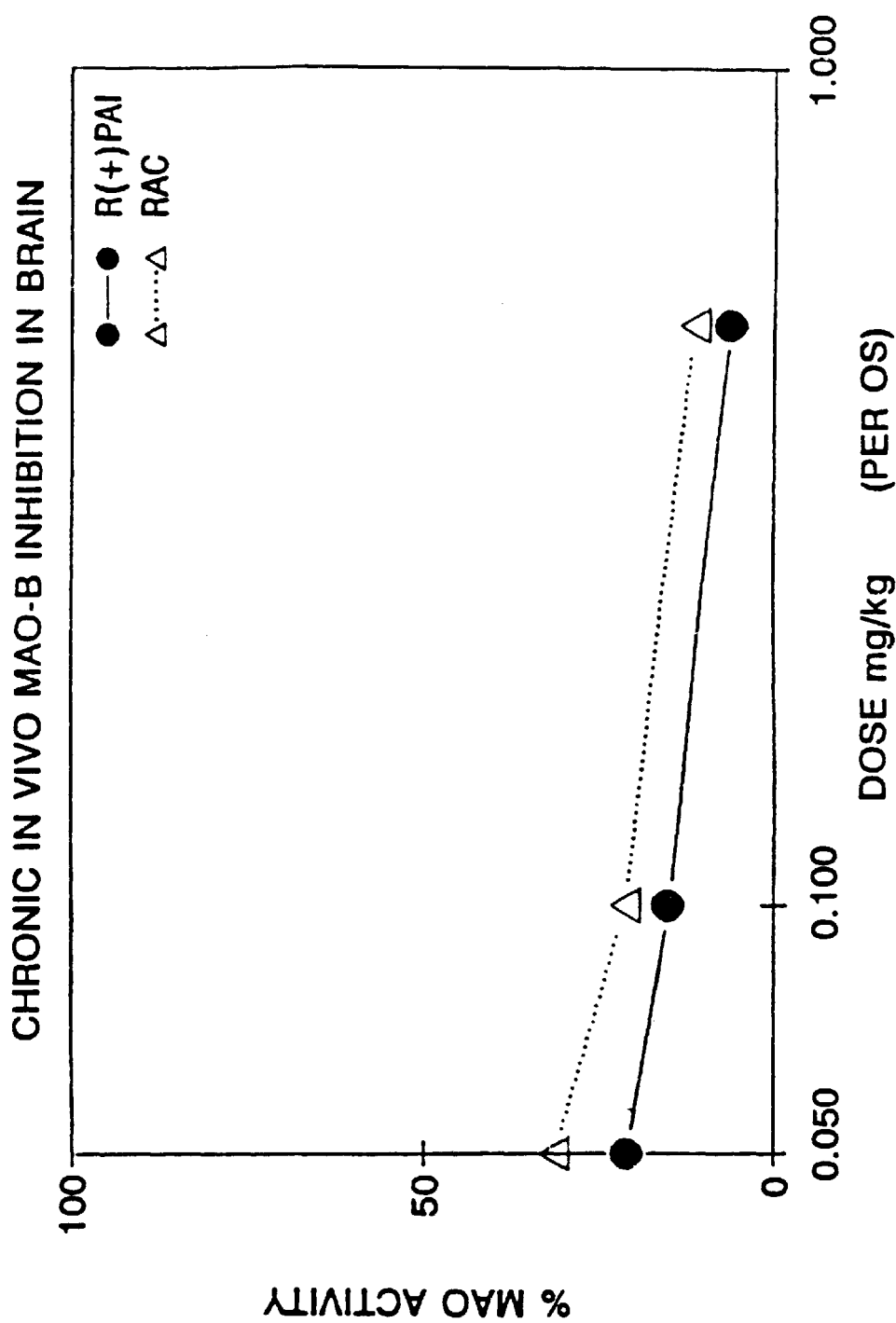
FIG. 13 is a graphic representation of the results according to Example 24 showing chronic inhibition of MAO-B in brain.
Figure 14:
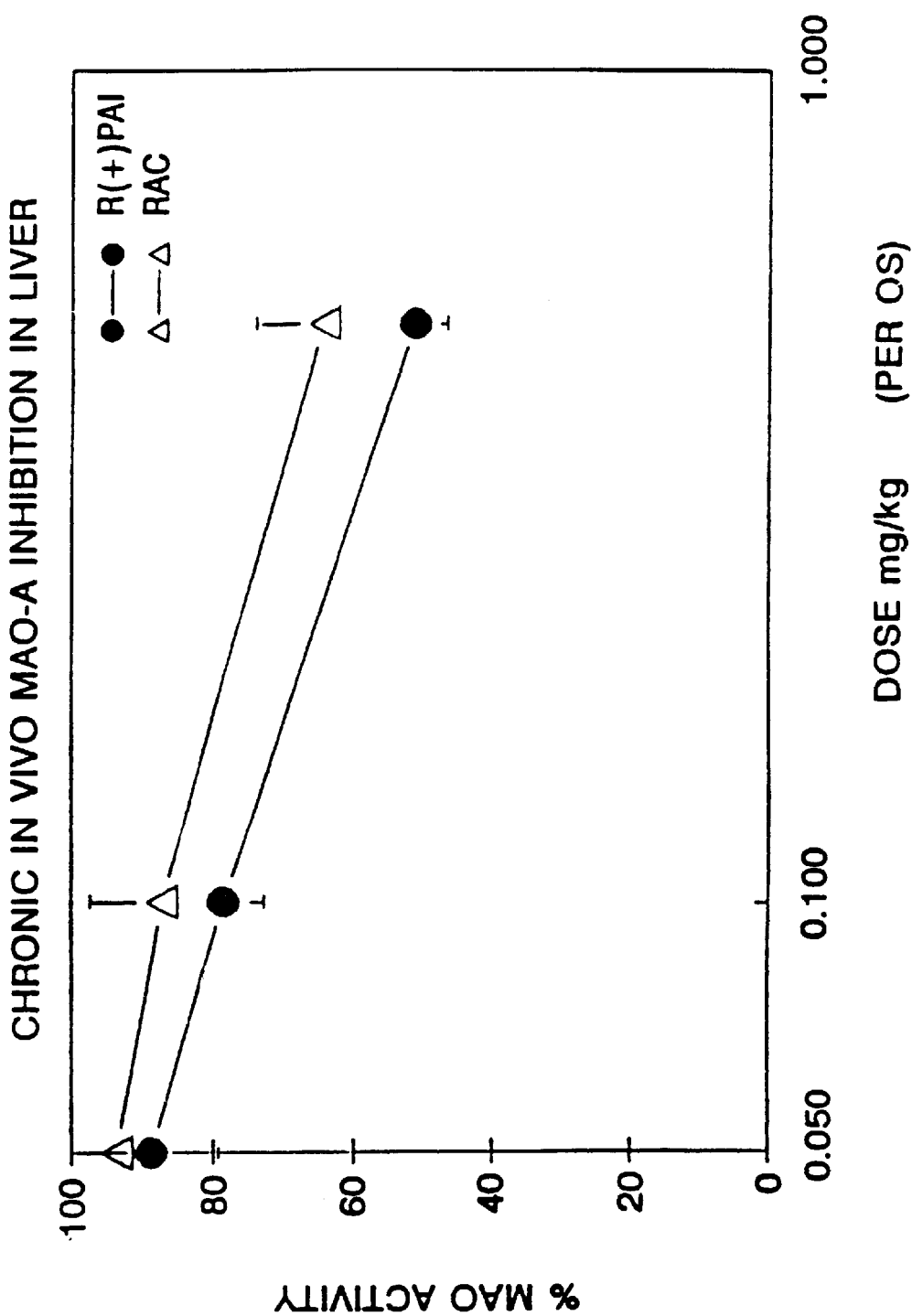
FIG. 14 is a graphic representation of the results according to Example 24 showing chronic inhibition of MAO-A in liver.
Figure 15:
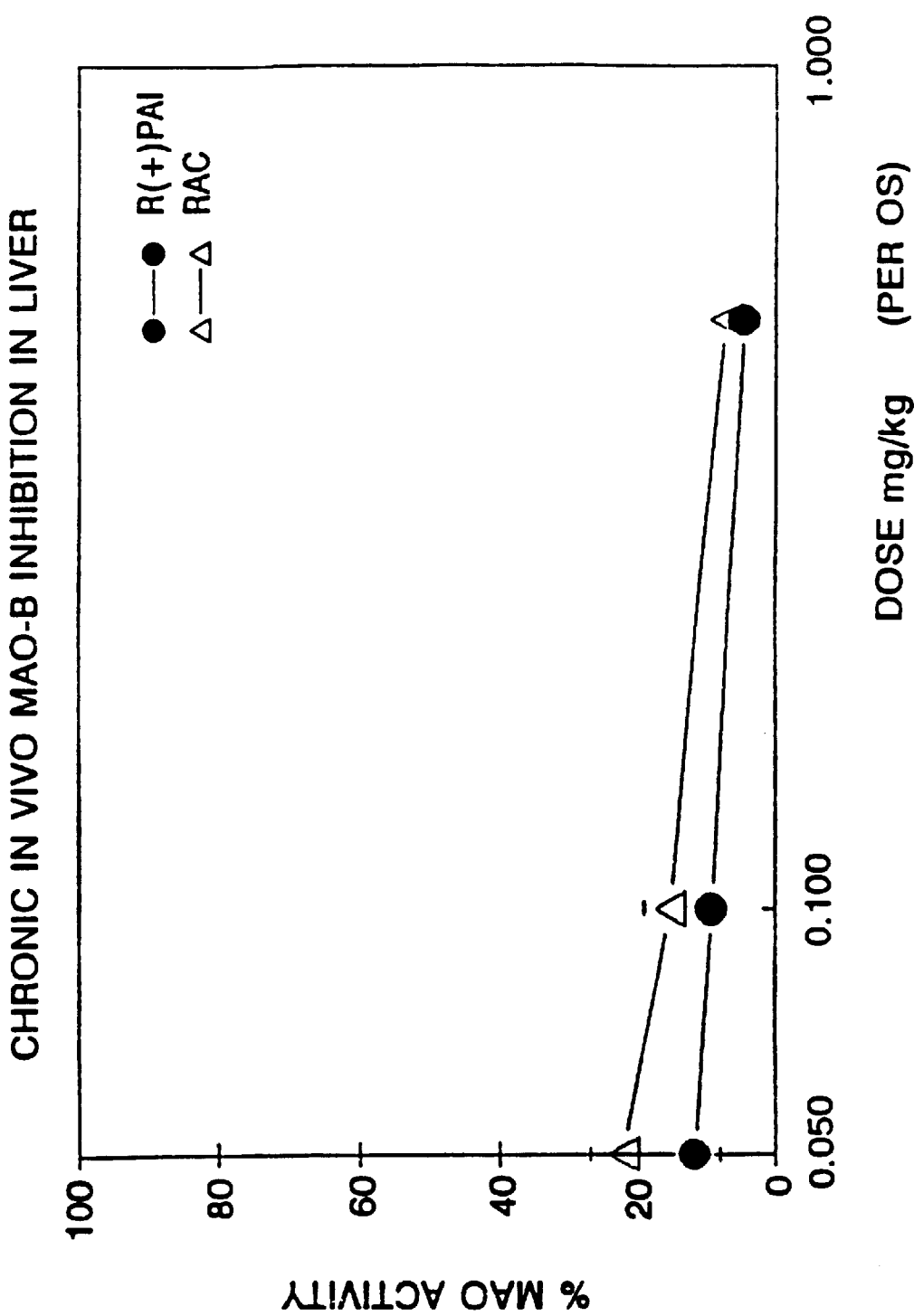
FIG. 15 is a graphic representation of the results according to Example 24 showing chronic inhibition of MAO-B in liver.

A daily dose of 0.1 mg/kg of compound R(+)PAI produced a good degree of selective inhibition, with more than 80% inhibition of brain MAO-B and 20% or less inhibition of brain MAO-A. At the higher dose of 0.5 mg/kg daily, MAO-A was still inhibited by less than 50% (FIGS. 12 and 13). Hepatic MAO showed a similar degree of selective inhibition (FIGS. 14 and 15). Compound R(+)PAI was again more potent than the racemic mixture by a factor of about twofold. In the case of brain MAO, R(+)PAI had a better degree of selectivity for inhibition of MAO-B than did the racemic mixture.

These results show that selectivity of MAO-B inhibition can be maintained following chronic treatment with the compounds. As with other irreversible inhibitors, the degree of enzyme inhibition is greater with chronic treatments than that following a single dose of the drug. Compound R(+)PAI shows a better degree of selectivity for inhibition of brain MAO-B than the racemic mixture.

Example 25

Irreversible Nature of MAO Inhibition

Experimental Protocol

A single dose of compound R(+)PAI (1 mg/kg) was administered by i.p. injection to groups of 4 rats, and the animals killed 2, 6, 18, 24, 48 and 72 hours later. Activity of MAO-B was determined in whole brain tissues as described hereinabove.

Results

Figure 16:
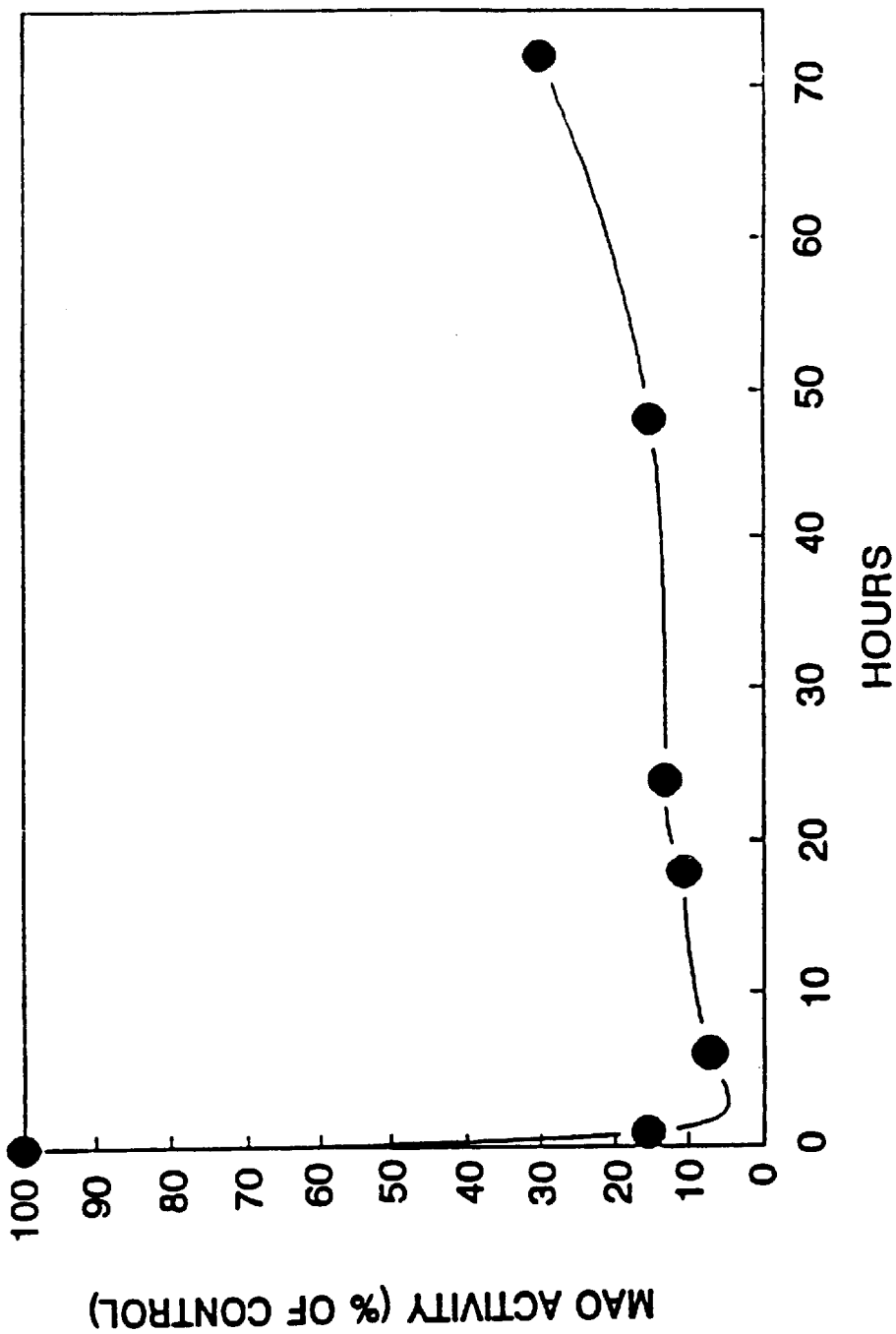
FIG. 16 is a graphic representation of the results according to Example 25 showing MAO-B activity in rat brain as a function of time following i.p. administration of R(+)PAI.

The results are shown in FIG. 16. Maximal inhibition of MAO-B was attained at 6 hours after injection. MAO activity had only returned to 30% of control activity at 72 hours after injection. This experiment demonstrates the irreversible nature of the MAO inhibition by R(+)PAI.

Example 26

Potentiation of Tyramine Pressor Effect in Conscious Rats

Experimental Protocol

Rats were anesthetized with a mixture of pentobarbital (30 mg/kg) and chloral hydrate (120 mg/kg) by intraperitoneal injection. The left carotid artery and jugular vein were cannulated with fine polytene tubing (artery) or fine silicone rubber tubing connected to polyethylene tubing (vein), the distal end of which was brought under the skin to an anchor point behind the neck. The tubing was filled with heparinized saline solution, and plugged with a fine steel rod. The animals were treated with 2.0 mg chloramphenicol by intramuscular injection and allowed to recover from the operation overnight. The following day, the rats were placed in a high-walled container permitting free movement. The arterial catheter was connected to a pressure transducer via a 100 cm length of saline-filled, fine-bore polyethylene tubing, and the venous catheter connected to a 1 ml syringe via a similar length of tubing, which, together with the syringe, contained a solution of tyramine hydrochloride in saline (1 mg/ml). Following an equilibration period of 30 to 40 minutes, tyramine injections (50 or 100 μg) were given, and blood pressure responses recorded. An interval of at least 15 minutes was maintained between injections after return of blood pressure to control values. Control pressor responses were established, then one of the drugs was injected intraperitoneally, and tyramine responses were repeated over the next 4 hours. The area under the blood pressure response curve was estimated, and the ratio of this area after treatment to before treatment and to 1 to 3 hours after injection of the compounds, was determined using the average of 3 to 4 values obtained in the control period.

Results

The results are shown in Table 3. Compound R(+)PAI at a dose of 1 mg/kg (which causes complete inhibition of MAO-B in brain and liver, and 40 to 50% inhibition of MAO-A in these tissues) caused no significant potentiation of tyramine pressor response. At the higher R(+)PAI dose of 5 mg/kg (which causes more extensive inhibition of MAO-A in brain and periphery), there was a significant potentiation of the tyramine pressor response, which was similar in extent to that produced by the same dose of deprenyl, and less than that produced by clorgyline (at a dose which inhibits hepatic MAO-A activity by over 85%).

TABLE 3

POTENTIATION OF TYRAMINE PRESSOR EFFECT IN CONSCIOUS RATS BY MAO INHIBITORS

| Inhibitor | Dose (mg/kg) | No. of rats (n) | Ratio Area Under Pressor Response Curve; After/Before | SEM* |
|---|---|---|---|---|
| Saline | | 12 | 1.25 | 0.28 |
| Clorgyline | 2 | 6 | 10.39 | 2.13 |
| (−) Deprenyl | 1 | 2 | 1.15 | |
| (+) Deprenyl | 5 | 3 | 2.36 | 0.16 |
| R(+) PAI | 1 | 3 | 1.38 | 0.7 |
| R(+) PAI | 5 | 3 | 3.49 | 0.98 |

*SEM = standard error of the mean

From this experiment it can be concluded that compound R(+)PAI causes no potentiation of the tyramine pressor effect at a dose which effectively inhibits MAO-B.

Example 27
Suppression of MPTP-induced Dopaminergic Toxicity by R(+)PAI

1-Methyl-phenyl-1,2,3,6-tetrahydropyridine (MPTP) is a neurotoxin that damages nigrostriatal dopaminergic neurons in several mammalian species, including mice, and produces a Parkinsonian syndrome in humans and primates. A crucial initial step in the mechanism of its neurotoxicity involves conversion of MPTP to its toxic metabolite 1-methyl-4-phenyl pyridinium ion (MPP+). This reaction is catalyzed by the enzyme MAO-B and probably takes place outside of dopaminergic neurons, mainly in glia. It is known that MPTP is both a substrate and an irreversible inhibitor of MAO-B. Pretreatment of experimental animals with MAO-B inhibitors such as deprenyl or pargyline protects against and prevents the MPTP-induced damage to nigrostriatal neurons because the oxidative conversion of MPTP to MPP+ is blocked. The progressive nigrostriatal degeneration in Parkinson's may be due to exposure to environmentally-derived exogenous MPTP-like neurotoxins. In such cases, there is an additional strong indication of initiation of sustained treatment with an MAO-B inhibitor from the very early stages of Parkinson's disease in the hope that it will neutralize the damaging effects of such yet putative MPTP-toxins, and thus arrest or slow down the progression of the illness. A successful MAO-B inhibitor drug is currently judged by its ability to block MPTP-induced damage to nigrostriatal dopaminergic neurons in vivo. The (−) and (+) enantiomers of PAI were therefore tested for their potency in preventing or attenuating the MPTP-induced striatal dopamine depletions in mice.

Experimental Protocol

Male C57 black mice (20–25 g weight) were (a) injected with MPTP.HCl (30 mg/kg dissolved in distilled water, s.c.), or vehicle alone, or one hour after pretreatment with the (−) or (+) isomers of PAI (2.5 mg/kg, i.p.), or with deprenyl (5 mg/kg, i.p.), and (b) decapitated 5 days later. Brains were removed and corpora striata dissected on an ice-cold glass plate and frozen on dry ice. Striatal tissues were homogenized in 0.1 M perchloric acid, and deproteinized aliquots containing dihydroxybenzylamine as an internal standard were assayed for dopamine and its major metabolite 3,4-dihydroxy-phenylacetic acid (DO PAC) using HPLC with electrochemical detection.

Results

Table 4 shows the results of this experiment. Treatment with MPTP alone produced marked striatal dopamine (DA) and DO PAC depletions. Treatment with the (−) and (+) enantiomers of PAI or with (−) deprenyl did not affect striatal DA concentrations. Pretreatment with the (−) isomer of PAI did not affect the MPTP-induced DA and DO PAC levels in the striatum. The (+)-isomer of PAI given before MPTP completely abolished the reduction in striatal DA and DO PAC levels produced by the toxin. At a dose of 2.5 mg/kg, (+)PAI was equipotent to (−) deprenyl (5 mg/kg) in its protective effect.

TABLE 4

EFFECT OF PRETREATMENT WITH THE (−) AND (+) ENANTIOMERS OF THE MAO-B INHIBITOR PAI ON THE STRIATAL DA AND DOPAC DEPLETIONS INDUCED BY MPTP IN MICE IN VIVO

| | DA | DOPAC |
|---|---|---|
| | (ng/mg protein) | |
| Control | 162.8 ± 7.2 | 8.4 ± 0.5 |
| MPTP | 53.1 ± 6.2 | 3.2 ± 0.3 |
| (−) PAI | 174.0 ± 4.8 | 7.5 ± 0.2 |
| (−) PAI + MPTP | 53.4 ± 6.9 | 7.0 ± 0.6 |
| (+) PAI | 185.0 ± 6.9 | 3.3 ± 0.3 |
| (+) PAI + MPTP | 177.8 ± 14.4 | 6.0 ± 0.3 |
| (−) Deprenyl | 170.6 ± 7.1 | 5.6 ± 0.3 |
| (−) Deprenyl + MPTP | 197.0 ± 8.0 | 6.4 ± 0.5 |

Above values for DA and DOPAC expressed as Mean±S.E.M. and number of rats. n=7–11 in each group.

These results indicate that the R(+)PAI is an excellent MAO-B inhibitor in vivo, and is of especially great potential for the treatment of Parkinson's disease.

While the invention has been described with reference to the aforementioned Examples and the accompanying Tables and Figures, it is not restricted thereto. Various modifications and applications of the invention are possible. For example, (R)-PAI may be combined, in a synergistic way, with a-tocopherol (a vitamin E derivative) for the treatment of Parkinson's disease.

Example 28
Effect of PAI Enantiomers on Amphetamine Induced Stereotype Behavior in Senescent Rats Amphetamine is known to induce stereotypic behavior (Sulser, F., and Sanders-Bush, E., Ann. Rev. Pharmacol., 11, 209–230 (1971)) by the mobilization of endogenous dopamine. Amphetamine is not metabolized by MAO-B. Inhibition of MAO-B by an effective inhibitor and administration of amphetamine cause release of dopamine which will not undergo degradation by the inhibited MAO-B. Thus, an increase of synaptic dopamine is expected after administration of amphetamine and effective MAO-B inhibitor leading to an increase in stereotype behavior-potentiation of the amphetamine effect. The extent of this behavior is rated in accordance with the number of lateral head movements over a period of 1 minute.

Experimental Protocol

The test compound was administered at a dose of 0.5 mg/kg/day in drinking water, 24 hours before the infliction of hypoxia (92% nitrogen+8% oxygen for 6 hours). Following that, amphetamine was injected s.c. at a dose of 0.5 mg/kg. 45 minutes later, lateral head movements were counted.

Results

The results of these experiments are shown in Table 5.

TABLE 5

EFFECT OF PAI ISOMERS ON AMPHETAMINE-INDUCED STEREOTYPE BEHAVIOR IN SENESCENT RATS (CONTROL AND HYPOXIA LESIONED)

| Group | | Stereotype Treatment Behavior Rating |
|---|---|---|
| Control (6) | — | 87 ± 10 |
| Control (5) | (+) PAI | 126 ± 16* |
| Control (4) | (−) PAI | 94 ± 18 |
| Hypoxia lesioned (5) | — | 93 ± 12 |
| Hypoxia lesioned (6) | (+) PAI | 143 ± 6* |

Numbers in parentheses are numbers of animals tested.
*$P < 0.001$ with respect to untreated hypoxia group or untreated control group correspondingly.

The results in Table 5 indicate that (+)PAI caused significant potentiation of the amphetamine-induced stereotype behavior in both hypoxia-lesioned and control rats. (−)PAI was totally inactive in this respect. These behavioral in vivo results corroborate previous biochemical findings that (+)PAI is an active inhibitor of MAO-B in the brain while (−)PAI is inactive in this respect.

Example 29

Effect on R(+)-PAI on the Improvement or Restoration of Memory

Newborn rat pups subjected to a brief episode of anoxia and then allowed to resume their growth in a normal way develop a long-lasting impairment of memory (Speiser, et al., Behav. Brain Res., 30, 89–94 (1988)). This memory impairment is expressed as an inferior performance in the passive avoidance test.

The effect of R(+)-PAI and S(−)-PAI on the improvement or restoration of memory was investigated in the passive avoidance test. If the drug is effective, it increases the latency of response to enter a dark compartment or chamber where an electroshock has been experienced earlier by the rat being tested. The latency of the maximal response is 300 seconds.

Experimental Protocol

Young rats were subjected to post-natal anoxia as described in Example 27. R(+)-PAI or S(−)-PAI were administered according to one of the following protocols.

Protocol A—Nursing mothers were given a dose of either isomer of 1–1.5 mg/kg/day in drinking water until weaning at 21 days. Following that, the weaned offsprings were directly treated with the same dose for 20 days. Treatment was terminated at 40 days and the test was performed at 60 days, that is 20 days after the last dose of the drug.

Protocol B—The dose was reduced to 0.5 mg/kg/day administered to the nursing mother until weaning at 21 days, then directly to the young rats to 60 days at which time the test was performed.

Passive Avoidance Test—The apparatus consisted of a lit chamber adjoining a dark chamber and a sliding door separating the two. At training, a rat was placed in the lit chamber for 30 seconds, and then the door was opened. The rat moved to the dark chamber with a latency that was recorded. Upon entry of the rat into the dark compartment, the door was closed and a 0.3 mA foot-shock was delivered for 3 seconds.

Retention (memory) after 48 hours was determined by repeating the test and recording the latency to step through from light to darkness to an arbitrary maximum of 300 seconds.

Results

The results of these experiments are shown in Table 6.

TABLE 6

EFFECT OF PAI ISOMERS ON PASSIVE AVOIDANCE RESPONSE IN YOUNG RATS (60-DAYS OLD)

| Group | Treatment | Before Electroshock | After Electroshock |
|---|---|---|---|
| PROTOCOL A | | | |
| Control | — | 49 ± 13 | 201 ± 111 |
| Control | (+) PAI | 49 ± 19 | 220 ± 100 (+9%)* |
| Control | (−) PAI | 48 ± 13 | 192 ± 116 |
| Anoxia-lesioned | — | 45 ± 11 | 183 ± 109 |
| Anoxia-lesioned | (+) PAI | 49 ± 10 | 239 ± 99 (19%)* |
| Anoxia-lesioned | (−) PAI | 55 ± 27 | 179 ± 123 |
| PROTOCOL B | | | |
| Control | — | 53 ± 20 | 104 ± 101 |
| Control | (+) PAI | 48 ± 11 | 128 ± 119 (+23%)* |
| Anoxia-lesioned | — | 45 ± 8 | 119 ± 105 |
| Anoxia-lesioned | (+) PAI | 52 ± 12 | 137 ± 126 (+15%)* |
| Anoxia-lesioned | (−) PAI | 48 ± 19 | 112 ± 112 |

Figures represent the latency in seconds for entering a dark compartment where an electroshock had been first experienced by the rat tested.
*The indicated percent increases are with respect to the corresponding anoxia or control groups.

The experimental results indicated that (+)PAI but not (−)PAI is effective in improving the memory of anoxia-lesioned and control rats. Drugs active in this test are considered to be potentially useful for treatment of various memory impairment disorders, dementia and especially senile dementia of the Alzheimer's type.

Example 30

Effect of R(+)-PAI on the Anoxia-induced Hyperactive Syndrome in Juvenile Rats

Rats that had been exposed postnatally to anoxia and then left to grow under normal conditions show increased motor activity in the open field at the age of 10–42 days (Hertshkowitz, et al., Dev. Brain Res., 7, 145–155 (1983)). The effect of R(+)PAI and S(−)PAI on such hyperactive syndrome was investigated.

Experimental Protocol

Anoxia was performed on rat pups on the first post-natal day. They were placed in a glass chamber and exposed to 100% nitrogen for 25 minutes. They were resuscitated by intermittent massage softly applied to the chest and then returned to their respective mothers. Control rats received the same treatment but with air instead of nitrogen.

The R(+)-PAI or S(−)-PAI (0.5 mg/kg/day) was administered to the nursing mothers in drinking water, thereby transferred to the sucklings through milk.

Locomotion was measured in 6 fully computerized cages (28×28 cm) by recording the number of crossings over a given period of time. Crossings of grid infrared beams at 4-cm intervals initiated electrical impulses which fed a counter. Recordings of motor activity were made at the ages of 15 and 20 days, over a period of 15 minutes.

Results

The experimental results are given in Table 7.

TABLE 7

EFFECT OF EACH OF THE TWO ENANTIOMERS ON THE ANOXIA-INDUCED HYPERACTIVE SYNDROME

| Group | Treatment | 15-day old rats | 20-day old rats |
|---|---|---|---|
| Control | — | 414 ± 192 (11) | 808 ± 212 (12) |
| Control | (+) PAI | 254 ± 149 (11) c | 719 ± 110 (13) |
| Anoxia-lesioned | — | 482 ± 119 (7) | 858 ± 96 (9) |
| Anoxia-lesioned | (+) PAI | 276 ± 186 (15) a | 737 ± 150 (16) c |
| Anoxia-lesioned | (−) PAI | 334 ± 196 (5) | 778 ± 232 (6) |

Numbers in parenthesis are numbers of animals tested.
— The figures are the numbers of crossings of infrared beam grid in the activity cage over a period of 15 minutes.
a $P < 0.001$ compared to anoxia untreated group.
b $P < 0.05$ compared to anoxia untreated group.
c $P < 0.05$ compared to control group.

These results indicate that chronic oral treatment with R(+)-PAI at a dose of 0.5 mg/kg administered to the nursing mother and reaching the milk-fed offspring significantly improved the hyperactive syndrome. Consequently, R(+)-PAI is a potentially useful drug for the treatment of the hyperactive syndrome in children.

Example 31

Stability Differences Among Ten Salts of PAI

Stability is an important factor in the selection of an optimal salt as a therapeutic drug. Different salts may alter the physicochemical and biological characteristics of a drug and can have a dramatic influence on its overall properties. (Berge, S. M., et al., J. Pharm. Sci. 66, 1 (1977); Gould, P. L., Int. J. Pharmaceutics, 33, 201 (1986)).

Experimental ps Synthesis of PAI Salts

A solution of an appropriate acid (1 mol-eq.) in 2-propanol was added to a solution of PAI (1 mol-eq.) while stirring in 2-propanol (Ar, BHT). The salt formed was filtered, washed with 2-propanol and ether, and dried under low pressure. Yields were between 70 to 90%. An exception in preparing PAI acetate involved using ether as the solvent.

Analytical Methods

The chromatographic separations were carried out using a Lichrosphere 60 RP select B 5 μ 125×4 mm (Merck) column, an HPLC (Jasco BIP-1) equipped with a L-4200 UV-Vis detector (Merck-Hitachi) set to 210 nm, and a D-2500 chromato-integrator (Merck-Hitachi). The eluent and diluent consisted of 80% distilled water/20% acetonitrile (HPLC grade), and 0.07 M perchloric acid adjusted to pH 2.5 with aqueous ammonia. The flow rate used was 1 ml/min, the appropriate PAI salt solution concentration was 250 μg/ml, and 20 μl of the solution were injected onto the chromatographic system.

The melting range was measured with an automatic apparatus (Mettler FP 80) and thermo-gravimetric analysis was performed on a Mettler TA 3000 system at a rate of 10° C./min in the applicable range. Solubility was determined by an appropriate dilution of the supernatant from a saturated PAI salt water solution and measured in a UVIKON 941 (Kontron) UV-Vis spectrophotometer. The salt form (mono- or di-salt) was obtained by elemental analysis using standard equipment for C, H, N and S determination. The pH was measured in a 1% aqueous solution of the PAI salts.

Results

The characterization of the various salts are summarized in Table 8.

TABLE 8

PHYSICOCHEMICAL PROPERTIES OF PAI SALTS

| PAI-salt m.w. | pH | Solubility mg/ml | Melting range (° C.) | % Wt. loss | Salt form |
|---|---|---|---|---|---|
| tartarate 492 | 5.5 | 33 | 176.2–177.3 | LT 0.1 | di |
| mesylate 267 | 4.3 | 635 | 156.8–157.6 | 0.1 | mono |
| maleate 287 | 4.0 | NLT 1000 | 87.2–87.8 | 0.1 | mono |
| sulphate 440 | 3.9 | 485 | 159.4–161.1 | 3.2 | di |
| chloride 207 | 4.2 | 238 | 177.0–180.0 | LT 0.5 | mono |
| tosylate 343 | 4.4 | 60–70 | 129.3–129.9 | LT 0.1 | mono |
| fumarate 287 | 3.s | 95 | 125.4–126.2 | 0.2 | mono |
| phosphate n.a. | 7.0 | NLT 720 | 109.5–110.4 | n.a. | n.a. |
| esylate 279 | 2.4 | NLT 300 | n.a. | n.a. | mono |
| acetate 231 | 6.1 | NLT 720 | 69.2–69.7 | 0.4 | mono | n.a. = not available

Comparative stability studies were carried out under sets of several accelerating conditions: I) heating at 80° C. for 72, 96 or 144 hours; and II) reflux in isopropanol for 30 hours. The degradation products developed were measured by HPLC and confirmed by TLC. The results are presented in Table 9 with the relative retention time (relative to the PAI peak; RRT) as an area percentage relative to total integrated peak area.

TABLE 9

DEGRADATION PRODUCTS DEVELOPED IN PAI SALTS UNDER SHORT TERM CONDITIONS

| | 80 C./72 h | | 80 C./144 h | | Reflux in iPrOH/30 h | |
|---|---|---|---|---|---|---|
| Salt | RRT[a] | %[b] | RRT | % | RRT | % |
| sulfate | ND[c] | ND | ND | ND | 0.47 | 0.22 |
| | | | | | 0.60 | 0.72 |
| phosphate | 0.60 | 0.22 | 0.60 | 0.57 | 0.60 | 2.62 |
| | | | | | 0.74 | 0.21 |
| | | | | | 1.84 | 0.20 |
| | | | | | 1.98 | 0.73 |
| chloride | ND | ND | ND | ND | 2.23 | 0.71 |
| mesylate | ND | ND | ND | ND | 0.60 | 0.08 |

TABLE 9-continued

DEGRADATION PRODUCTS DEVELOPED IN PAI SALTS UNDER SHORT TERM CONDITIONS

| Salt | 80 C./72 h | | 80 C./144 h | | Reflux in iPrOH/30 h | |
|---|---|---|---|---|---|---|
| | RRT[a] | %[b] | RRT | % | RRT | % |
| maleate | 0.60 | 0.41 | n.a. | | 0.60 | 2.17 |
| | 1.27 | 0.50 | | | 0.65 | 1.35 |
| | 1.48 | 0.33 | | | 1.29 | 0.59 |
| | 1.81 | 0.10 | | | 1.42 | 1.30 |
| | 3.07 | 1.44 | | | 1.50 | 0.16 |
| | 4.16 | 0.10 | | | 1.83 | 0.18 |
| | 4.84 | 7.76 | | | 1.98 | 0.23 |
| | | | | | 4.09 | 0.65 |
| acetate | 0.44 | 0.10 | n.a. | | 0.60 | 6.74 |
| | 0.60 | 2.56 | | | 0.74 | 0.35 |
| | 0.73 | 0.13 | | | 1.76 | 0.33 |
| | 1.29 | 0.71 | | | 1.84 | 0.16 |
| | 1.55 | 1.06 | | | 1.99 | 4.17 |
| | 1.75 | 21.85 | | | 3.60 | 0.27 |
| | 1.96 | 3.33 | | | | |
| | 2.15 | 0.08 | | | | |
| | 2.32 | 0.15 | | | | |
| | 2.83 | 0.15 | | | | |
| | 3.44 | 1.82 | | | | |
| esylate[d] | ND | ND | 0.85 | 0.26 | ND | ND |
| | | | 1.96 | 0.31 | | | limit of quantitation = 0.08%
n.a. = not available
[a]Relative retention time (relative to the PAI peak).
[b]Area percentage relative to total integrated peak area.
[c]No impurities detected.
[d]Ethyl sulfate salt.

The salts were submitted to visual inspection of color and form. The findings are shown in Table 10.

TABLE 10

APPEARANCE OF PAI SALTS UNDER DESTRUCTIVE CONDITIONS

| Salt | 80° C./72 h | 80° C./96 h | 80° C./144 h | reflux in iPrOH/30 h |
|---|---|---|---|---|
| sulfate | off white powder | n.a. | off white powder | brown powder |
| phosphate | brownish powder | n.a. | brown powder | brown powder |
| chloride | white powder | n.a. | white powder | off white powder |
| mesylate | white powder | n.a. | white powder | white powder |
| maleate | brown melted | brown | n.a. | brown melted |
| esylate | brownish melted | n.a. | dark brown melted | dark brown melted | n.a. = not available

These studies show that sulphate, esylate and mesylate possess significant advantages relative to the other salts due to good solubility and chemical stability. Of these three salts, mesylate is preferable due to its excellent stability even under destructive conditions.

Example 32
Reversal of Haloperidol-induced Catalepsy in Mice

Male, ICR mice 25–30 g each, were pretreated with either of the following drugs: Saline, (R)-PAI mesylate, or racemic-PAI mesylate. All drugs were administered i.p. in a volume of 0.2 mL. Two hours later, haloperidol was injected s.c. at a dose of 6 mg/kg in a volume of 0.1–0.2 mL. Motor coordination tests were made at 3 hours after giving haloperidol, that is, 5 hours after administering the presumed protective drugs.

Figure 17:
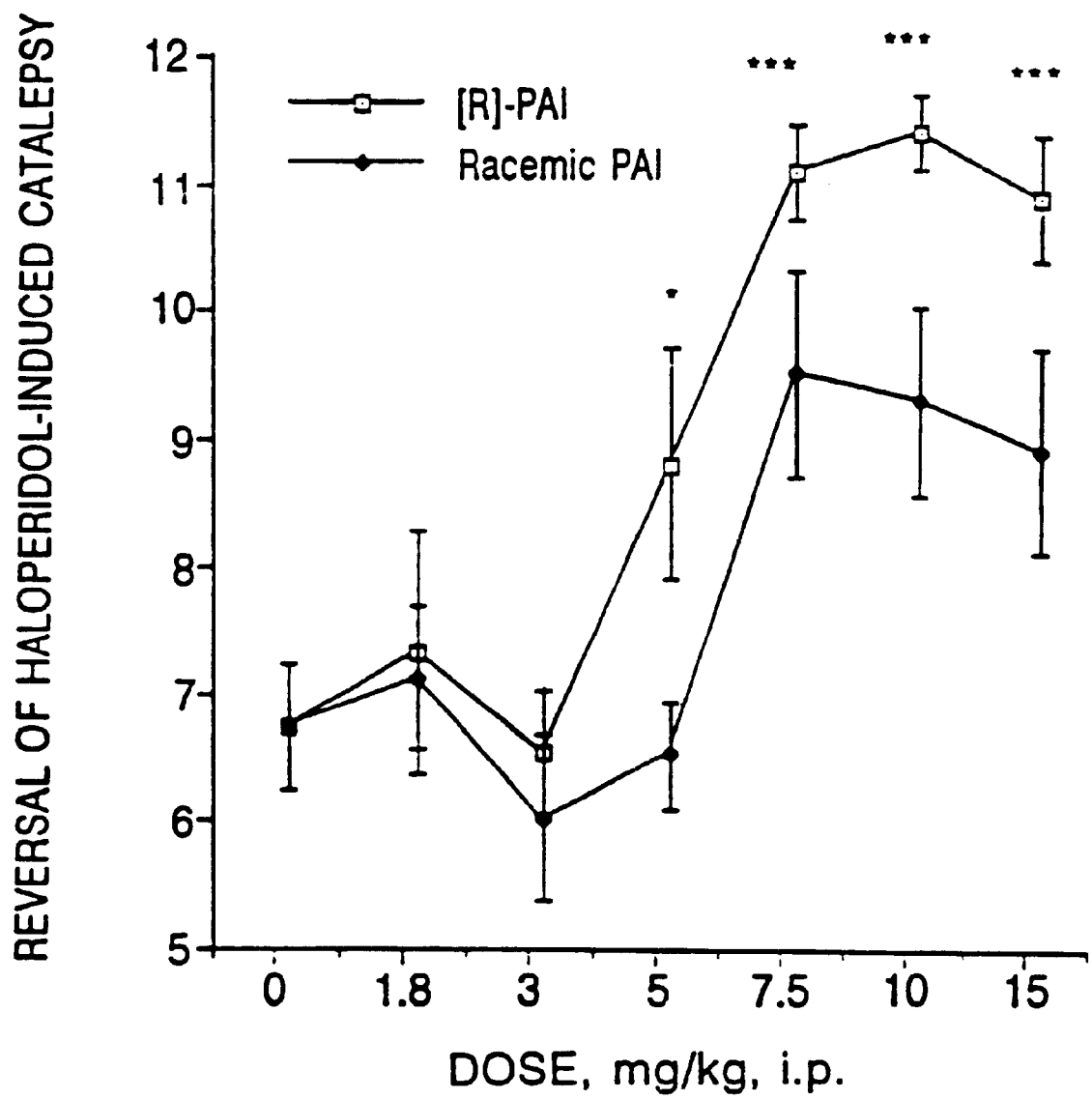
FIG. 17 is a graphic representation of the results according to Example 32 showing restoration of normokinesia in mice that had received haloperidol 6 mg/kg s.c. Mice received each of the test drugs i.p. at the indicated dose. 2 hours later they received haloperidol. Kinetic scores were taken 3 hours after haloperidol. These scores consisted of the ability to move horizontally along a rod, the ability to descend a vertical rod, and the shortening of catalepsia. In the absence of haloperidol, the maximum score is 12, with haloperidol alone, 6.6±0.03. Statistical significance was calculated by the Student's "t" test: * $p \leq 0.05$;  $p \leq 0.01$; *$p \leq 0.001$ with respect to haloperidol alone. The scores of (R)-PAI are significantly different from those of racemic-PAI at 5 mg/kg ($p \leq 0.05$), at 10 mg/kg ($p \leq 0.01$), and at 15 mg/kg ($p \leq 0.05$), (n=5.6). The dosage shown is for the free base of PAI (and not the mesylate salt).

Motor coordination tests and rigidity were quantified according to three different parameters: (a) ability to walk the length of a horizontal rod, 80 cm-long; (b) ability to climb down, face down, a vertical rod, 80 cm-long; (c) duration of immobility in an unnatural sitting posture whereby the abdomen of the mouse is pressed against a "wall." Full performance as in haloperidol-untreated mice is given the score of 4 in each test, or a total of 12 in all tests. Poor performance is given a score from 1 to 3. A key to score ratings is given in Table 9A. The effects of the various agents in antagonizing haloperidol-induced catalepsy are given in Table 11. At three hours after haloperidol, (R)-PAI mesylate conferred protection against haloperidol at 5–15 mg/kg, reaching a peak after effect at 7.5–10 mg/kg (activity score≈94% of saline control). Racemic PAI mesylate conferred partial protection in the range of 7.5–15 mg/kg, and was not active at 5 mg/kg. From FIG. 17, it can been seen that the dose-effect profile of either (R)-PAI mesylate or racemic PAI is such that an increase in dose beyond 10 mg/kg entails a decrease in effect, but that the racemic mixture is less potent throughout. This means that racemic PAI mesylate at twice the dose of (R)-PAI mesylate will always be less active than the (R) enantiomer.

Reversal of α-MpT-induced Hypokinesia in Rats

Figure 18:
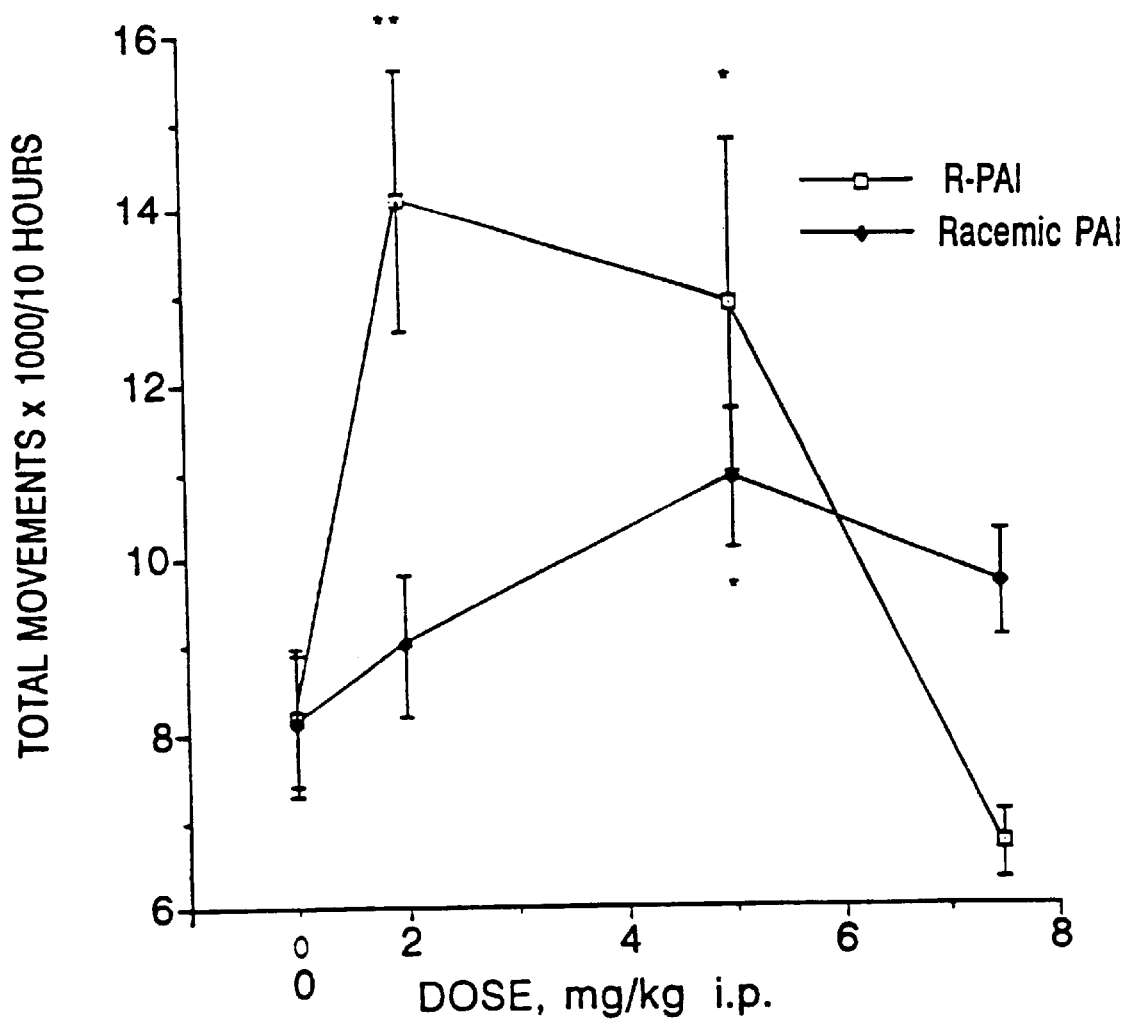
FIG. 18 is a graphic representation of the results according to Example 32 showing restoration of motor activity in rats treated with α-methyl-p-tyrosine at 100 mg/kg i.p. Rats received the test drug i.p. at the indicated doses. After two hours they received α-Mpt and were immediately placed in activity cages. Total motor activity was recorded for the duration of 10 hours. Control rats, treated with saline, only scored 15,862+1424. With α-Mpt alone, they scored 8,108±810. Statistical significance by the Student's "t" test: *$p \leq 0.05$; $p \leq 0.01$; *$p \leq 0.001$ with respect to α-MpT alone. The scores of (R)-PAI are significantly different from racemic-PAI at 2 mg/kg ($p \leq 0.01$), (n=6). Dosage shown is for the free base of PAI and not the mesylate salt.

The drug α-MpT is assumed to inhibit the formation of L-DOPA from tyrosine, and consequently the formation of dopamine itself. Lack of CNS dopamine is expressed as hypoactivity. Six month-old male Wistar rats (from Harlan Orkack, UK) were pretreated with saline, -(R)-PAI Mesylate or Rac PAI Mesylate, at the indicated doses. Two hours later they received i.p. α-MpT at a dose of 100 mg/kg in 0.3–0.5 mL. Controls received saline. Following this, motor activity was recorded in a computerized activity cage for the duration of 10 hours. The results are given in Table 12 and FIG. 18. At 2 mg/kg, (R)-PAI Mesylate restored the level of activity to about 90% of the saline-treated rats, but Rac PAI Mesylate was not active. In either case, the profile of the dose-effect curve was bell-shaped, suggesting a decrease in effect with an increase in dose beyond α-peak of 2–5 mg/kg. At 5 mg/kg Rac PAI Mesylate could not elicit a level of activity comparable to that of (R)-PAI Mesylate at 2 mg/kg.

From these measurements, (R)-PAI Mesylate and Rac PAI Mesylate do not share a similar pattern of activity in the restoration of normokinesia in haloperidol-treated mice and α-Mpt-treated rats. At all doses studied, (R)-PAI Mesylate is always more potent that Rac PAI Mesylate at the corresponding dose. Also, peak activity of Rac PAI Mesylate is always lower than peak activity of (R)-PAI Mesylate. Thus, Rac PAI Mesylate at a given dose is always less effective than (R)-PAI Mesylate at half the same dose. Doubling the dose of Rac PAI Mesylate with respect to (R)-PAI Mesylate does not produce an effect equivalent to that of (R)-PAI Mesylate.

Pharmacologically, Rac PAI Mesylate cannot be considered as consisting of 50% active ingredient which is (R)-PAI Mesylate and 50% inert material as diluent. The presence of (S)-PAI in Rac PAI Mesylate has an adverse effect on the activity of (R)-PAI, resulting in a more than two-fold decrease in potency. The decrease may be due to a direct adverse effect of (S)-PAI on behavioral parameters.

TABLE 11

REVERSAL OF HALOPERIDOL-INDUCED CATALEPSY IN MICE
WITH (R)-PAI MESYLATE AND RACEMIC MESYLATE
Mice received each of the test drugs i.p. at the indicated doses.
Two hours later they received haloperidol as described in the text.
The doses shown are for the free base.

| Dose, mg/kg | (R)-PAI Mesylate | | | Rac PAI Mesylate | | |
|---|---|---|---|---|---|---|
| | Score + SE | n | % of control | Score + SE | n | % of control |
| 1.8 | 7.2 ± 1 | 6 | 60 | 7.0 ± 0.6 | 6 | 59 |
| 3.0 | 6.4 ± 0.5 | 6 | 60 | 5.9 ± 0.7 | 6 | 49 |
| 5.0 | 8.7 ± 0.9* | 6 | 73 | 6.4 ± 0.4 | 6 | 53 |
| 7.5 | 11.0 ± 0.4*** | 5 | 92 | 9.4 ± 0.8++ | 6 | 78 |
| 10 | 11.3 ± 0.3*** | 6 | 94 | 9.2 ± 0.6*** | 6 | 77 |
| 15 | 10.8 ± 0.5*** | 5 | 90 | 8.8 ± 0.8* | 6 | 73 |
| Control saline | 12 ± 0 | 12 | 100 | | | |
| Haloperidol alone | 6.6 ± 0.3 | 16 | 59 | | | |

Statistical significance with respect to haloperidol alone:
*$p \leq 0.05$;
**$p \leq 0.01$;
***$p \leq 0.001$ by the Student's "t" test.
The scores for (R)-PAI are significantly different from those of racemic PAI at 5 mg/kg, $p \leq 0.05$; at 10 mg/kg, $p \leq 0.01$; and at 15 mg/kg, $p \leq 0.05$.

TABLE 11A

KEY TO SCORE RATING OF HALOPERIDOL-INDUCED
CATALEPSY IN MICE AND ITS REVERSAL BY VARIOUS AGENTS

Vertical Rod:

| | |
|---|---|
| Unable to grasp rod with limbs | 1 |
| Able to grasp but slips down | 2 |
| Able to grasp, partly slips, partly climbs down | 3 |
| Able to grasp, climbs down using all limbs | 4 |

Horizontal Rod:

| | |
|---|---|
| Unable to grasp, falls off rod | 1 |
| Able to grasp, unable to walk on rod more than 2 paces | 2 |
| Able to grasp, walks half-length of rod | 3 |
| Able to grasp, walks full length of rod | 4 |

Immobility Sitting Against Wall:

| | |
|---|---|
| Immobility > 5 min | 1 |
| Immobility 3–5 min | 2 |
| Immobility 1–3 min | 3 |
| Immobility 0.1 min | 4 |

Fractional scores are assigned, such as 2.5, when behavior falls between two categories, as between 2 and 3.

TABLE 12

RESTORATION OF MOTOR ACTIVITY IN RATS TREATED WITH
α-METHYL-p-TYROSINE (α-MpT) AT 100 mg/kg i.p.
Rats received the test drugs i.p. at the indicated doses.
After two hours they received α-MpT and were immediately placed in activity cages.
Total motor activity was automatically recorded for 10 hours, as described in the text.

| Dose, mg/kg | (R)-PAI Mesylate | | | Rac PAI Mesylate | | |
|---|---|---|---|---|---|---|
| | Score + SE | n | % of control | Score + SE | n | % of control |
| 2 | 14,132** ± 1457 | 7 | 89 | 9,035 ± 829 | 6 | 57 |
| 5 | 12,893* ± 1,869 | 7 | 81 | 10,926* ± 820 | 8 | 69 |
| 7.5 | 6,679 ± 414 | 4 | 42 | 9,698 ± 557 | 4 | 61 |
| Control saline | 15,862 ± 1,424 | 5 | 100 | | | |
| α-Mpt alone | 8,108*** ± 810 | 6 | 51 | | | |

TABLE 12-continued

RESTORATION OF MOTOR ACTIVITY IN RATS TREATED WITH
α-METHYL-p-TYROSINE (α-MpT) AT 100 mg/kg i.p.
Rats received the test drugs i.p. at the indicated doses.
After two hours they received α-MpT and were immediately placed in activity cages.
Total motor activity was automatically recorded for 10 hours, as described in the text.

| Dose, mg/kg | (R)-PAI Mesylate | | | Rac PAI Mesylate | | |
|---|---|---|---|---|---|---|
| | Score + SE | n | % of control | Score + SE | n | % of control |

Statistical significance by the Student's "t",
*p ≤ 0.01;
***p ≤ 0.001 for Test drugs + α-Mpt versus α-MpT alone
α-Mpt alone versus control saline
The scores of (R)-PAI versus racemic PAI are significantly different at 2 mg/kg, p ≤ 0.01.

Example 33
The Effects of (R) -PAI Mesylate Following Closed Head Injury in Rats
Methods
1. Induction of Trauma Head trauma was induced in male rats under ether anesthesia by a well calibrated weight-drop device that falls over the exposed skull, covering the left cerebral hemisphere, 1–2 mm lateral to the midline, in the midcoronal plane.

2. Evaluation of Motor Function

One hour after induction of trauma, the rats were tested by a set of criteria which evaluated their neurologic outcome (the criteria described by Shohami, et al., J. Neurotrauma, 10, 113 (1993)). These criteria, referred to as the Neurological Severity Score (NSS), consist of a series of reflexes and motor functions. Points are given based on deficits in these criteria. At 24h the rats were re-evaluated.

3. Evaluation of Brain Edema

The brains were removed after the second evaluation of motor function (24 h). A piece of tissue (~20 mg) was weighed to yield wet weight (WW). After drying in a desiccator oven for 24 h at 95° C., it was reweighed to yield dry weight (DW). Water percentage in the tissue was calculated as (WW−DW)×100/WW.

4. Drug Treatment (R)-PAI Mesylate was dissolved in water. The rats were injected intraperitoneally at a dose of 0.1 mg/kg, 0, 4, 8 and 12 h after induction of head trauma. Control rats were treated with water at the same times.

Results

The NSS, which measures the "clinical" status of the rats, was almost identical in the treated and nontreated groups at 1 hour after the head injury, but significantly lower at 24 hours in the (R)-PAI mesylate-treated rats (Table 13). These results indicate that PAI mesylate is effective in improving motor function recovery following closed head injury in rats.

At 24 hours after trauma, a major edema was found in the hemisphere (85.4% water in the brain of control rats vs. 78.5% in undamaged brain tissue). PAI mesylate was effective in reducing edema as verified by its effect on the percent of water.

In conclusion, the results reported herein demonstrate that (R)-PAI mesylate has neuroprotective properties in a model intended to mimic human nerve injury and to induce trauma to a closed skull.

TABLE 13

| | NSS | | Δ NSS | % H$_2$O |
|---|---|---|---|---|
| | 1 h | 24 h | (1 h–24 h) | in the brain |
| control (n = 6) | 15.6 | 12.3 | 4.3 ± 0.5 | 85.4 ± 0.4 |
| (R)-PAI Mesylate (n = 6) | 16.7 | 10.2 | 6.5 ± 0.7* | 82.1 ± 0.6** |

*P < 0.05 (Mann Whitney U-test)
**P < 0.005 (t-test)

Example 34
Effects of PAI Mesylate on Prevention of NMDA Induced Cell Death of Cerebellum Cell Cultures
Results of In vitro Assays Procedures: Cultures of mechanically dissociated neonatal rat cerebellum. The cerebellum are dissected aseptically from 6 or 7-day-old rat pups and placed in a 15 ml sterile plastic conic tube containing 3 ml of enriched medium (the medium is made up of Dulbecco's modified Eagle's medium (DMEM) with high glucose concentration (1 g/l), 2 mM (v/v) L-glutamine, antibiotic antimitotic mixture, and enriched with 15% (v/v) heat-inactivated fetal calf serum). The cerebellum are then dissociated after 20–25 passages through a sterile 13 gauge, 10 cm long stainless steel needle attached to a 5 ml syringe with an inserted 45 µm pore size nylon sieve. The dissociated cells are centrifuged at 200 g for 5 minutes, the supernatant discarded and the cells resuspended in enriched medium. The cell viability is determined by the trypan blue exclusion test. The cells are then plated at a density of 200/mm$^2$ on poly-L-lysine-coated surfaces (Poly-L-lysine-coated glass coverslips are prepared at least 1 hour before plating, by immersing in a sterile distilled water solution containing 15 µg/ml poly-L-lysine, and just before use, washing with sterile water and drying), covered with enriched medium, and incubated at 37° C. in an atmosphere of 5% $CO_2$ in air and 100% humidity. After 4 days in culture, the media are replaced with media containing the desired test compounds. Experiments are done in duplicate and repeated 2 or 3 times. After determining the test compound toxic dose-response, four groups are compared: (I) control (enriched medium alone), (II) test compound (one subgroup for each concentration (2 concentrations are tested)) , (III) N-methyl-D-aspartate (NMDA, exposure to a concentration of 1 mM for 3 h) as the cytotoxic challenge, (IV) test compound plus NMDA (one subgroup for each of the 2 concentrations of test compounds), (V) control group to test the effect of solvent (in which the test compound is dissolved), and (VI) an additional "positive control" group of spermine (0.01 μM dissolved in culture medium) plus NMDA. Nerve cell survival is evaluated by phase contrast microscopy and trypan blue staining after 24 h.

Results

It is well established that glutamic acid (Glu) possesses neurotoxic properties which are expressed in several neurological disorders including epilepsy and stroke, and most likely also in brain neurodegenerative diseases such as Parkinson's disease, Alzheimer's disease and traumatic brain injury. The neurotoxic effects of Glu are mediated by membrane bound Glu receptors, such as N-methyl-D-aspartate (NMDA) receptors.

The results, as shown in Table 14, demonstrate that 10 μM of (R)-PAI mesylate increased the survival of cerebellum cells by 27 percent following 1 μM NMDA exposure. These in vitro results support the in vivo effects of (R)-PAI mesylate presented in Examples 33 and 35, indicating that this drug has neuroprotective properties against neurotoxic concentration of NMDA.

TABLE 14

NEUROPROTECTIVE EFFECT OF (R)-PAI MESYLATE ON PREVENTION OF NMDA-INDUCED CELL DEATH OF CEREBELLUM CELLS

| Experimental Group | Surviving Cells | Percent Protection |
|---|---|---|
| Cerebellar Cultures (Toxicity $TD_{25}$ = 30 μM; $TD_{50}$ = 85 μM; $TD_{100}$ = 320 μM) | | |
| Control | 100 | |
| Solvent | 97 | |
| NMDA | 10 | |
| Solvent + NMDA | 10 | 0 |
| Compound + NMDA: | | |
| 1) 0.01 μM + NMDA | 12 | 2 |
| 2) 1.00 μM + NMDA | 22 | 12 |
| 3) 10.00 μM + NMDA | 37 | 27 |
| Spermine + NMDA | 75 | 65 |

Values, expressed as the percent of untreated controls, represent the average of 2 experiments run in duplicate for culture experiments, and the mean±SEM of 4 animals for ischemia. The percent protection value is the effect of the test compound after subtraction of the solvent effect.

Example 35
Effects of (R)-PAI Mesylate After Graded Crush of the Rat Optic Nerve Neuroprotective effects of (R) -PAI Mesylate were determined for application immediately after crush injury of the optic nerve in the adult rat. Short-term effects were measured metabolically, and long-term effects electrophysiologically.

Methods

Figure 19:
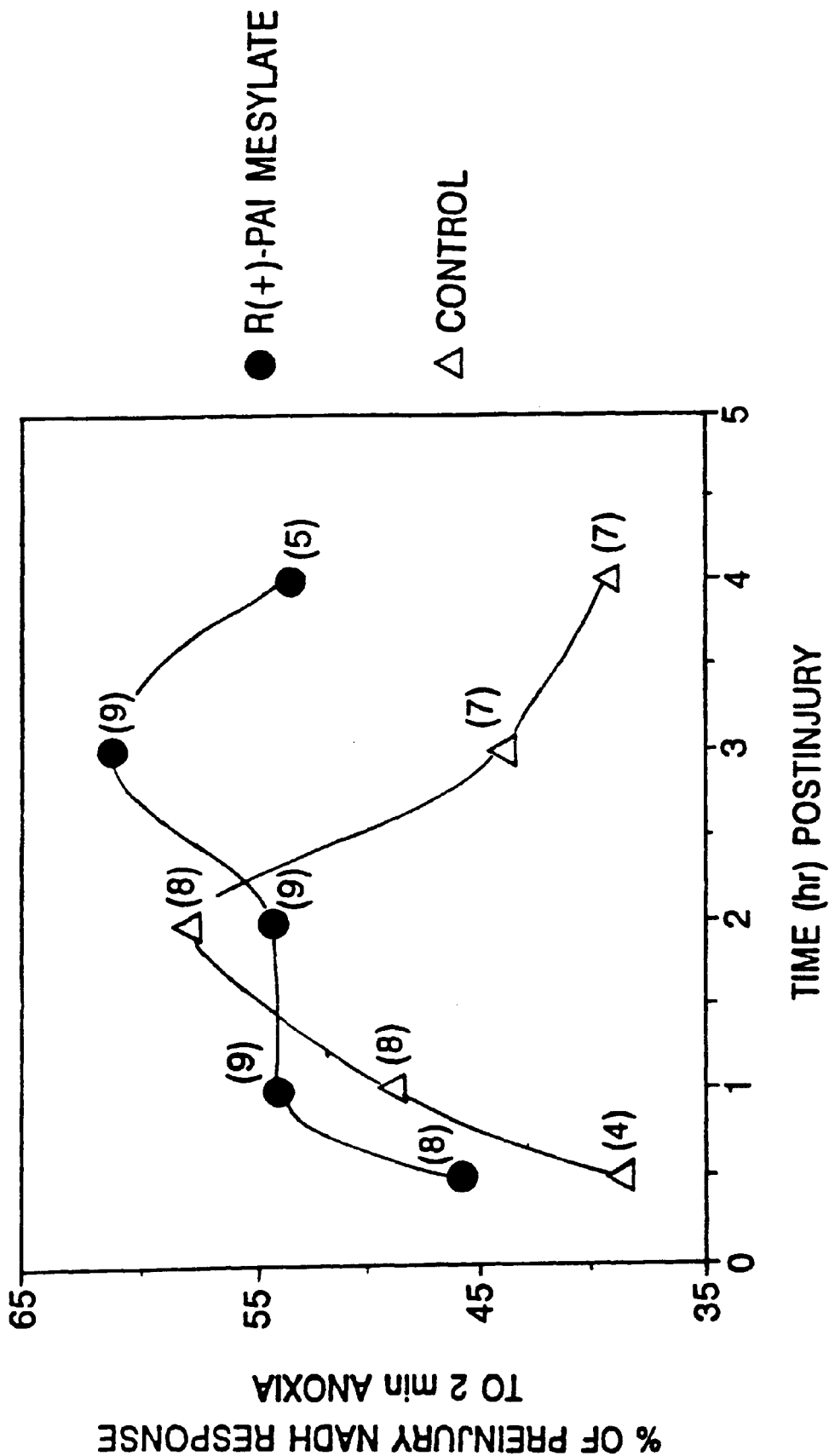
FIG. 19 is a graph showing the NADH response to 2 minutes of anoxia measured 30 minutes after injury and at half-hour intervals thereafter.

1. Metabolic Measurements a) General. The method is described by Yoles, et al., Investigative Ophthalmology & Visual Science, 33, 3586–91 (1992). At short terms, metabolic measurements were monitored in terms of the mitochondrial NADH/NAD ratio, which depends on the activity of the electron transport system, and thus indicate levels of energy production. Changes in ability of the nerve to produce energy as a consequence of injury were determined by comparing NADH levels in response to artificial transient anoxic insult before and after the injury.

b) Surface fluorometry—reflectometry. Monitoring of the intramitochondrial NADH redox state is based on the fact that NADH, unlike the oxidized form $NAD^+$, fluoresces when illuminated at 450 nm. A flexible Y-shaped bundle of optic fibers (light guide) was used to transmit the light to and from the optic nerve. The light emitted from the nerve was measured at two wavelengths: 366 nm (reflected light) and 450 nm (fluorescent light) . Changes in the reflected light were correlated with changes in tissue absorption caused by hemodynamic effects and with movements of the optic nerve secondary to alterations in arterial blood pressure and nerve volume. The fluorescence measurements were found to be adequately corrected for NADH redox state measurements by subtraction of the reflected light (366 nm) from the fluorescent light (1:1 ratio) to obtain the corrected fluorescence signal.

c) Animal preparation. Animal utilization was in accord with the ARVO Resolution on the use of animals in research. Male Sprague-Dawley (SPD) rats weighing 300–400 g were anesthetized with sodium pentobarbitone (50 mg/kg intraperitoneally). With the animal's head held in place by a head holder, a lateral canthotomy was performed under a binocular operating microscope and the conjuctiva was incised lateral to the cornea. After separation of the retractor bulbi muscles, the optic nerve was identified and a length of 3–3.5 mm was exposed near the eyeball by blunt dissection. The dura was left intact and care was taken not to injure the nerve. A special light-guide holder was implanted around the optic nerve in such a way that the light guide was located on the surface of the optic nerve 1 mm distal to the injury site. Animals, while still anesthetized, were allowed to recover for 30 minutes from the surgical procedures and were then exposed to anoxic conditions. An anoxic state was achieved by having the rat breathe in an atmosphere of 100% nitrogen for 2 minutes after which time it was returned to air. In order to evaluate the metabolic activity of the optic nerve, the relative changes in reflected and fluorescent light intensities in response to anoxia were measured before aid after crush injury.

d) Experimental protocol for crush injury and metabolic measurements. With the aid of calibrated cross-section forceps, a moderate crush injury was inflicted on the nerve between the eye and the light guide holder at a pressure corresponding to 120 g for 30 sec. Immediately after injury, animals received intraperitoneal injections of water with and without (R) -PAI Mesylate (2 mg/kg). To assess the activity of the energy production system, NADH response to 2 minutes of anoxia was measured in all animals prior to injury, 30 minutes after injury, and thereafter at hourly intervals up to 4 hours (see FIG. 19).

2. Electrophysiological Measurements

This method is described by Assia, et al., Brain Res., 476, 205–212 (1989). Animal preparation and optic nerve injury were preferred as in the metabolic studies. Immediately after injury, animals received a single injection of water with or without (R) -PAI Mesylate (0.5 mg/kg). Fourteen days after injury and treatment, the optic nerves were excised and measured electrophysiologically. Prior to removal of optic nerves for electrophysiologically measurement, the rats were deeply anesthetized with 70 mg/kg pentobarbitone. The skin was removed from the skull and the optic nerves were detached from the eyeballs. Subtotal decapitation was performed and the skull was opened with a rongeur. The cerebrum was displaced laterally, exposing the intracranial portion of the optic nerve. Dissection was at the level of the nerve, which was transferred to vials containing fresh salt solution consisting of NaCl (126 mM), KCl (3 mM), $NaH_2PO_4$ (1.25 mM), $NaHCO_3$ (26 mM), MgSO4 (2 mM), $CaCl_2$ (2 mM), and D-glucose (10 mM), and aerated with 95% $O_2$ and 5% $CO_2$ at room temperature. The nerves were kept in this solution, in which electrical activity remained stable for at least 3–4 hours. After 0.5 hours of recovery at room temperature, electrophysiological recordings were obtained from the nerve distal to the crush lesion. The nerve ends were then connected to two suction Ag-AgCl electrodes immersed in a bathing solution at 37° C. A stimulating pulse was applied through the electrode at the proximal end and the action potential was recorded by the distal electrode. A Grass SD9 stimulator was used for supramaximal electrical stimulation (0.5 pps). The measured signal was transmitted to a Medelec PA36 preamplifier and then to an electromyograph (Medelec MS7, AA7T amplifier). The solution, stimulator and amplifier had a common ground. The maximum amplitude of eight averaged compound action potentials (CAPs) was recorded and photographed with a Polaroid camera. The CAP values measured in contralateral uninjured nerves served as a reference.

Results

The results demonstrate that (R)-PAI Mesylate applied immediately after optic nerve injury blocked the injury-induced reduction in energy production. (R)-PAI Mesylate also has a long-term effect measured by electrophysiological monitoring.

The CAP (compound action potentials) amplitude is directly correlated with the number of conducting fibers in the tested segment of the nerve.

(R) -PAI Mesylate significantly attenuated the injury-induced loss of activity in the distal segment of the injured nerve, indicating that (R) -PAI Mesylate is a neuroprotective agent or at least slows down degeneration.

TABLE 15

Electrophysiological Measurements

| Group | CAP amplitude ($\mu V$) (Mean ± Std. Error.) |
|---|---|
| Vehicle N = 13 | 441 ± 95 |
| (R)-PAI Mesylate N = 7 | 2104 ± 313* |

Example 36

Comparison of Anticonvulsive Properties of R-PAI and S-PAI Salts

Both (R)-PAI and (S)-PAI HCl salts have significant anticonvulsant activities. In mice (i.p. administration) in the maximal electroshock test (MES test), (S)-PAI HCl has greater anticonvulsant activity ($ED_{50}$=57 mg/kg) than (R) -PAI HCl ($ED_{50}$=79 mg/kg). Analogous results were observed in rats (p.o. administration). Four out of four rats were protected from seizures in the MES test when 50 mg/kg of (S)-PAI HCl was administered, whereas three out of four mice were protected after the same dose of (R) -PAI HCl. With respect to efficacy for Parkinson's disease, the enhanced anticonvulsant activity is a detrimental side effect. The same trend occurs with the mesylate salts. (S) -PAI Mesylate has greater anticonvulsant activity than (R) -PAI Mesylate in the MES test. At doses of 100 mg/kg, (S)-PAI Mesylate Protected three out of three mice, whereas only one out of three mice was protected with (R)-PAI Mesylate.

The MES test is a classical model to indicate efficacy for partial and generalized seizures in humans. The agents' mechanism of action is via their ability to prevent the spread of seizures. Some agents, however, that prevent seizure spread have the side effect of lowering seizure threshold. These agents therefore have both proconvulsive and anticonvulsive side effects.

Results herein show that (S)-PAI Mesylate has proconvulsive activity. In the Timed Intravenous Infusion of Metrazol test, 141 mg/kg of (S)-PAI Mesylate reduces the time, and therefore the amount of Metrazol, required to induce the appearance of both the first focal seizure and the onset of clonus. Other agents that are classically used for partial and generalized seizures, such as phenytoin and carbamazepine, do not show this effect. (H. J. Kupferberg, Epilepsia, 30, s51–s56 (1989)). Likewise, (S) -PAI Mesylate showed a significantly higher acute neurotoxicity than (R)-PAI Mesylate. At 300 mg/kg, (R)-PAI Mesylate did not show any neurotoxicity with mice in the rotorod ataxia test. With (S)-PAI Mesylate, four out of four mice showed neurotoxicity and spasticity.

Methods $TD_{50}$ (median toxic dose). This test measures neurological deficits by the rotorod ataxia test. A mouse is placed on a knurled rod rotating at 6 rpm. It is then determined whether a mouse has the ability to maintain its equilibrium and stay on the rod for one minute in each of three trials.

Timed Intravenous Infusion of Metrazol Test. This test measures the minimal seizure threshold of each animal. Metrazol is infused at 0.185 mg/ml into the tail veins of mice. The time is then recorded (sec) from the start of infusion until the appearance of the first twitch (first focal seizure) and onset of clonus (clonic seizure). Proconvulsants require less Metrazol to produce these symptoms and therefore show endpoints at a shorter period of time.

Example 37

Peripheral Effects of (R)-PAI and (S)-PAI on the Contractility of Intestinal Smooth Muscle Preparations Peripheral effects of the hydrochloride salts of the enantiomers of PAI were determined in isolated rabbit or guinea-pig small intestine. These observations provide useful information on their relative peripheral side effects in humans. The first point of contact of the subject with an orally administered drug is the gastrointestinal tract where concentrations of the drug are much higher than after absorption and distribution. In the case of PAI hydrochloride (MW= 208), a 10 mg oral dose contained in a liquid volume of about 100 ml would be equivalent to a concentration of about 0.5 mM. In contrast, the therapeutic plasma concentration of (R)-PAI hydrochloride is in the nanomolar range.

The effect of the enantiomers of PAI in the isolated rabbit jejunum and the guinea-pig ileum were determined so as to find out whether the intake of (S) -PAI together with (R) -PAI (as found in racemic PAI) would produce side effects absent in the administration of pure (R)-PAI. (R)-PAI is the preferred enantiomer for the inhibition of MAO-B in the brain, in view of its potency and high selectivity towards this form of the enzyme. (S)-PAI is much less potent than (R)-PAI in this respect and is also not selective toward MAO-B. In principle, its presence in PAI racemate might be tolerated or overlooked provided (S)-PAI is inert at the recommended doses of (R)-PAI. The results provided in Tables 16–19 show that (S)-PAI is not an inert substance. On the contrary, in the guinea-pig ileum, it is a more potent relaxant than (R)-PAI. Hence its peripheral effects cannot be discounted as negligible. These data show that there would be fewer peripheral side effects in the administration of pure (R) -PAI than in the administration of racemic PAI containing an equivalent dose of (R)-PAI.

TABLE 16

TYRAMINE POTENTIATION BY EACH OF THE TWO ENANTIOMERS OF PAI HCl IN RATE JEJUNUM PREPARATION
A stretch of rabbit jejunum, mounted in an organ bath, displays rhythmic contractions that are inhibited by norepinephrine but not by tyramine. If however the jejunum is pretreated with a monoamine oxidase inhibitor such as PAI, then tyramine causes relaxation of the spontaneous contractions. The extent of relaxation can be correlated with the relative potency of the inhibitor.

| Drug and concentration ($\mu$M) | | Percent relaxation |
|---|---|---|
| Tyramine alone | 40 | 0 |
| Norepiniphrine | 0.002 | 100 |
| (R) PAI alone | 0.2–4.0 | 0 |
| (S) PAI alone | 0.2–4.0 | 0 |
| Tyramine | 40 | |
| after (R) PAI | 0.2 | 67 |
| | 2 | 88 |
| | 40 | 85–90 |
| after (S) PAI | 0.2 | 0 |
| | 2 | 35 |
| | 40 | 33–50 |

Results (S) -PAI is much less potent than (R) -PAI as an inhibitor of brain MAO-B. Therefore, (S)-PAI is not a useful agent for the prevention of brain dopamine degradation, but can potentiate the tyramine-evoked release of norepinephrine in the small intestine. Its activity in the small intestine is an undesirable side effect as it is expected to increase the absorption and action of undegraded tyramine. Thus, (S) -PAI is not an inert substance when used together with (R) -PAI as found in racemic PAI.

TABLE 17

ANTAGONISM OF BETHANECHOL-INDUCED CONTRACTIONS OF THE GUINEA PIG ILEUM PREPARATION IN THE PRESENCE OF 400 $\mu$M OF EACH OF THE TWO ENANTIOMERS OF PAI HCl
A stretch of guinea-pig ileum mounted in a physiological solution in an organ bath contracts dose-dependently when treated with bethanechol which is an enzymatically stable analog of the natural gastrointestinal neurotransmitter acetylcholine. These contractions are attenuated in the presence of PAI. The data are expressed in gram-tension.

| | gram-tension | | | |
|---|---|---|---|---|
| Bathenechol ($\mu$M) | control | (R) PAI | control | (S) PAI) |
| 0.8 | 0.5 | 0.2 | 0.6 | 0 |
| 2 | 1.5 | 0.3 | 2.0 | 0 |
| 4 | 2.2 | 0.7 | 3.0 | 0 |
| 8 | 4.0 | 1.0 | 3.8 | 0.6 |
| 20 | 5.6 | 2.0 | 3.8 | 1.2 |
| 40 | 6.2 | 2.8 | 3.8 | 1.7 |
| 80 | 6.2 | 3.1 | 3.8 | 2.6 |
| 200 | 6.2 | 4.3 | 3.8 | 2.6 |

Results (S) -PAI is almost inactive as a MAO-B inhibitor with respect to (R)-PAI, and hence is not effective in preventing the degradation of brain dopamine. However, it is more effective than R(PAI) in the prevention of the bethanechol-induced contraction of the small intestine. Thus (S)-PAI is not an inert substance when used with R(PAI) as found in racemic PAI.

TABLE 18

ANTAGONISM OF THE HISTAMINE-INDUCED CONTRACTIONS OF THE GUINEA-PIG ILEUM PREPARATION BY EACH OF THE TWO ENANTIOMERS OF PAI HCl
A fixed dose of histamine (40 nM) causes a sustained contraction of a stretch of guinea-pig ileum mounted in physiological solution in an organ bath. Incremental addition of each of the two enantiomers of PAI HCl causes a dose-dependent relaxation of the muscle. Results are expressed as percent relaxation with respect to the baseline before addition of histamine, which is taken as 100% relaxation.

| PAI concentration | Percent relaxation | |
|---|---|---|
| $\mu$M | (R) PAI | (S) PAI |
| 2 | 0 | 11 |
| 4 | 0 | 15 |
| 10 | 0 | 30 |
| 20 | | 20 |
| 30 | 31 | 33 |
| 40 | 37 | 36 |
| 100 | 81 | 71 |
| 200 | | 90 |
| 300 | 92 | |
| 400 | 100 | 98 |
| 700 | 100 | |
| 1000 | | 100 |

Results (S)-PAI is inactive with respect to (R)-PAI as a MAO-B inhibitor in the brain, and hence useless for preventing the degradation of brain dopamine, but is more active than the (R) isomer in causing relaxation of intestinal smooth muscle. Thus, (S) -PAI is not an inert substance when taken together with the (R)isomer as found in racemic PAI.

TABLE 19

ANTAGONISM OF THE BETHANECHOL-INDUCED
CONTRACTIONS OF THE GUINEA-PIG ILEUM PREPARATION
BY EACH OF THE TWO ENANTIOMERS OF PAI HCl
A fixed dose of bethanechol (0.8 $\mu$M) causes a sustained contraction
of a stretch of guinea-pig ileum mounted in physiological solution in
an organ bath. Incremental addition of each of the two enantiomers
of PAI HCl causes a dose-dependent relaxation of the preparation.
Results are expressed as percent relaxation with respect to the
baseline before addition of histamine, which is taken as 100% relaxation.

| PAI concentration | Percent relaxation | |
|---|---|---|
| $\mu$M | (R) PAI | (S) PAI |
| 20 | 25 | 40–50 |
| 60 | 25–50 | 60–70 |
| 100 | 50–70 | 100 |
| 300 | 100 | 100 |

Results (S)-PAI is inactive with respect to (R)-PAI as a MAO-B inhibitor in the brain, and hence useless for the prevention of the degradation of brain dopamine, but is more active than the (R) isomer in causing relaxation of intestinal smooth muscle. Thus, (S)-PAI is not an inert substance when taken together with the (R) isomer as found in racemic PAI.

Example 38

Some Effects of [R] (+) PAI Mesylate if Middle Cerebral Artery Occlusion in the Rat as a Model for Stroke Methods 1.1. Middle Cerebral Artery Occlusion (MCAO) in the Rat A modification of the procedure described by Tamura et al (1981) was used. Male Wistar rats (Olac England-Jerusalem) 300–400 g each were anesthetized with a solution of Equitesine administered i.p. at a dose of 3 mL/kg. Equitesine consists of 13.5 mL sodium pentothal solution (60 mg/mL), 3.5 g chloral hydrate, 1.75 g $MgSO_4$, 33 mL propylene glycol, 8.3 mL absolute alcohol made up to 83 mL with distilled water. Surgery was performed with the use of a high magnification operating microscope, model SMZ-2B, type 102 (Nikon, Japan). In order to expose the left middle cerebral artery, a cut was made in the temporal muscle. The tip of the coronoid process of mandible was excised as well and removed with a fine rongeur. Craniectomy was made with a dental drill at the junction between the median wall and the roof of the inferotemporal fossa. The dura matter was opened carefully using a 27 gauge needle. The MCA was permanently occluded by microbipolar coagulation at low power setting, beginning 2–3 mm medial to the olfactory tract between its cortical branch to the rhinal cortex and the laterate striate arteries.

After coagulation, the MCA was severed with microscissors and divided to ensure complete occlusion. Following this, the temporalis muscle was sutured and laid over the craniectomy site. The skin was closed with a running 3–0 silk suture. A sham craniectomy operation was performed on a parallel group of rats, but without cauterization of the MCA. During the entire surgical operation (20–25 min) in either group, body temperature was maintained at 37 to 38° C. by means of a body-temperature regulator (Kyoristsu, Japan) consisting of a self-regulating heating pad connected to a rectal thermistor. At 24 hours post surgery a neurological score was taken in order to assess the severity of the injury in the drug-treated rats with respect to their untreated controls. At 48 hours, the animals were anesthetized with Equitesine and the severity of the injury was visualized by an MRI procedure. The volume of brain tissue incurring damage following ischemia was determined.

1.2. Drug Administration

[R] (+)PAI Mesylate was administered as an i.p.injection in 0.3–0.4 mL distilled water, according to the following schedule:

1 mg/kg immediately after surgery.

0.5 mg/kg 2 hours after surgery 1 mg/kg 20–24 hours after surgery 1.3. MRI Scan of Ischaemic Brain Lesion All experiments were performed using a 4.7 T BIOSPEC system (BRUKER) (See T. Back, et al., "Diffusion Nuclear Magnetic Resnonance Imaging in Experimental Stroke: Correlation with Cerebral Metabolites," *Stroke* (February 1994) 25: 494–500). Forty-eight hours after MCAO or sham operation, every animal was subjected to a fast multislices T1 weighted imaging (TR/TE), (500/25) for positioning. Then multislices T2-weighted images (3000/80) were acquired (5 contiguous slices, 3 mm thick).

The size and severity of the infarcted area was estimated using the hyperintensity observed in the T2 weighted MRI at 48 hours post-occlusion or post sham-operation. The following MRI parameters were determined for each group of rats:

c. Ischemic area (in $mm^2$)

d. Area of the ischemic hemisphere (in $mm^2$)

e. Area of the unaffected hemisphere (in $mm^2$)

The use of contiguous slices allows the conversion of area units into volume units by simply multiplying the area value by the slice thickness.

1.4. Neurological Score

The neurological score consists of the sum total of a series of ratings assigned to the performance of specific locomotor activities in a given rat. The scale runs from 0 (fully normal rats) to 13 (fully incapacitated rats). Most parameters are rated as either 0 (normal), or 1 (incapacitated); others are graded. The following tests were used in the present study:

General observational tests: hypoactivity; sedation; piloerection

Motor reflex. Rats were lifted by the tail about 15 cm above the floor. Normal rats assume a posture in which they extend both forelimbs towards the floor and spread the hind limbs to the sides in a trapeze-like manner. MCAO when severe causes consistent flexion of the contralateral limb.

Motor ability. This is seen as the ability to grasp a rod 1 cm in diameter by the contralateral limb for 5–15 sec when the rat is left hanging on the rod through the arm pit.

Motor coordination. Normal rats are able to walk up and down a beam 5 cm wide placed at a moderate slant. Failure to walk the beam in either direction reveals some motor incoordination, lack of balance and limb weakness.

Gait. Ability to restore normal position to either hind contralateral limb when intentionally displaced while on a narrow beam.

Balance. Ability to grasp and balance on a narrow beam 2 cm wide.

Locomotor activity. Total movements over a period of 15 min in an automated activity cage.

Ratings assigned to each of the above parameters are given in Table 20.

TABLE 20

Neurological scores assigned to each of 10 parameters of posture and locomotion

| Parameter | Score |
|---|---|
| a. Activity in the home cage | normal = 0 |
| | hypoactive = 1 |
| b. Sedation | none = 0 |
| | marked = 1 |
| c. Piloeretion | none = 0 |
| | marked = 1 |
| d. Extension of contralateral forelimb towards floor when lifted by tail | good= 0 flexed limb = 1 |
| e. Spread of contralateral hind limb when lifted by tail (trapezoid posture) | good= 0 flexed limb = 1 |
| f. Grasp rod with contralateral limb for 5–15 sec. when suspended by the armpit | good = 0 poor = 1 |
| g. Walk on beam 5-cm wide | good = 0 poor = 1 |
| h. Restoration of contralateral hind and or fore limb to original position when intentionally displaced | good = 0 poor = 1 (one limb) 2 (two limbs) |
| i. Grasping and balance on beam 2-cm wide | good = 0 poor = 1 |
| j. Motor activity with respect to control (for 15 min in an automated activity cage | ≦25% of control 3 26–50% of control 2 51–75% of control 1 76–100% of control 0 |

2. Results

2.1. Infarct Size

Figure 20:
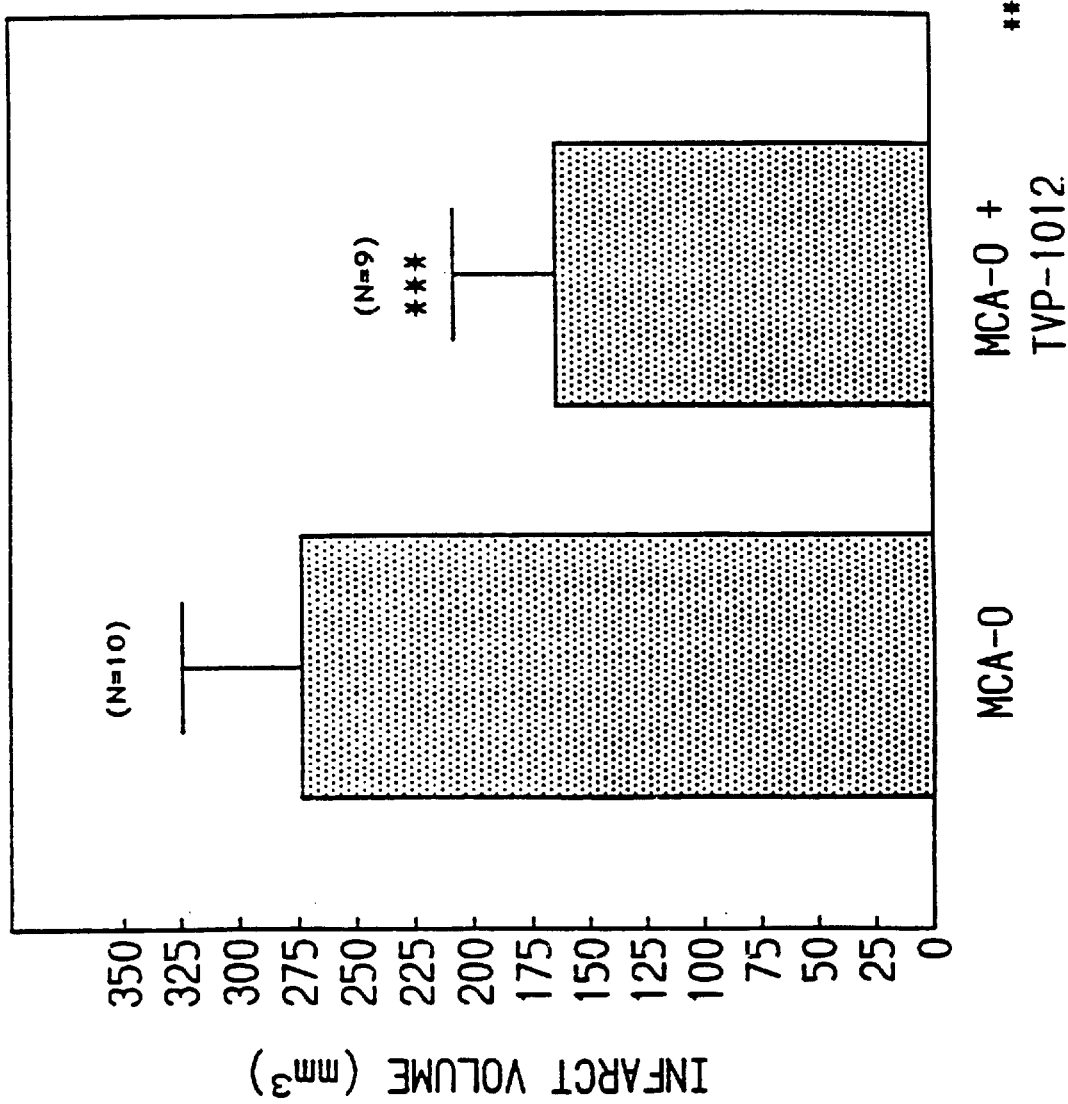
FIG. 20: Ischemic brain lesion evaluation with MRI T2-scan 48 hours after MCA-O and [R] (+)PAI Mesylate Treatment in rats: The middle cerebral artery was surgically occluded as described in Example 38. [R] (+)PAI Mesylate was administered as follows: 1.0 mg/kg ip immediately after surgery; 0.5 mg/kg ip, 2 hrs after surgery; 1.0 mg/kg ip, 24 hrs after surgery. Infarct volume ($mm^3$) was determined by MRI 48 hours following surgery.

The results of the MRI study are summarized in Table 21 and FIG. 20. The infarct size was significantly smaller in [R] (+)PAI Mesylate-treated rats (n=9) than in untreated rats (n=10). In the former, the infarct size was about 60% of that in the untreated animals.

TABLE 21

Ischaemic brain lesion evaluation by MRI T2-SCAN - 48 hrs following MCA-Occlusion and [R] (+) PAI Mesylate treatment in Wistar Rats.

| MCA-O | | MCA-O + [R] (+) PAI Mesylate* | |
|---|---|---|---|
| Animal No. | Infarct size (mm$^3$) | Animal No. | Infarct size (mm$^3$) |
| 1 | 252 | 1 | 94.4 |
| 2 | 272 | 2 | 139 |
| 3 | 314 | 3 | 240 |
| 4 | 273 | 4 | 137 |
| s | 201 | 5 | 137 |
| 6 | 221 | 6 | 174 |
| 7 | 358 | 7 | 164 |
| 8 | 265 | 8 | 171 |
| 9 | 341 | 9 | 215 |
| 10 | 236 | | |
| MEAN ± SD | 273.3 ± 50.9 | MEAN ± SD | 163.5 ± 43.9 | t = 5.0475
f = 17
p < 0.001
[R] (+) PAI Mesylate reduces infarct size by 40% significantly
*[R] (+) PAI Mesylate administered:
Time after MCA-Occlusion:
0         −1.0 mg/kg ip;
2 hrs    −0.5 mg/kg ip;
24 hrs  −1.0 mg/kg ip.

2.2. Neurological score

Figure 21:
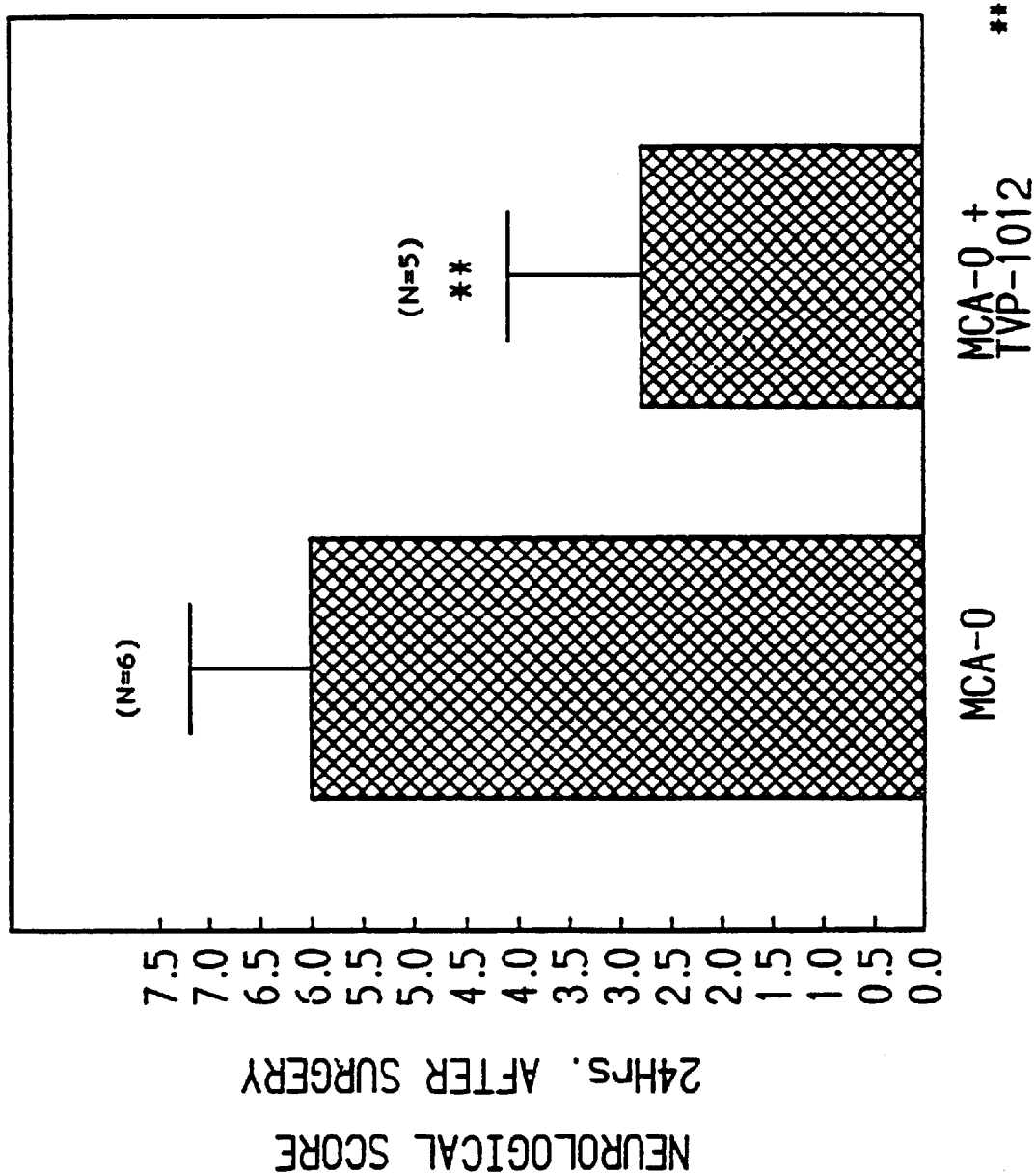
FIG. 21: Neurological evaluation of Wistar rats subjected to MCA-O and [R] (+)PAI Mesylate Treatment: The middle cerebral artery was surgically occluded and [R] (+)PAI Mesylate administered as in FIG. 20. At 24 hours post surgery a neurological score was taken as described in is Example 38.

The neurological score in five [R] (+)PAI Mesylate treated rats and six untreated rats were determined by a blinded observer. The results are given in Table 22 where they are compared with the infarct size in each animal as determined by the MRI test, and also in FIG. 21. It can be seen that those animals with the least neurological scores were those treated with [R] (+) PAI Mesylate. The neurological score was reduced by 54% and the infarct size by 36% in [R] (+)PAI Mesylate-treated MCAO rats as compared to untreated ones.

TABLE 22

Neurological score of Rats submitted to MCA-Occlusion and [R] (+) PAI Mesylate treatment with relation to their ischaemic infarct size.

| MCA-O | | | MCA-O + [R] (+) PAI Mesylate*** | | |
|---|---|---|---|---|---|
| Animal No. | Neurological * Score | Infarct size** (mm$^3$) | Animal No. | Neurological * Score | Infarct size** (mm$^3$) |
| 1 | 5.0 | 201 | 1 | 1.0 | 137 |
| 2 | 5.0 | 221 | 2 | 2.0 | 174 |
| 3 | 6.0 | 358 | 3 | 4.0 | 164 |
| 4 | 6.0 | 265 | 4 | 4.0 | 171 |
| 5 | 8.25 | 341 | 5 | 2.88 | 215 |
| 6 | 5.75 | 236 | | | |
| MEAN ± SD | 6.0 ± 1.19 | 270 ± 65 | MEAN ± SD | 2.78 ± 1.3 | 172 ± 28 |

| Neurological Score | Infarct Size |
|---|---|
| t = 4.25 | t = 3.34 |
| f = 9 | f = 9 |
| p < 0.01 | p < 0.01 |

[R] (+) PAI Mesylate reduces the neurological score by 53.7% and infarct size by 36.3%.
* Examined 24 hrs after MCA-Occlusion.
**Evaluated by MRI T2-SCAN 48 hrs after MCA-Occlusion.
***[R] (+) PAI Mesylate administered:
Time after MCA-Occlusion:
0         −1.0 mg/kg ip;
2 hrs    −0.5 mg/kg ip;
24 hrs  −1.0 mg/kg ip.

REFERENCES FOR EXAMPLE 38

Cechetto D F, Wilson J X, Smith K E, Wolski D, Silver M D, Hachinski V C (1989). Autonomic and myocardial changes in middle cerebral artery occlusion: stroke models in the rat. Brain Res 502:296–305.

Kolb B, Sutherland R J, Whishaw I Q (1983). A comparison of the contributions of the frontal and parietal association cortex to spatial localizations in the rat. Behav. Neurosci. 97:13–27.

Menzies S A, Hoff J T, Betz A L (1992). Middle cerebral artery occlusion in rats: A neurological and pathological evaluation of a reproducible model. Neurosurgery 31:100–106.

Sauer D, Allegrini P R, Cosenti A, Pataki A, Amaceker H, Fagg G E (1993). Characterization of the cerebroprotective efficacy of the competitive NMDA receptor antagonist CGP40116 in a rat model of focal cerebral ischemia: An in vivo magnetic resonance imaging study. J. Cerebr. Blood Flow and Metabol. 13:595–602.

Stephanovich C, Editor, Stroke: Animal Models, Pergamon Press, 1983

Tamura A, Graham D I, McCulloch J, Teasdale G H (1981). Focal cerebral ischemia in the rat: 1. Description of technique and early neuropathological consequences following MCA occlusion. J. Cereb. Blood Flow and Metab. 1:53–60.

Teasdale G, Tyson G, Tamura A, Graham D I, McCulloch J. Focal cerebral ischaemia in the rat: Neuropatholgy, local cerebral blood flow and cerebrovascular permeability. In Stroke: Animal Models, Stephanovic C, Editor, Pergamon Press 1983, pp.83–97.

Yamamoto M, Tamura A, Kirino T, Shimitzu M, Sano K (1988). Behavioral changes after focal cerebral ischemia by left middle cerebral artery occlusion in rats. Brain Re. 452:323–328

Yamori Y et al. (1976). Pathogenic similarity of strokes in stroke prone spontaneously hypertensive rats and humans. Stroke 7:46–53.

Young W, DeCrescito V, Flamm E S, Hadani M, Rappaport H, Cornu P (1986). Tissue Na, K, and Ca changes in regional cerebral ischemia: Their measurement and interpretation. Central Nervous System Trauma, 3:215–234.

What is claimed is:

1. A method of treating multiple sclerosis in a subject which comprises administering to the subject an amount of R(+)-N-propargyl-1-aminoindan or a pharmaceutically acceptable salt thereof effective to treat multiple sclerosis in the subject.

2. The method of claim 1, wherein the pharmaceutically acceptable salt of R(+)-N-propargyl-1 aminoindan is selected from the group consisting of:

the mesylate salt;

the esylate salt;

the sulfate salt; and the hydrochloride salt.

3. The method of claim 2, wherein the pharmaceutically acceptable salt of R(+)-N-propargyl-1-aminoindan is the mesylate salt.

4. The method of claim 1, wherein the effective amount of R(+)-N-propargyl-1-aminoindan or a pharmaceutically acceptable salt thereof to be administered is from about 0.5 milligrams per kilogram body weight of the subject to about 2.5 milligrams per kilogram body weight of the subject.

5. The method of claim 1, wherein the R(+)-N-propargyl-1-aminoindan or pharmaceutically acceptable salt thereof is administered intravenously, orally, rectally, transdermally, or parenterally.

6. The method of claim 5, wherein the R(+)-N-propargyl-1-aminoindan or pharmaceutically acceptable salt thereof is administered intravenously.

7. The method of claim 1, wherein the subject is human and the effective amount is from about 0.01 mg to 50.0 mg per day.

8. The method of claim 7, wherein the effective amount is from about 0.1 to 10.0 mg per day.

9. The method of claim 5, wherein the R(+)-N-propargyl-1-aminoindan or pharmaceutically acceptable salt thereof is administered orally.

10. The method of claim 1, wherein the R(+)-N-propargyl-1-aminoindan or a pharmaceutically acceptable salt thereof is supplemented with a pharmaceutically acceptable carrier, which is a liquid; or a gel pharmaceutical.

11. The method of claim 10, wherein the amount of the salt of R(+)-N-propargyl-1-aminoindan administered is an amount from about 0.1 mg to about 100 mg.

12. The method of claim 11, wherein the amount of the salt of R(+)-N-propargyl-1-aminoindan administered is an amount from about 1 mg to about 10 mg.

* * * * *

UNITED STATES PATENT AND TRADEMARK OFFICE
CERTIFICATE OF CORRECTION

| | |
|---|---|
| PATENT NO. | : 6,316,504 B1 |
| APPLICATION NO. | : 08/952705 |
| DATED | : November 13, 2001 |
| INVENTOR(S) | : Moussa B.H. Youdim et al. |

It is certified that error appears in the above-identified patent and that said Letters Patent is hereby corrected as shown below:

1. On the title page, item [75], inventors David Lerner, Haim Yellin, and Alex Veinberg should be excluded and should read -- Moussa B.H. Youdim; John P.M. Finberg, both of Tivon; Ruth Levy, Tel Aviv; Jeffrey Sterling, Jerusalem, all of (IL) --.

2. On the title page, item [63], the following related application data should appear: -- Title Page, Item [63] Related U.S. Application Data: This application is a § 371 of PCT International Application No. PCT/US96/07465, filed May 22, 1996 which claims priority of and is a continuation of U.S. application No. 08/446,439, filed on May 22, 1995, now U.S. Pat. No. 5,744,500, issued April 28, 1998, which was a continuation-in-part of application No. 08/139,517, filed October 18, 1993, now abandoned. --

3. On the title page, item [56], in the fifth citation under "OTHER PUBLICATIONS," "fo" should read -- of -- and "1346" should read -- 1364 --.

4. In column 30, line 33, "3.s" should read -- 3.5 --.

5. In column 34, lines 1-7, in Table 11A, the lines should be re-positioned so that it is no longer fragmented from the rest of the contents of Table 11A.

6. In claim 10, line 34, "which is a liquid; or a gel pharmaceutical" should read -- which is a solid; a liquid; or a gel. --

Signed and Sealed this

Thirteenth Day of May, 2008

JON W. DUDAS
*Director of the United States Patent and Trademark Office*